(12) United States Patent
Yeung et al.

(10) Patent No.: US 6,788,414 B1
(45) Date of Patent: Sep. 7, 2004

(54) METHOD OF ANALYZING MULTIPLE SAMPLE SIMULTANEOUSLY BY DETECTING ABSORPTION AND SYSTEMS FOR USE IN SUCH A METHOD

(75) Inventors: Edward S. Yeung, Ames, IA (US); Xiaoyi Gong, Edison, NJ (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 10/070,531

(22) PCT Filed: Jul. 28, 2000

(86) PCT No.: PCT/US00/20447

§ 371 (c)(1),
(2), (4) Date: Jun. 5, 2002

(87) PCT Pub. No.: WO01/18528

PCT Pub. Date: Mar. 15, 2001

Related U.S. Application Data

(60) Provisional application No. 60/153,263, filed on Sep. 9, 1999.

(51) Int. Cl.⁷ .............................................. G01N 21/59
(52) U.S. Cl. ...................................... 356/436; 356/440
(58) Field of Search ................................ 356/436, 440

(56) References Cited

U.S. PATENT DOCUMENTS

| | | | | |
|---|---|---|---|---|
| 3,627,431 A | * | 12/1971 | Komarniski | ................ 356/409 |
| 5,324,401 A | * | 6/1994 | Yeung et al. | ................ 204/452 |
| 5,741,411 A | | 4/1998 | Yeung et al. | |
| 5,900,934 A | * | 5/1999 | Gilby et al. | ................ 356/344 |
| 5,954,931 A | | 9/1999 | Maracas et al. | |

FOREIGN PATENT DOCUMENTS

WO    WO 00/06996 A1    2/2000

* cited by examiner

Primary Examiner—Richard A. Rosenberger
(74) Attorney, Agent, or Firm—McKee, Voorhees & Sease, P.L.C.

(57) ABSTRACT

The present invention provides a method of analyzing multiple samples simultaneously by absorption detection. The method comprises: (i) providing a planar array of multiple containers, each of which contains a sample comprising at least one absorbing species, (ii) irradiating the planar array of multiple containers with a light source and (iii) detecting absorption of light with a detetion means that is in line with the light source at a distance of at leaat about 10 times a cross-sectional distance of a container in the planar array of multiple containers. The absorption of light by a sample indicates the presence of an absorbing species in it. The method can further comprise: (iv) measuring the amount of absorption of light detected in (iii) indicating the amount of the absorbing species in the sample. Also provided by the present invention is a system for use in the abov metho.The system comprises; (i) a light source comrnpising or consisting essentially of at leaat one wavelength of light, the absorption of which is to be detected, (ii) a planar array of multiple containers, and (iii) a detection means that is in line with the light source and is positioned in line with and parallel to the planar array of multiple contiainers at a distance of at least about 10 times a cross-sectional distance of a container.

49 Claims, 34 Drawing Sheets

```
         1                  11                  21                  31
H₂N-L-I-V-T-Q-T-M-K-G-L-D-I-Q-K-V-A-G-T-W-Y-S-L-A-M-A-A-S-D-I-S-L-L-D-A-Q-S-A-P-L-R-
         41                 51                  61                  71
   V-Y-V-E-E-L-K-P-T-P-E-G-D-L-E-I-L-L-Q-K-W-E-N-G-E-C-A-Q-K-K-I-I-A-E-K-T-K-I-P-A-
         81                 91                  101                 111
   V-F-K-I-D-A-L-N-E-N-K-V-L-V-L-D-T-D-Y-K-K-Y-L-L-F-C-M-E-N-S-A-E-P-E-Q-S-L-A-C-Q-
         121                131                 141                 151
   C-L-V-R-T-P-E-V-D-D-E-A-L-E-K-F-D-K-A-L-K-A-L-P-M-H-I-R-L-S-F-N-P-T-Q-L-E-E-Q-C-
         161
   H-I-COOH
```

*Fig. 11*

METHOD OF ANALYZING MULTIPLE SAMPLE SIMULTANEOUSLY BY DETECTING ABSORPTION AND SYSTEMS FOR USE IN SUCH A METHOD

This application claims the benefit of provisional application ser. No. 60/153,263 filed Sep. 9, 1999.

STATEMENT OF GOVERNMENT RIGHTS

This invention was made with government support under Contract No. W-7405-Eng-82 awarded by the U.S. Deparment of Energy. Therefore, the Government may have certain rights to this invention.

TECHNICAL FIELD OF THE INVENTION

This invention relates to a method of analyzing multiple samples simultaneously by detecting absorption and systems for use in such a method.

BACKGROUND OF THE INVENTION

The rapid development of biological and pharmaceutical technology has posed a challenge for high-throughput analytical methods. For example, current development of combinatorial chemistry has made it possible to synthesize hundreds or even thousands of compounds per day in one batch. Characterization and analysis of such huge numbers of compounds have become the bottleneck. Parallel processing (i.e., simultaneous multi-sample analysis) is a natural way to increase the throughput. However, due to limitations related to column size, pressure requirements, detector and stationary phase material, it will be very difficult to build a highly multiplexed high-performance liquid chromatography (HPLC) system. The same goes for building a highly multiplexed gas chromatography (GC) system.

High performance capillary electrophoresis (CE) has rapidly become an important analytical tool for the separation of a large variety of compounds, ranging from small inorganic ions to large biological molecules. With attractive features such as rapid analysis time, high separation efficiency, small sample size, and low solvent consumption, CE is being increasingly used as an alternative or complementary technique to HPLC. For example, the use of capillary gel electrophoresis has greatly improved DNA sequencing rates compared to conventional slab gel electrophoresis. Part of the improvement in speed, however, has been offset by the loss of the ability (inherent in slab gels) to accommodate multiple lanes in a single run. Highly multiplexed capillary electrophoresis, by making possible hundreds or even thousands of parallel sequencing runs, represents an attractive approach to overcoming the current throughput limitations of existing DNA sequencing instrumentation. Such a system has been disclosed in U.S. Pat. Nos. 5,582,705 (Yeung et al.), 5,695,626 (Yeung et al.), and 5,741,411 (Yeung et al.). In this system, light-induced fluorescence is exclusively employed as the detection method.

While fluorescence detection is suitable for DNA sequencing applications because of its high sensitivity and special labeling protocols, UV absorption detection has remained very useful because of its ease of imnplementation and wide applicability, especially for the deep-UV (200–220 nm) detection of organic and biologically important compounds. A capillary isoelectric focusing system using a two-dimensional CCD detector, in which one dimension represents the capillary length and the other dimension records the absorption spectrum, has been described by Wu and Pawliszyn, *Analyst* (*Cambridge*), 120, 1567–1571 (1995). The system has been used for two capillary tubes but is not easily adapted for three or more capillary tubes because the system requires the capillary tubes to be separated by space. Instead of providing wavelength resolution in the second CCD dimension, isoelectric focusing in two capillary tubes is simultaneously monitored. The use of optical fibers for illumination, however, has led to low light intensities and poor UV transmission. So, only visible wavelengths have been employed for the detection of certain proteins. Because the CCD has a very small electron well capacity (about 0.3 million electrons), the limit of detection (LOD) of this system is litnited by the high shot noise in absorption detection. The use of the CCD produces an overwhelming amount of data per exposure, limiting the data rate to one frame every 15 seconds. Also, the imaging scheme utilized is not suitable for densely packed capillary arrays because of the presence of mechanical slits to reict the light paths. Further, in order to avoid cross-talk, only square capillaries can be used.

Photodiode arrays (PDA) are used in many commercial CE and HPLC systems for providing absorption spectra of the analytes in real time. Transmitted light from a single point in the flow stream is dispersed by a grating and recorded across the linear array. A capillary zone electrophoresis system using a photodiode array as the imaging absorption detector has been described by Culbertson and Jorgenson, *Anal. Chem.*, 7, 2629–2638 (1998). Different elements in the array are used to image different axial locations in one capillary tube to follow the progress of the separation. Because the PDA has a much larger electron well capacity (tens of million electrons), it is superior to the CCD for absorption detection. Time-correlated integration is applied to improve the signal-to-noise ratio (S/N).

What is still needed is an absorption detection approach for the simultaneous analysis of multiple systems. One such system is shown in U.S. Pat. No. 5,900,934 (Gilby et al.). This system includes a photodetector array comprising a plurality of photosensitive elements connected to provide a serial output. The elements are typically pixels of a photodiode array (PDA). The elements are illuminated by a light source positioned to illuminate at least a portion of the photodetector array. The light source may be an AC or DC mercury lamp or other useable light source for chromatography. An array of separation channels is disposed between the light source and the photodetector array, each of the separation channels having a lumen, a sample introduction end and a detection region disposed opposite the sample introduction end. The array is a multiple parallel capillary electrophoresis system. A mask element having at least one aperture for each associated separation channel is required. Each aperture corresponds to its associated separation channel, thereby selectively permitting light from the light source to pass through the lumen of its associated separation channel. At least a portion of the light passing through the lumen of the associated separation channel falls on a respective photosensitive element of the photodetector array to effectt masurement of absorption of light by a sample introduced into the sample introduction end of the associated separation channel.

The system described by Gilby et al. has disadvantages because it limits the amount of light impinging on the separation channel, providing less than desirable light intensity to the PDA. Further, aligning the apertures and the mask elements with the separation channels, e.g., capillaries, is difficult for several reasons. For example, positioning the capillaries with equal separation there between is difficult as the capillaries generally are not of equal dimension, e.g., diameter tolerances vary greatly. Further, for example, the mask geometry does not provide identical light paths, which leads to nonlinear response. Also, a mask can produce stray light, which leads to poor detection limits, and does not completely eliminate crosstalk from the adjacent capillaries, since the light beams are diverging and cannot escape the detector element. In addition, a mask can be difficult to manufacture, due to the requirement of uniformity. Also, Gilby places the sample and the PDA too close together, resulting in stray light, cross talk and the inability to use the maximum pathlength of light.

Thus, in view of the disadvantages inherent to the methods and systems in the art, there remains a need a method of analyzing multiple samples simultaneously by absorption detection. It is an object of the present invention to provide such a method. It is another object of the present invention to provide a system for use in such a method. These and other objects and advantages of the present invention as well as additional inventive features will become apparent to one of ordinary skill in the art from the detailed description provided herein.

The present invention also addresses other disadvantages in the art. For example, since the invention of the polymerase chain reaction (PCR) in 1985 by Kary Mullis, the uiate in sensitivity, together with increasing ease in implementation, have placed this technique in a central position in molecular biology research and in clinical diagnosis (Rolf et al., PCR: Clinical Diagnostics and Research, 1992, Springer-Verlag, Berlin and Heidelberg). In the last ten years; PCR has stimulated numerous investigations in genetic analysis, and is even being used to determine the genetic basis of complex diseases (Sack et al., *Science* 230: 1350 (1985)). There is no need to reiterate the development of CE as a powerfuil analytical tool in post-PCR analysis. A large amount of research has been done to explore the advantages of CE over traditional slab gel electrophores, including high-speed, high-resolution restriction fragments analysis (Guttman et al., *Anal. Chem.* 62: 2348 (1992); Milofsky et al., *Anal. Chem.* 65: 153 (1993); Williams et al., *J. Chromatogr.* A680: 525 (1994); Chang et al., *J. Chromatogr.* B669: 113 (1995); Barron et al., *Electrophoresis* 16: 64 (1995); and Righetti et al., *Anal. Biochem.* 244: 195 (1997)), high-speed, high-throughput DNA sequencing (Ruiz-Martinez et al., *Anal. Chem.* 65: 2851 (1993); Lu et al., *J. Chromatogr.* A680: 497 (1994); Lu et al., *J. Chromatogr.* A680: 503 (1994); Fung et al., *Anal. Chem.* 67: 1913 (1995); Zhang et al., *Anal. Chem.* 67: 4589 (1995); Carrilho et al., *Anal. Chem.* 68: 3305 (1996); and Kim et al., *J. Chromatogr.* 781: 315 (1997)), rapid and precise DNA typing and sizing (Baba et al., *Electrophoresis* 16: 1437 (1995); Noble, *Anal. Chem.* 67: 613A (1995); Zhang et al., *Anal. Chem.* 68: 2927 (1996); Isenberg et al., *Electrophoresis* 17: 1505 (1996); Zhang et al., *J. Chromatgor.* A768: 135 (1997); Butler et al., *Electrophoresis* 16: 974 (1995); and Wang et al., *Anal. Chem.* 67: 1197 (1995)), single-base mutation analysis (Marino et al., *Electrophoresis* 17: 1499 (1996); Arakawa et al., *J. Chromatogr.*: A664: 89 (1994); Hebenbrock et al., *Electrophoresis* 16: 1429 (1995); Kuypers et al., *J. Chromatogr.*: B 675: 205 (1996); Cheng et al., *J. Cap. Elec.* 2: 24(1995); and Ren et al., *Anal. Biochem.* 245: 9 (1997)) and the analysis of disease causing genes (Lu et al., *Nature* 368: 269 (1994); Felmlee et al., *J. Cap. Elec.* 2: 125 (1995); Gelfi et al., *BioTechniques* 19: 254 (1995); and Grossman et al., *Nucleic Acids Res.* 22: 4527 (1994)). In particular, capillary array electrophoresis, along with other micro-fabricated devices (Ueno et al., *Anal. Chem.* 66: 1424 (1994); Takahashi et al., *Anal. Chem.* 66: 1021 (1994); and Anazawa et al., *Anal. Chem.* 68: 2699(1996))are promising methods for the purpose of achieving high-throughput DNA analysis. In this regard, single capillaries have been utilized for DNA analysis (Guttman et al. (1992), supra).

The conventional protocol for DNA analysis calls for labeling with radionuclides or fluorescent tags before, during or after size-based separation in slab gel electrophoresis or in capillary gel electrophoresis (CGE). This derivatization process involves expensive reagents and raises safety concerns for the operator and for waste disposal because of the toxic nature of these labeling reagents.

The present invention can be applied to genetic typing and diagnosis based simply on UV absorption detection. The additive contribution of each base pair to the total absorption signal provides adequate detection sensitivity for analyzing most PCR products. Not only is the u ef specialized and potentially toxic fluorescent labels eliminated, but also the complexity and cost of the instrumentation are greatly reduced. The DNA analysis protocols can, therefore, be designed to take advantage of high-throughput capillary array gel electrophoresis and simple UV absorption detection, based on the inherent spectral properties of the DNA bases. UV absorption detection of DNA products reduces the cost of analysis, since it does not require labeling.

Similarly, peptide mapping represents one of the most powerful and successful tools available for the characterization of proteins (Garnick et al., *Anal. Chem.* 60: 2546–2557 (1988); Borman, *Anal. Chem.* 59: 969A–973A (1987)). Although less informative than protein sequencing, it allows rapid analysis with simple instrumentation. In peptide mapping, a sample protein is selectively cleaved by enzymes or by chemical digestion (Tarr et al., *Anal. Biochem.* 131: 99–107 (1983); Dong, *Advances in Chromatography* 32: 22–51, Marcel Dekker, Inc.: New York (1992); Geisow et al., *Biochem. J.* 161: 619–625 (1977); and Ward et al., *J. Chromatogr.* 519: 199–216 (1990)). The peptide map then serves as a unique fingerprint of the protein and can accurately reveal very subtle differences among individual variants. Trypsin is by far the most widely used proteolytic enzyme in peptide mapping. Its desirable feaares are that cleavage at the C-terminal side of lysine and arginine is generally quantitative under proper conditions and that trypsin tolerates concentrations of urea as high as 4 M (Dong (1992), supra). The disadvantage is that the fragments formed may be too small, averaging 7–12 amino acid residues, resulting in very complex tryptic maps. After tryptic digestion, the digest is typically analyzed by various methods, such as slab gel electrophoresis (Cleveland et al., *J. Biol. Chem.* 252: 1102–1106 (1977)), thin layer chromatography (TLC) (Stephens, *Anal. Biochem.* 84: 116–126 (1978)), HPLC (Hancock et al., *Anal. Biochem.* 89: 203–212 (1978); Cox et al., *Anal. Biochem.* 154: 345–352 (1986); Fullmer et al., *J. Biol. Chem.* 254: 7208–7212 (1979); Vensel et al., *J. Chromatogr.* 266: 491–500 (1983); Leadbeater et al., *J. Chromatogr.* 397: 435–443 (1987); Dong et al., *J. Chromatogr.* 499: 125–139 (1990); and Hartman et al. *J. Chromatogr.* 360: 385–395 (1986), and capillary zone electrophoresis (CZE) (Jorgenson et al., *J. High Resolut. Chromatogr. Commun.* 4: 230–231 (1981); Cobb et al., *Anal. Chem.* 61: 2226–2231 (1989); Chang et al., *Anal. Chem.* 65: 2947–2951 (1993); Nashabeh et al., *J. Chromatogr.* 536: 3142 (1991); Ward et al., *J. Chromatogr.* 519: 199–216 (1990); Janini et al., *J. Chromatogr.* 848: 417–433 (1999); Frenz et al., *J. Chromatogr.* 480: 379–391 (1989); and Grossman et al., *Anal. Chem.* 61: 1186–1194 (1989)) to yield a peptide map. Gradient reversed-phase HPLC is the most common form of peptide mapping in use today (Leadbeater et al. (1987), supra; Dong et al., (1990), supra; and Hartman et al. (1986), supra).

In particular, CZE has received considerable attention as a complementary method to reversed-phase liquid chromatography in peptide mapping efforts (Jorgenson et al. (1981), supra; Cobb et al. (1989), supra; Chang et al. (1993), supra; Nashabeh et al. (1991), supra; Ward et al. (1990), supra; Janini et al. (1999), supra; Frenz et al. (1989), supra; and Grossman et al. (1989), supra). Separation of various peptides can be optimized through pH adjustments. Through the addition of micelle-forming surfactants to the running buffer, a dynamic partition mechanism (i.e., hydrophobicity) of peptide separation can also be established for the neutral fragments. Although CE is quite efficient and fast for aawyzing peptide fragments, the complete separation of peptides in a digest of high molecular mass proteins, for example, is not possible by using a single buffer condition. Unlike HPLC, the implementation of gradient separation in CE is not trivial (Whang et al., Anal. Chem. 64: 502–506 (1992); and Chang et al., J. Chromatogr. B 608: 65–72 (1992)).

Although these methods are useful for characterizing proteins, there are still other problems, such as the relatively large amount of sample required, long analysis time, and efficiency of the derivatization reaction Also, a typical map contains 20–150 peaks, all of which should ideally be totally resolved (Dong et al. (1992), supra). Therefore, a high degree of column resolution and system precision are required to reproduce accurately the maps, preferably starting with subnanomolar quantities.

The present invention enables a peptide map to be obtained that can serve as a unique fingerprint of the protein. Reliable high-throughput analyses can be performed, for example, based on multi-dimensional CE and a single prescribed experimental protocol.

Combinatorial screening also has attracted much attention recently because of its ability efficiently and reliably to zero in and identify the best solution to a chemical or biochemical question (Borman, C&E News, Mar. 8, 1999, pages 33–60). In chemical synthesis, optimization of the reaction yield can be achieved by simultaneously exploring all possible reaction conditions, catalysts and reagents. In drug discovery, all related structural variants of a given candidate can be tested against the target. However, screening must be comprehensive so that there is no chance of missing the best combination. This dictates having a large number of experiments to cover many parameters and to extend the range of each of thee parameters. High throughput is a requirement in order to produce a timely result. It is primarily because of the advances in high-throughput technologies and automation that combinatorial screening became practical. Still needed are general and rugged analytical methodologies that can keep up with the large number of reactions that can be performed in any given time. Another issue is miniaturization of the entire operation. This impacts the cost of reagents, proper disposal of solvents, space for manipulation and storage, etc.

Currently, there are several parallel assays for screening homogeneous catalysts. Modifications in V absorption (Wagner et al., Sicence 270: 1797–1800 (1995); Menger et al., J. Org. Che. 63: 7578–7579(1998)), fluorescence (Cooper et al., J. Am. Chem. Soc. 120: 9971–9972 (1998); Shaughnessy et al., J. Am. Chem. Soc. 121: 2123–2132 (1999)), color (Lavastre et al., Chem. Int. Ed. 38: 3163–3165 (1999)) or temperature (Taylor et al., Science 280: 267–270 (1998); Reetz et al., Angew. Chem. Int. Ed. 37: 2647–2650 (1999)) induced by the catalytic reactions are indicators of catalytic activity. In these approaches, although the relative activity of the catalyst is determined quicldy, no quantitative information about the overall yield or the regioselectivity and stereoselectivity of the process can be obtained. It is also nesary that the product exhibit very different measurable properties compared to the solvent or the reagents. Most of the time, secondary screening is necessary. Mass spectrometry (MS) (Orschel et al., Angew. Chem. Int. Ed. 38: 2791–2794 (1999)), which also has been widely used to screen catalysts, can provide selective detection. However, to address stereoselectivity, these procedures still tend to be laborious (Reetz et al., Angew Chem. Int. Ed. 38: 1758–1761 (1999)). So far, MS is still a serial, rather than a pael, approach, although the analysis time is reasonably short.

Separation-based techniques can solve the above problems. Serial methods, which include HPLC and CE, have been used to analyze asynunetric catalysis (Porte et al., J. Am. Chem. Soc. 120: 9180–9187 (1998); Ding et al., Angew. Chem. Int. Ed. 38: 497–501 (1999)) and alkylation reactions (Gaus et al., Biotech. & Bioeng. 1998/1999 61: 169–177). The throughput that can be achieved with serial separation schemes is low even with special techniques, such as sequential sample injection (Roche et al., Anal. Chem. 69: 99–104 (1997)) and sample multiplexing (Woodbury et al., Anal. Chem. 67: 885–890 (1995)). Multiplex HPLC is another interesting approach (Gong et al., Anal. Chem. 71: 4989–4996 (1999)), but achieving a high degree of multiplexing, such as 96 capillaries in capillary array electrophoresis (CAE), is not trivial. Thin-layer chromatography and gel clectrophoresis, on the other hand, are difficult to completely automate.

A highly successfl format for combinatorial screening is that of DNA chips (Southern, Electrophoresis 16: 1539–1542 (1995); Chee et al., Science 274: 610–614 (1996); and Winzeler et al., Science 281: 1194–1197 (1998)). A comprehensive set of oligonucleotides immobilized within a snall area is used to identify specific target sequences by hybridization. Oligonucleotide chips also have been used to develop aptamers that exhibit specific protein-nucleotide binding (Weiss et al., J. Virol. 71: 8790–8797 (1997)). Such heterogeneous screening assays have benefited from sensitive detection based on laser-induced fluorescence (LIF), either by selective labeling or by selective quenching. For homogeneous assays, the 96-well microtiter plate is a popular format. Fluidic operations, plate readers and autosamplers to interface to stanard analytical instruments have been developed for this format. When there is a color (absorption) change or fluorescence change, detection and quantitation is straightforward. In many situations, however, the reaction mixture is complex and some degree of separation or purification is needed before measurement. Multiple liquid chromatographs or single instruments with several columns can in principle be used for analysis of the reaction mixtures. Still, much higher throughput and much smaller sample sizes, which means much smaller amounts of reagents, are desirable. The present invention enables such higher throughput and smaller sample sizes and does not require the species of interest to be fluorescent.

BRIEF SUMMARY OF THE INVENON

The present invention provides a method of analyzing multiple samples simultaneously by absorption detection. The method comprises:

(i) providing a planar array of multiple containers each of which contains a sample comprising at least one absorbing speies, (ii) irradiating the planar array of multiple containers with a light source comprising or consisting essentially of at least one wavelength of light that is absorbed by one or more of the absorbing species, the absorption of which is to be measured, and (iii) detecting absorption of light by one or more of the absorbing species with a detection means that is in line with the light source and is positioned in line with and parallel to the planar array of multiple containers at a distance of at least about 10 times a cross-sectional distance of a container in the planar array of multiple containers measured orthogonally to the plane of the planar array of multiple containers. The detection of absorbtion of light by a sample in the planar array of multiple containers indicates the presence of an absorbing species in the sample. The method can frther comprise:

(iv) measuring the amount of absorption of light detected in (iii) for an absorbing species in a sample. The measurement of the amount of absorption of light detected in (iii) indicates the amount of the absorbing species in the sample.

Also provided by the present invention is a system for use in the above method. The system comprises:

(i) a light source comprising or consisting essentially of at least one wavelength of light that is absorbed by one or more absorbing species, the absorption of which is to be detected, (ii) a planar array of multiple containers, into each of which can be placed a sample comprising at least one absorbing species, and (iii) a detection means that is in line with the light source and is positioned in line with and parallel to the planar array of multiple containers at a distance of at least about 10 times a crossectional distance of a container in the planar array of multiple containers measured orthogonally to the plane of the planar array of multiple containers.

BRIEF DESCRIPTION OF THE FIGURES

FIG. 11 represents the peptide maps of three variants of bovine β-lactoglobulin [SEQ ID NO: 1].

FIG. 15B at pH 8.1; FIG. 15C at pH 5.0; and FIG. 15D at pH 2.5) for CZE using a single capillary after tryptic digestion.

DETAILED DESCRIPTION OF THE INVENTION

Figure 1:
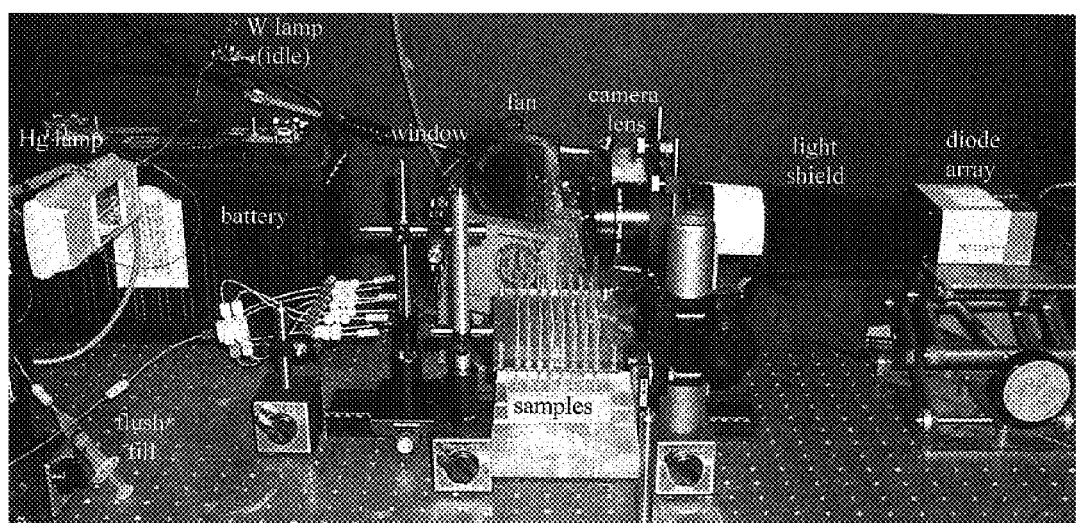
FIG. 1 is a diagram of a system for use in the present inventive method.

The present invention provides a method of analyzing multiple samples simultaneously by absorption detection. The present invention utilizes an integrated approach toward achieving automation, high speed, high accuracy and low cost, such as in the context of multiplexed electrophoresis. The method can be used, for example, in multicapillary array zone electrophoresis, micellar electrokinetic chromatography, capillary electrochromatography, and capillary gel electrophoresis. When a multicapillary array is used, as much as 100 times, or even 1,000 times or greater, higher analysis throughput can be achieved when compared to conventional single-capillary electrophoresis. The system is at least about 100-fold more sensitive than the system of Wu and Pawliszyn.

The method comprises:

(i) providing a planar array of multiple containers, each of which contains a sample comprising at least one absorbing species, (ii) irradiating the planar array of multiple containers with a light source comprising or consisting essentially of at least one wavelength of light that is absorbed by one or more of the absorbing species, the absorption of which is to be detected, and (iii) detecting absorption of light by the one or more absorbing species with a detection means that is in line with the light source and is positioned in line with and parallel to the planar array of multiple containers at a distance such that stray light exiting the planar array of multiple containers disperses prior to impinging upon the detection means. The amount of stray light falls off inversely as the square of the distance between the planar array and the detector increase. Thus, the light impinging upon the detection means is substantially only that which is transmitted through the multiple containers. In this manner, the intensity of the outputs from the planar array of multiple containers is the strongest and, therefore, the intensity of the outputs from the detection means is also the strongest, thereby making the determination of the intensity outputs from the detection means for each container in the planar array of multiple containers easy. The detection of absorption of light by a sample in the planar array of multiple containers indicates the presence of an absorbing species in the sample.

The method can further comprise (iv) measuring the amount of absorption of light detected in (iii) for an absorbing species in a sample. The measurement of the amount of absorption of light detected in (iii) indicates the amount of the absorbing species in the sample. Methods of measuring the amount of absorption of light are known in the art. Basically, one measures the intensity of light in the absence and presence of a sample. The logarithm of the ratio is the absorbance (Beer-Lambert law). Preferably, the distance between the planar array of multiple containers and the detection means is at least about 10 times, at which distance the stray light is less than about 1%, more preferably, at least about 100 times a cross-sectional distance of a container in the planar array of multiple containers measured orthogonally to the plane of the planar array of multiple containers.

The distance between the light source and the planar array of multiple containers is not critical to the practice of the present invention. However, the shorter the distance between the light source and the planar array of multiple containers, the more light will be received by the planar array of multiple containers. The greater the distance between the light source and the planar array of multiple containers, the more uniform will be the light received by the planar array of multiple containers. The more light that the planar array of multiple containers receives, the more sensitive will be the detection.

The position of the light source in relation to the planar array of multiple containers also is not critical to the practice of the present invention as long as the light source irradiates the planar array of multiple containers. Other considerations are as noted in the preceding paragraph.

Preferably, the distance between the planar array of multiple containers and the detection means is at least about 10 times, more preferably, at least about 100 times, a cross-sectional distance of a container in the planar array of multiple containers measured orthogonally to the plane of the planar array of multiple containers. Thus, the distance between the planar array of multiple containers and the detection means is preferably from about 1 cm to about 30 cm, more preferably from about 3 cm to about 30 cm, and most preferably from about 10 cm to about 30 cm. When cylindrical capillary tubes are used as the multiple containers, preferably the distance is from about 1 cm to about 30 cm, more preferably from about 3 cm to about 30 cm, and most preferably from about 10 cm to about 30 cm.

By "multiple containers" is meant at least three or more, preferably at least about 10, more preferably at least about 90, and desirably as many as can be accommodated by the system described herein. While the multiple containers can comprise any suitable containers, desirably the multiple containers allow the passage of light from the light source through the walls of the containers facing the light source, through the samples in the containers, and through the walls of the containers facing the detection means. Thus, the walls of the containers are desirably transparent, although, in some instances, the walls of the containers can be translucent. In this regard, it is not necessary for the entirety of the walls of the containers to allow the passage of light ftn the light source as described above as long as at least a portion of the walls of the containers allow the passage of light from the light source such that the samples in the containers are irradiated and the light that is not absorbed by the absorbing species in the samples is detectable by the detection means. Preferably, the multiple containers comprise cylindrical capillary tubes. Preferably, the planar array of multiple containers comprises at least about 10 capillary tubes, more preferably at least about 90 capillary tubes, such as 96 capillary tubes, and desirably as many as can be accommodated by the system described herein.

The planar array desirably further comprises at least one control container. However, if the light source is stable, a control container is not necessary.

In general, the containers used in the planar array should have smooth surfaces and uniformly thick walls and be made of a material that is traspent over the range of wavelengths of light absorbed by an absorbing species in a sample, the absorbance of which is to be detected or measured. Preferred materials for containers include, but are not limited to, plastics, quartz, fused silica (in particular for capillary tubes) and glass. The cross-section of a container is not critical to the present inventive method. However, the smaller the cross section of the container, the more useful is the container in highly multiplexed applications as a greater number of containers can be used in a smaller amount of space. Similarly, the thickness of the wall of the container is not critical to the present inventive method. The wall should be of sufficient thickness so as to maintain the structural integrity of the container, yet not so thick as to impede adversely the passage of light through the container. The shape of the container also is not critical to the present inventive method. The container can have any suitable shape. Desirably, the shape of the container is conducive to being closely packed and minimizes the generation of stray light by the container.

A cylindrical capillary tube is a preferred container for use in the context of the present invention. Capillary tubes are commnercially available from a number of sources, including Polymicro Technologies, Inc., Phoenix, Ariz. The capillary tube is preferably coated with a polymer, such as polyimide, so that it is mechanically stable. The coating must be removed in the region to be irradiated by the light source. An excimer laser can be used to remove the polymer coating.

Preferably, the multiple containers in the planar array are arranged substantially parallel to each other. Also preferably, the multiple containers in the planar array are also arranged substantially adjacent to each other. For example, when the multiple containers are capillary tubes, the capillary tubes are closely packed so as to be substantially contiguous along their parallel lengths, leaving essentially no space between adjacent capillaries. Substantially adjacent capillary tubes can be physically touching each other along all or a portion of their lengths, although slight inconsistencies in capillary wall diameter or other features of the array can prevent them ftom being in contact along their entire lengths. The planar array desirably is rigidly mounted to reduce flicker noise.

If a large amount of heat is generated during the method, particularly in the vicinity of the planar array of multiple containers, cooling should be employed to dissipate the heat. Excessive heat can lead to mechanical vibrations between adjacent containers in the planar array of multiple containers (e.g., such as in the case of closely packed capillary tubes), which, in turn, can lead to excess noise. A laminar flow of nitrogen gas, such as in parallel to the portion of the containers undergoing detection, can be used for cooling.

The detection means can comprise any suitable means of detecting absorption. Preferably, the detection means comprises a plurality of absorption detection elements, such as a plurality of photosensitive elements, which desirably are positioned in a linear array, although a two-dimensional image array detector can be used. Desirably, the detection means is parallel to and in line with the linear array of multiple containers. The detection means desirably is rigidly mounted to reduce flicker noise. In this regard, the relative positions of cell components used in the system must be fixed.

Preferably, a linear photodiode array (PDA) is used. Desirably, the PDA incorporates a linear image sensor chip, a driver/amplifier circuit and a temperature controller, which desirably thennoelectrically cools the sensor chip to a tempeatre from about 0° C. to about −40° C. Lowering the tempture lowers the dark count and minimizes the temperature drift, thus enabling reliable measurements to be made over a wide dynamic range. The driver/amplifier circuit is desirably interfaced to a computer via an I/O board, which preferably also serves as a pulse generator to provide a master clock pulse and a master start pulse, which are required by the linear image sensor. The PDA records the image linearly—not tw dimensionally. Preferably, the data acquired are written directly to the hard disk in real time. Also, preferably, the signals from up to at least about ten elements of the PDA are displayed in real time.

Alternatively, a charge-coupled device (CCD) or a charge-injection device (CID) can be used. However, the CCD records in two dimensions, which is less efficient, requiring more computer memory, is slower, requires every location to be read (not a single line like PDA). Furthermore, whereas a CCD has only 100,000 electrons in each location, each element in a PDA can store 59 million electrons per pixel per location; thus, given that detection sensitivity is related to the square root of the number of electrons that can be detected, a PDA is orders of magnitude more sensitive than a CCD.

Preferably, the PDA comprises linearly aligned pixels, in which case each container in the planar array of multiple containers desirably is a capillary tube and each capillary tube preferably is optically coupled to less taan about ten pixels, more preferably from about 7 to about 9 pixels, some of which are coupled to the walls of the capillary and some of which are coupled to any space between the walls of adjacent capillaries and at least one of which is coupled to the lumen of the capillary. Thus, the stray light caused by the walls of a capillary is dispersed prior to striking the pixels and/or is confined to the pixels coupled to the side walls and generally does not affect the signal produced by the pixel coupled to the lumen of the capillary. While the ratio of capillaries to optically coupled pixels is preferably less than about 1:10, more preferably from about 1:7 to about 1:9, the ratio of capillaries to optically coupled pixels need not be an integer ratio.

If the detection means is a PDA comprising linearly aligned pixels, step (iii) of the method can comprise selecting one pixel from the middle group of pixels, i.e., the pixel detecting the strongest light intensity and using that pixel to detect the absorbance by the target species. When more than one pixel is optically coupled to the interior of a container, it is desirable to select only one to analyze to and to disregard the others. Alternatively, only one pixel can be optically coupled to each container, obviating the need to make a pixel selection, although this is less preferred because of the need for critical optical aligmnent. In large arrays with many containers, which desirably are capillary tubes, it can be practical to use a higher ratio of pixels to containers so as to accommodate inconsistencies and variations in packing of the containers, and the width of the walls of the containers; etc. Where higher ratios of pixels to capillaries are used, more than one pixel can be optically coupled to the lumen of a container. Each pixel that is coupled to the lumen of a container will produce a signal having an intensity directly proportional to the intensity of light detected. The pixel producing the signal having the greaest intensity, i.e., the "brightest" pixel, is advantageously selected.

Selection of the appropriate pixel from those that are optically coupled to the interior portion of a container can be conveniently done by way of a calibration step. Thus, the method of the present invention can further comprise a calibration step, which is performed prior to introducing the samples into the containers. Alternatively, every nth capillary, e.g., every 10th capillary, includes a control or blank sample, i.e., a control container as indicated above.

The method can be carried out at ambient temperature, such as room temperature, such as from about 20° C. to about 30° C., or as low as 0° C. or as high as 80° C. However, if the method employs a PDA as the detection means as is preferred, desirably the PDA has its own cooler for operation at subzero tenperatures, such as from about 0° C. to about −40° C.

The light source preferably comprises or consists essentially of a wavelength in the range from about 180 nm to about 1500 nm. Examples of suitable light sources include mercury (for ultraviolet (UV) light absorption), tungsten (for visible light absorption), iodine (for UV light absorption), zinc (for TV light absorption), cadmium (for UV light absorption), xenon (for UV light absorption), deuterium (for visible light absorption), and the like. Desirably, the light source comprises or consists essentially of a wavelength of light that will be absorbed by an absorbing species, the absorption of which is to be detected. Which wavelength of light will be absorbed by an absorbing species of interest, i.e., an absorbing species, the absorption of which is to be detected or measured in accordance with the present invention, can be determined using a standard absorption spectrometer. Alternatively, spectroscopic tables that provide such information are available in the art, such as through the National Institute of Science and Technology (NIST). Desirably, a maximally absorbed wavelength of light is selected for a given absorbing species to be detected or measured such that smaller amounts of the absorbing species can be detected. Generally, the light source provides light impinging on the planar array of multiple containers orthogonal to the plane in which the planar array of multiple containers. The light source can be a point source. Also preferably, the light source has a power output of about 0.5 mW to about 50 mW. The light source can be AC or DC, although DC is preferred. Any flicker noise from the light source can be eliminated by using a double beam of light.

The pathlength of light is critical to the sensitivity of the present inventive method. The longer the pathlength of light absorbed by a sample in a container, the larger the signal for the sample. This is in accordance with Beer's Law, which states that absorbance=constant (which is the spectral characteristic of an absorbing species in a sample in a contaener, the absorbance of which is to be detected or measured)× pathlength of the light×concentration of the absorbing species in a sample in a container. A high constant and a long pathlength are desired.

An optical filter desirably is positioned between the planar array of multiple contaners and the detection means. The optical filter selects at least one wavelength of light from the light source that is absorbed by an absorbing species, the absorption of which is to be detected. While an optical filter can be positioned between the light source and the planar array of multiple containers in addition to, or as an alternative to, an optical filter positioned between the planar array of multiple containers and the detection means, the placement of a single optical filter between the light source and the planar array of multiple containers is disadvantageous inasmuch as it does not block the subsequent fluorescence by the sample from reaching the detection means. In contrast, the placement of an optical filter between the planar array of multiple containers and the detection means blocks sample fluorescence from reaching the detection means.

A flat-field lens also desirably is positioned between the planar array of multiple containers and the detection means. The flat-field lens couples light that is not absorbed by the one or more absorbing species in each sample in the planar array of multiple containers with the detection means. While a lens that is not a flat-field lens can be used in the context of the present invention, it is disadvantageous inasmuch as it does not image the entire field evenly. Consequently, the edges of the field are distorted and the absorption of the containers in the planar array of multiple containers positioned at the edges of the field of the lens cannot be detected or measured. The lens inverts the image of the planar array of multiple containers onto the face of the detection means, which preferably is a PDA.

Desirably, the coupling of light by the flat-field lens is shielded from the light source. This way, only the light from the lens is focused on the detection means.

The detection limit of rhodamine 6G for each capillary in a planar array of multiple capillaries is about $1.8 \times 10^{-8}$ M. The cross-talk between adjacent capillaries in a planar array of multiple capillaries is less than about 0.2%.

While the sample can be introduced into each capillary tube in a planar array of multiple capillaries by any suitable method, preferably the sample is introduced into the capillary tube by pressure, gravity, vacuum, capillary or electrophoretic action.

A beam expander can be positioned between the light source and the planar array of multiple containers. The beam expander can alter the focused line of the light source so as to irradiate more effectively the multiple containers. The beam, optionally, can be altered or redirected, as with a mirror, filter or lens, prior to contacting the array.

A collimating focusing lens can be positioned between the light source and the planar array of multiple containers.

The above components are placed to eliminate substantially and, desirably, completely, stray light. There are two kinds of stray light. One kind of stray light is the glare that results from the containers having side walls and interior lumens. The other kind of stray light is that which is due to the presence of other containers in the planary array of multiple containers. This kind of stray light is referred to as "cross talk." Cross talk essentially is the glare from other containers. Thus, there needs to be sufficient distance between the sample and the flat-field lens to eliminate substantially and, desirably completely, the two kinds of glare. A distance of at least about $1/r^2$, i.e., the rate of decrease of stry light as the distance r increases, or $1/d$, in which r=radius and d=diameter, will eliminate most of the glare from the containers. Glare can be assessed by measuring a totally absorbing material in a container; if there is any light that is detected, that light is due to glare.

Preferably, raw data sets are extracted into single-diode electropherograms and analyzed by converting the transmitted light intensities collected at the PDA to absorbance values. Root-mean-squared noise in the electropherograms is obtained using a section of baseline near one of the analyte peaks. A preferred manner of collecting and analyzing data obtained in accordance with the present invention is set forth in Example 1.

Mathematical smoothing can be used to reduce the noise significantly, without distorting the signal. See, for exanple, Example 1. In this regard, as high a data acquisition rate as possible should be employed to provide more data points for smoothing. Boxcar smoothing, such as 25 point boxcar smoothing, is a preferred method of mathematical smoothing.

In view of the above, the present invention further provides a system for use in the above method, preferred embodiments of which are exemplified in the Examples and FIG. 1 set forth herein. The system comprises:

(i) a light source comprising or consisting essentially of at least one wavelength of light that is absorbed by one or more absorbing species, the absorption of which is to be deteted, (ii) a planar array of multiple containers, into each of which can be placed a sample comprising at least one absorbing species, and (iii) a detection means that is in line with the light source and is positioned in line with and parallel to the planar array of multiple containers at a distance such that stray light exiting the planar array of multiple containers disperses prior to impinging upon the detection means. Thus, the light impinging upon the detection means is substantially only that which is transmitted through the multiple containers. In this manner, the intensity of the outputs from the planar array of multiple containers is the strongest and, therefore, the intensity of the outputs from the detection means is also the strongest, thereby making the determination of the intensity outputs from the detection means for each container in the planar array of multiple containers easy. Preferably, the distance is at least about 10 times, more preferably, at least about 100 times, a cross-sectional distance of a container in the planar array of multiple containers measured orthogonally to the plane of the planar array of multiple containers. The detection of absorption of light by a sample in the planar array of multiple containers indicates the presence of an absorbing species in the sample.

As indicated above, the distance between the light source and the planar array of multiple containers is not critical to the practice of the present invention. However, the shorter the distance between the light source and the planar array of multiple containers, the more light will be received by the planar array of multiple containers. The greater the distanc between the light source and the planar array of multiple containers, the more uniform will be the light received by the planar array of multiple containers. The more light that the planar array of multiple containers receives, the more sensitive will be the detection.

The position of the light source in relation to the planar array of multiple containers also is not critical to the practice of the present invention as long as the light source irradiates the planar array of multiple containers Other considerations are as noted in the preceding paragraph.

Preferably, the distance between the planar array of multiple containers and the detection means is at least about 10 times, more preferably, at least about 100 times, a cross-sectional distance of a container in the planar array of multiple containers measured orthogonally to the plane of te planar array of multiple containers. Thus, the distance between the planar array of multiple containers and the detection means is preferably from about 1 cm to about 30 cm, more preferably from about 3 cm to about 30 cm, and most preferably from about 10 cm to about 30 cm. When capillary tubes are used as the multiple containers, preferably the distance is from about 1 cm to about 30 cm, more preferably from about 3 cm to about 30 cm. and most preferably from about 10 cm to about 30 cm.

By "multiple container" is meant at least three or more, preferably at least about 10, more preferably at least about 90, and desirably as many as can be accommodated by the system described herein. While the multiple containers can comprise any suitable containers, desirably the multiple containers allow the passage of light from the light source through the walls of the containers facing the light source, through the samples in the containers, and through the walls of the containers facing the detection means. Thus, the walls of the containers are desirably transparent, although, in some instances, the walls of the containers can be translucent. In this regard, it is not neces y for the entirety of the walls of the containers to allow the passage of light from the light source as described above as long as at least a portion of the walls of the containers allow the passage of light from the light source such that the samples in the containers are irradiated and the light that is not absorbed by the absorbing species in the samples is detectable by the detection means. Preferably, the multiple containers comprises cylindrical capillary tubes. If cylindrical capillary tubes are used, preferably the distance between the detection means and the planar array of multiple containers is at least about 10 times, more preferably at least about 100 times, the diameter of a capillary tube. Preferably, the planar array of multiple containers comprises at least about 10 cylindrical capillary tubes, more preferably at least about 90 cylindrical capillary tubes, such as 96 cylindrical capillary tubes, and desirably as many as can be accommodated by the system described herein.

The planar array desirably further comprises at least one control container. However, if the light source is stable, a control container is not necessary.

In general, the containers used in the planar array should have smooth surfaces, uniformly thick walls, and be made of a material that is transparmnt over the range of wavelengths of light absorbed by an absorbing species in a sample, the absorbance of which is to be detected ormeasured. Preferred materials fbr containers include, but are not limited to, quartz, fused silica (in particular for capillary tubes) and glass. The cross-section of a container is not critical to the present inventive method. However, the smaller the cross section of the container, the more usefid is the container in highly multiplexed applications as a greater number of containers can be used in a smaller amount of space. Similarly, the thickness of the wall of the container is not critical to the present inventive method. The wall should be of sufficient thickness so as to maintain the structual integrity of the container, yet not so thick as to impede adversely the passage of light through the container. The shape of the container also is not critical to the present inventive method. The container can have any suitable shape. Desirably, the shape of the container is conducive to being closely packed and minimizes the generation of stray light by the container.

A capillary tube is a preferred container for use in the context of the present invention. Capillary tubes are commercially available from a number of sources, including Polymicro Technologies, Inc. The capillary tube is preferably coated with a polymer, such as polyimride, so that it is mechanically stable. The coating must be removed in the region to be irradiated by the light source. An excimer laser can be used to remove the polymer coating.

Preferably, the multiple containers in the planar array are arranged substantially parallel to each other. Also preferably, the multiple containers in the planar array are also arranged substantially adjacent to each other. For example, when the multiple containers are capillary tubes, the capillary tubes are closely packed so as to be substantially contiguous along their parallel lengths, leaving essentially no space between adjacent capillaries. Substantially adjacent capillary tubes can be physically touching each other along all or a portion of their lengths, although slight inconsistencies in capillary wall diameter or other features of the array can prevent them from being in contact along their entire lengths. The planar array desirably is rigidly mounted to reducere flicker noise.

If a large amount of beat is generated during use of the system, particularly in the vicinity of the planar array of multiple containers, the system desirably fiurther comprises a cooling means. Excessive heat can lead to mechanical vibrations between adjacent containers in the planar array of multiple containers (e.g., such as in the case of closely packed capillary tubes), which, in turn, can lead to excess noise. A laminar flow of nitrogen gas, such as in parallel to the portion of the containers undergoing detection, can be used.

The detection means can comprise any suitable means of detecting absorption. Preferably, the detection means comprises a plurlity of absorption detection elements, such as a plurality of photosensitive elements, which desirably are positioned in a linear array, although a two-dimensional image array detector can be used. Desirably, the detection means is parllel to and in line with the linear array of multiple containers. The detection means desirably is rigidly mounted to reduce flicker noise.

Preferably, a linear photodiode array (PDA) is used. Desirably, the PDA incorporates a linear image sensor chip, a driver/amplifier circuit and a temperature controller, which desirably thermoelectrically cools the sensor chip to a temperature from about 0° C. to about −40° C. Lowering the temperature lowers the dark count and minimizes the temperature drift, thus enabling reliable measurements to be made over a wide dynamic range. The driver/amplifier circuit is desirably interfaced to a computer via an I/O board, which preferably also serves as a pulse generator to provide a maaster clock pulse and a master start pulse, which are required by the linear image sensor. The PDA records the image linearly—not two-dimensionally Preferably, the data acquired are written directly to the hard disk in real time. Also, preferably, the signals from up to at least about ten elements of the PDA are displayed in real time.

Alternatively, a charge-coupled device (CCD) or a charge-injection device (CID) can be used. However, the CCD records in two dimensions, which is less efficient, requiring more computer memory, is slower, requires every location to be read (not a single line like PDA), and has a reduced electron capacity. Futhermore, whereas a CCD has only 100,000 electrons in each location, each element in a PDA can store 59 million electrons per pixel per location; thus, given that detection sensitivity is related to the square root of the nunber of electrons that can be detected, a PDA is orders of magnitude more sensitive than a CCD.

Preferably, the PDA comprises linely aligned pixels, in which case each container in the planar array of multiple containers desirably is a capillary tube and each capillary tube preferably is optically coupled to less than about ten pixels, more preferably from about 7 to about 9 pixels, some of which are coupled to the walls of the capillary and some of which are coupled to any space between the walls of adjacent capillaries and at least one of which is coupled to the lumen of the capillary. Thus, the stray light caused by the walls of a capillary is dispersed prior to striking the pixels and/or is confined to the pixels coupled to the side walls and generally does not affect the signal produced by the pixel coupled to the lumen of the capillary. While the ratio of capillaries to optically coupled pixels is preferably less than about 1:1 0, more preferably from about 1:7 to about 1:9, the ratio of capillaries to optically coupled pixels need not be an integer ratio. Optical coupling of the capillaries and the pixels in this manner renders the system extremely stable.

Given that noise will ultimately determine the minimum baseline fluctuation level and, thus, the limit of detection (LOD) of the system, as explained in Example 1, it is desirable to hive as high a photon count as possible. Preferably, at least about 300,000, more preferably, at least about 3 million, and most preferably, at least about 30 million photons are used. In addition, so as to allow for baseline drift due to uncontrollable variables over the period of data acquisition, the diodes preferably are only 85–90% saturated.

The light source preferably comprises or consists essentially of a wavelength in the range from about 180 nm to about 1500 nm Examples of suitable light sources include mercury, tungsten, iodine, zinc, cadmium, xenon, deuterium, and the like. Desirably, the light source comprises or consists essentially of a wavelength of light that will be absorbed by an absorbing species, the absorption of which is to be detected. Which wavelength of light will be absorbed by an absorbing species of interest, i.e., an absorbing species, the absorption of which is to be detected or measured in accordance with the present invention, can be determined using a standard absorption spectrometer. Alternatively, spectroscopic tables that provide such information are available in the art, such as through NIST. Desirably, a maximally absorbed wavelength of light is selected for a given absorbing species to be detected or measured such that smaller amounts of the absorbing species can be detected. Generally, the light source provides light impinging on the planar array of multiple containers orthogonal to the plane in which the planar array of multiple containers. The light source can be a point source. Also preferably, the light source has a power output of about 0.5 mW to about 50 mW. The light source can be AC or DC, although DC is preferred. Any flicker noise from the light source can be eliminated by using a double beam of light.

Desirably, an optical filter is positioned between the planar array of multiple containers and the detection means. The optical filter selects at least one wavelength of light from the light source that is absorbed by an absorbing species, the absorption of which is to be detected. While an optical filter can be positioned between the light source and the planar array of multiple containers in addition to, or as an alternative to, an optical filter positioned between the planar array of multiple containers and the detection means, the placement of a single optical filter between the light source and the planar array of multiple containers is disadvantageous inasmuch as it does not block the subsequent fluorescence by the sample from reaching the detection means. In contrast, the placement of an optical filter between the planar array of multiple containers and the detection means blocks sample fluorescence from reaching the detection means.

Also desirably, a flat-field lens is positioned between the planar array of multiple containers and the detection means. The flat-field lens couples light that is not absorbed by the one or more absorbing species in each sample in the planar array of multiple containers with the detection means. While a lens that is not a flat-field lens can be used in the context of the present invention, it is disadvantageous inasmuch as it does not image the entire field evenly. Consequently, the edges of the field are distorted and the absorption of the containers in the planar array of multiple containers positioned at the edges of the field of the lens cannot be detected or measured. The lens inverts the image of the planar array of multiple containers onto the face of the detection means, which preferably is a PDA.

Preferably, the system further comprises a shield that shields the coupling of light by the flat-field lens from the light source. This way, only the light from the lens is focused on the detection means.

The detection limit for rhodamine 6G for each capillary in a planar array of capillary tubes in the system is about $1.8 \times 10^{-8}$ M. The cross-talk between adjacent capillaries is less than about 0.2%.

If the system utilizes capillary tubes or the like, the system further comprises a means to introduce the sample into the capillary tube. Preferably the sample is introduced into the capillary tube by pressure, gravity, vacuum, capillary or electrophoretic action.

The system can further comprise a beam expander between the light source and the planar array of multiple containers. The beam expander can alter the focused line of the light source so as to irradiate more effectively the multiple containers. The beam, optionally, can be altered or redirected, as with a mirror, filter or lens, prior to contactng the array.

The system can fuirther comprise a collimating focusing lens between the light source and the planar array of multiple containers.

The above components are placed to elininate substantially and, desirably completely, stray light as described above. Thus, there needs to be sufficient distance between the sample and the flat-field lens to eliminate substantially and, desirably completely, the two kinds of glare. A distance of at least about $1/r^2$ or $1/d$, in which r=radius and d=diameter, will eliminate most of the glare from the containers.

Desirably, the above components are collectively placed in a light-tight construct, such as a metal box attached to an optical table. Also, desirably, the components are centered above the optical table.

EXAMPLES

The present invention is further demonstrated by way of the following examples, which serve to illustrate the present invention but are not intended to limit its scope in any way.

Fluorescein (F), rhodaraine 6G, 5(6)-carboxyfluorescein (5CF, 6CF), β-lactoglobulin A and B (BLGA and BLGB), L-1-tosylamide-2-phenylethyl chloromethyl ketone (TPCK)-treated trypsin, CHES (2[N-cyclohexylamino] ethane-sulfonic acid), tricine (N-tris[hydroxymethyl] methylglycine), Trizma®. Base (tris[hydroxymethyl] aminomethane), ammonium acetate, $CaCl_2$, poly (vinylpyrrolidone) (PVP), sodium pyruvate (99+%), β-nicotinamine adenine dinucleotide, reduced form (β-NADH), L-lactate dehydrogenase (LDH-5($M_4$) 98+% isoenzyme suspension in 2.1 M $(NH_4)_2SO_4$), and sodium dodecyl sulfate (SDS) were purchased from Sigma Chemical Co. (St Louis, Mo.). Both of the solutions of β-$NAD^+$ and β-NADH were freshly prepared and kept in a refrigerator before the experiment. The NADH solution was covered by black tape to prevent exposure to light. Tween 20 was purchased from Aldrich Chemical Co. (Milwaukee, Wis.). 2,7-diacetate,dichloro-fluorescein (DADCF) was obtained from Acros (Fair Lawn, N.J.). Ethidium bromide (EtBr) was obtained from Molecular Probes, Inc. (Eugene, Oreg.). 50-bp and 100-bp DNA ladders were purchased from Life Technologies (Gaithersburg, Md.). The sample solutions for CZE were prepared by dissolving the appropriate amounts of these fluoresceins in 1×TBE (0.089 M Tris, 0.089 M borate, and 0.002 M ethylene diamine tetruacetic acid (EDTA) in water) buffer with 0.2% (w/w) PVP. For the MEKC experiments, the analytes and buffer additives were purchased from Aldrich (Milwaukee, Wis.), J. T. Baker (Phillipsburg, N.J.) and Sigma Chemical Co. The running buffer was prepared by adding appropriate aliquots of 1.0 M HCl, 250 mM Brij-S stock solutions, acetonitrile and 2-propanol into water. The pH was adjusted to 2.4 using 0.1 M HCl or 0.1 M NaOH stock solution and confirmed by a pH meter. 1×TBE buffer was prepared by dissolving premied TBE buffer powder (Amresco, Solon, Ohio) in deionized water. The coating matrix used in Example 2 was made by dissolving 2% (w/v) of 1,300,000 MW PVP into tew buffer, shaking for 2 min and letting it stand for 1 h to get rid of bubbles. Poly(ethylene oxide) (PEO) was obtained from Aldrich Chemical (Milwaukee, Wis.). The sieving matrix used in Example 2 was made by dissolving 2% (w/v) 600,000 MW PEO into the buffer. The solution was stirred vigorously overnight until all the material was dissolved and no bubbles could be observed. All buffers for Example 3 were filtered through a Corning® Filter System, 0.22-μm cellulose acetate filters (Corning, N.Y.) or μStar LB™, 0.22-μm cellulose acetate non-pyrogenic filters (Coaster, Cambridge), and degassed prior to use. The water used to prepare solutions in Example 3 was deionized with a Milli-Q water purification system (Millipore, Worcester, Mass.). Bacteria-free 0.2 ml 96-well preloaded plates were obtained from Marsh Biomedical Products, Inc. (Rochester, N.Y.). Sodium phosphate monobasic ($NaH_2PO_4.H_2O$) was purchased from Fisher (Fair Lawn, N.J.). All water used in Example 4 was purified by a Millipore water purification system to make sure that there was no enzyme contaminiation.

Example 1

This example demonstrates a multiplexed capillary electrophoresis system that employs a single linear photodiode array detector.

Ninety six fused-silica capillaries (75 μm i.d., 150 pm o.d.; Polymicro Technologies, Phoenix, Ariz.) with 35 cm effective length and 55 cm total length were packed side by side. An excimer laser beam was used to burn off the polyimide coating in the same region of each capillary to provide a "window" for passage of light from a light source through a sample to be introduced into and contained within each capillary. At the ground, i.e., exit, end of the capillary array, the capillaries were bundled together to allow simultaneous buffer filling and rinsing. At the injection end, the capillary array was spread out and mounted onto a copper plate to form an 8×12 format with dimensions that fit into a 96-well microtiter plate for sample introduction. In addition, 96 goldcoated pins (Mill-Max Mfg. Corp., Oyster Bay, N.Y.) were located next to the capillary tips to serve as individual electrodes. Samples and buffer trays were moved and aligned under the capillary inlets. This way, the capillary array was never physically moved. A high-voltage DC power supply from Spellman (Plainview, N.Y.) provided power for electrophoresis. All 96 electrodes were connected to the same power supply.

A light source, an optical, i.e., interference, filter, a capillary array holder, a camera lens and a PDA detector were placed in a light-tight metal box attached to an optical table. All optical components were centered 12.6 cm above the optical table. As the light source, a 12-V tungsten lamp or a 254 ln hand-held merrrry lamp (model E-09816-02; Cole-Parmer, Vernon Hills, Ill.) was used for visible or ultraviolet absorption detection, respectively. A diagram of a system for use in the present inventive method is shown in FIG. 1. In the case of the tungsten lamp (with a filament length of 1.1 cm), the light was first expanded through a cylindrical lens to cover uniformly the "windows" of the entire array of capillary tubes, which had a combined width of 1.5 cm. The hand-held mercury lamp proved to have a long enough emission length (7 cm), thus no beam expander was needed for illuminating the entire array. The transmitted light from the capillary array passed through an interference filter (Oriel, Stamford, Conn.) and a quartz lens (Nikon, Melville, N.Y.; f.1.=105 mm; F#=4.5). The interference filter was employed to define the absorption wavelength. An inverted image of the capillary array, at a nominal tnagnification factor of 1.5, was created by the quartz lens on the face of the PDA. The PDA (model S5964, Hamamatsu, Bridgewater, N.J.) incorporated a linear image sensor chip, a driver/amplifier circuit and a temperature controller. The linear image sensor chip had 1,024 dodes, each of which was 25 μm in width and 2,500 μm in height. The temperature controller thermoelectrically cooled the sensor chip to 0° C. to lower the dark count and to minimize temperature drift, thus enabling reliable measurements to be made over a wide dynamic range. The built-in driver/amplifier circuit was interfaced to an IBM-compatible computer (233 MH: Pentium, Packard Bell) via a National Instrnent PCI E series multiftnction 16-bit I/O board. The I/O board also served as a pulse generator to provide a master clock pulse and a master start pulse required by the linear image sensor. All codes used to operate the PDA and to acquire the data were written in-house using National Instruments Labview 4.1 software (Austin, Tex.). The distance between the plane defined by the capillary array and the plane defined by the PDA detector elements was 30 cm.

A very large amount of data were generated for each CE run using the 1,024-element PDA detector. A run of one hour with a data acquisition rate of 10 Hz generated 70 Mb of data. All the data were, therefore, written directly to the hard disk in real time. Signals from up to ten elements of the PDA could be displayed in real time in the Labview program. Real-time monitoring of more pixels was limited by the video speed of our computer. The raw data sets were extracted into singlel-diode eclectropherogram data by another in-house Labview program. Data treatment and analysis were performed using Microsoft Excel 97 (Microsoft, Seattle, Wash.) and GRAMS/32 5.05 (Galactic Industries, Salem, N.H.). The transmitted light intensities collected at the PDA were converted to absorbance values using the tenth capillary (buffer solution only) as a continuous blank reference, i.e., a control. The root-mean-squared (rms) noise in all of the electropherograms was obtained using a section of baseline near one of the analyte peaks. This baseline section was of about the same width as the peaks of interest.

For the capillary zone electrophoresis experiments, the capillary array was first flushed with methanol and then water for clean up. Buffer (pH 8.0, 1×TBE with 0.2% (w/w) polyvinylpyrrolidone (PVP)) was filled into the capillary array while the injection end was immersed into a buffer tray. After buffer filling, the filling ends were immersed into a second buffer tray. The analytes were put into a 96-well microtiter sample plate (1 $\mu$l/well) and injected at the cathode for 6 sec at 11 kV (100 V/cm). The runnng voltage was also 11 kV. For the CE experiments, the capillaries were washed for 1 min with buffer between runs. For the MEKC experiments, the capillary array was first flushed with 0.1 M HCl and then water. The buffer additive used was Brij-S made by sulfonation of Brij-30 with chlorosulfonic acid (Ding et al., *Anal. Chem.* 70: 1859–1865 (1998)). The analytes were injected at the cathode for 3 sec at 10 kV and run at the same voltage.

Figure 2A:
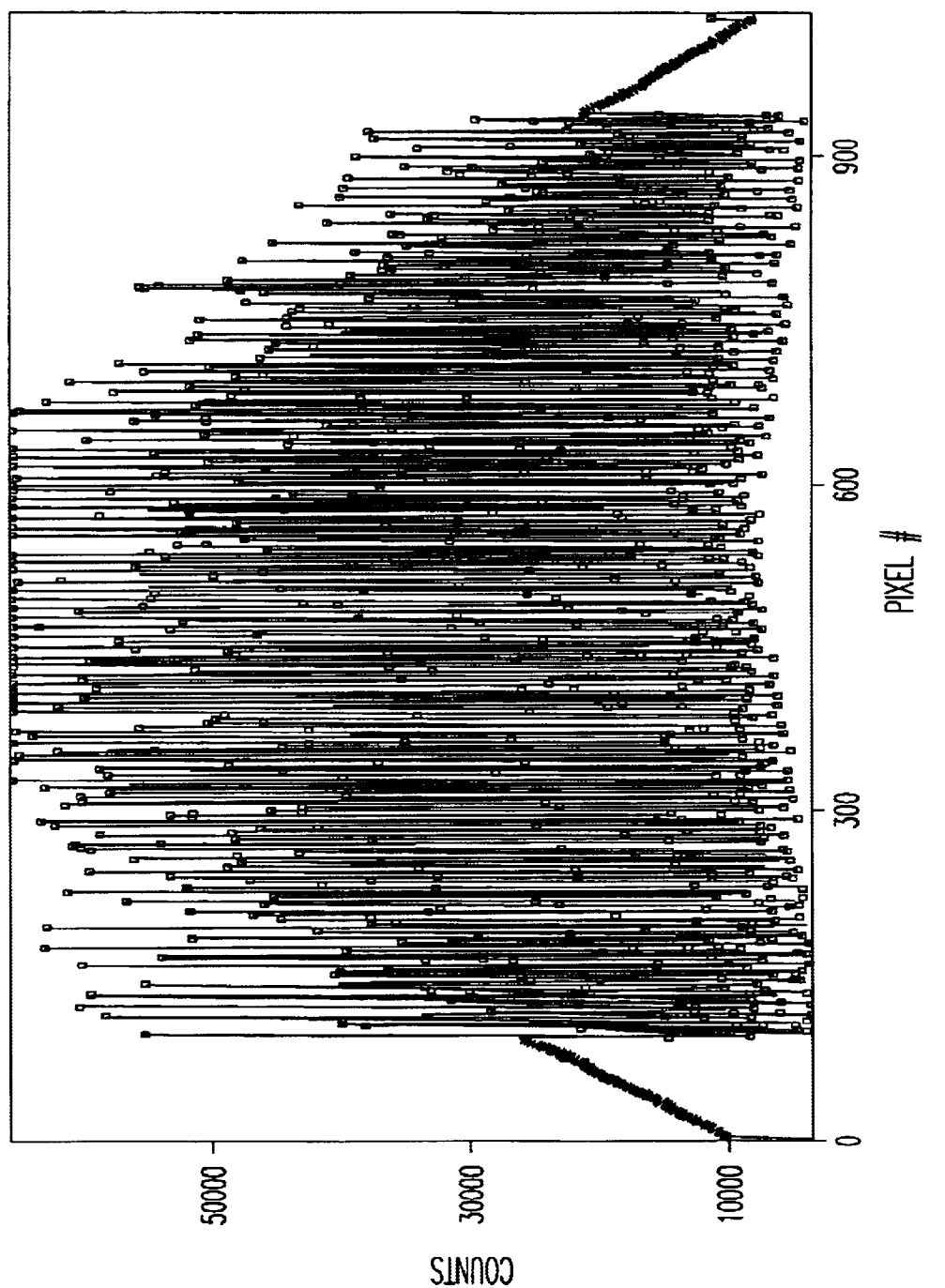
FIG. 2A is a graph of counts vs. pixel number.
Figure 2B:
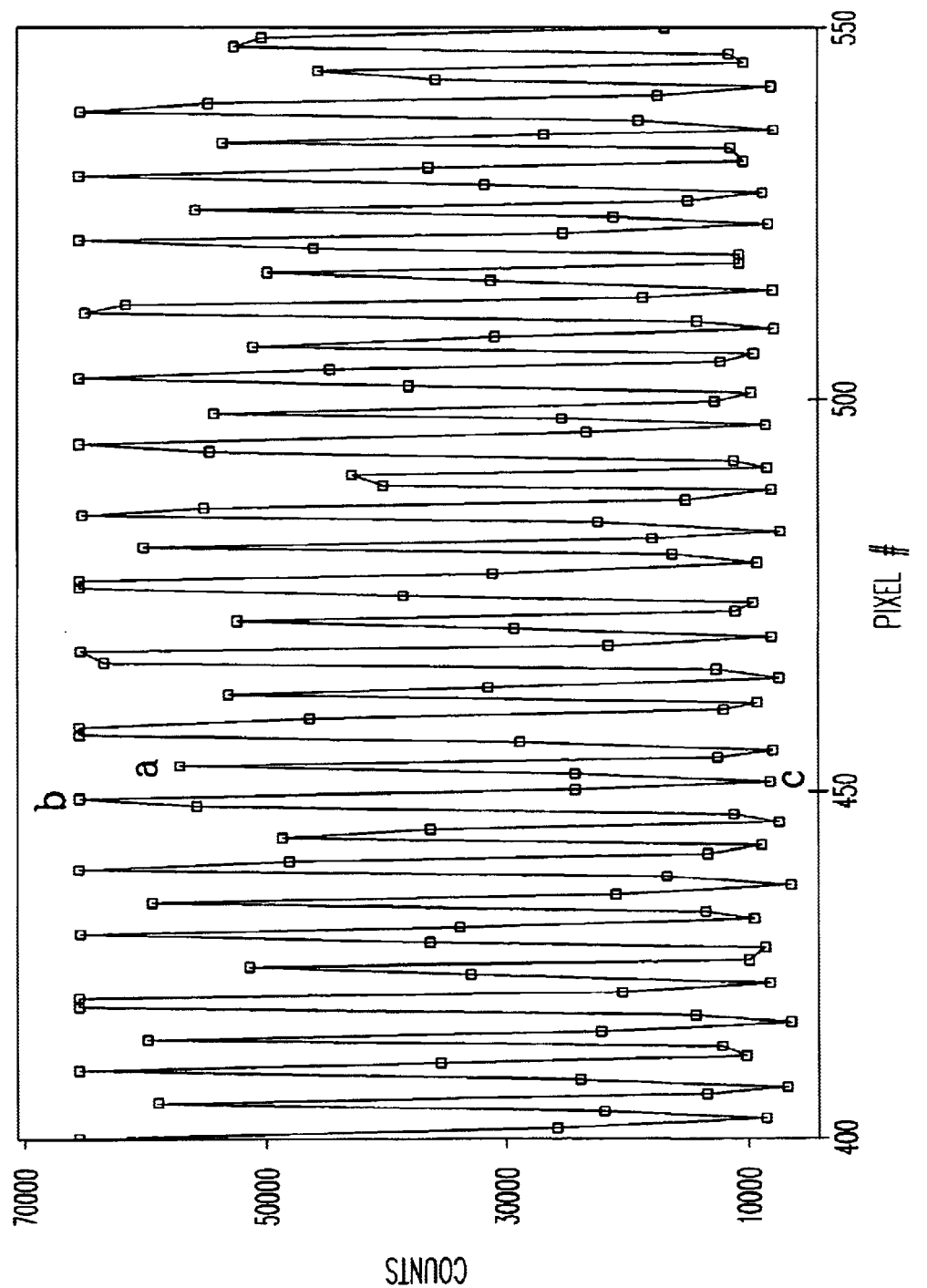
FIG. 2B is a graph of counts vs. pixel number.

A typical 96-capillary array image obtained using a tungsten lamp and the PDA is shown in FIG. 2A, which is a graph of counts vs. pixel number and represents the image on the PDA of the entire 96-capillary array. As can be seen in FIG. 2B, which is a graph of counts vs. pixel number and represents the image on the PDA of one region of the 96-capillary array, the center of each capillary corresponds to a 'peak' (a center peak represented by (a)) in the image. Between two adjacent capillaries, there is normally a spacing that also creates a transmission 'peak' (a spacing peak represented by (b)). These 'spacing peak' are usually a bit broader and have larger intensities (saturated in this case) than the 'center peak' in this imaging system, as shown in FIG. 2B. If the array packing is not even, two adjacent capillaries can overlap each other so that the 'spacing peak' between them is not observed. Including the spacing, each capillary was imaged upon 9–11 diodes in the PDA. The 96capillary array covered 912 pixels in total. As can be seen in FIG. 2B, between the 'center peak' and the 'spacing peak,' there is a 'valley' (represented by (c)), which corresponds to the wall of the capillary. When the capillary array image was well-focused onto the PDA, the intensities of these valleys became minimized. This feature was used to produce the best focusing. The diodes that corresponded to the center peaks were used as the absorption detectors for the corresponding capillaries. Their intensities are about 40% to 90% of the saturation value of the diodes. To maintain the relatively uniform intensity distribution over the capillary array, we found that the emission length of the light source should be at least two times larger than the width of the capillary array (1.5 cm). The hand-held mercury lamp (7-cm emission length) that was used as the UV light source was long enough for uniform illumination of the entire array. The tungsten lamp used as the visible light source, however, had only a 1-cm emission length, so a cylindrical lens needed to be added to magnify the light source to meet the illumination requirement. FIG. 2A shows a 2× variation in optical throughout from the center to the edge of the array. This means that the detection limit will vary by $\sqrt{2}$×across the array. The sensitivity (signal), however, will vary by 2× unless the intensities are first ratioed to the blank (buffer) and a log scale is used (Beer's Law). Given that the mercury lamp was placed very far from the array, the intensity distribution was, thus, much more uniform than that in FIG. 2A.

No mechanical slits were used to define the image. While the cylindrical capillaries do refractlight onto other diodes in the array, the distance from the array to the camera lens was maintained at a distance that was greater than the radius of curvature. Each diode receives a low leveel of stray light averaged over all capillaries. This sets the limit on the "valleys" in FIG. 2 but contributes negligibly to cross-talk. The rays of light crossing the diameters of the capillaries will travel straight and are properly imaged at the PDA. Sensitivity (absorption path length) is, thus, also optimized. Given that there are no mechanical slits and each capillary spans 9 pixels, the system is extremely stable. No realignment or refocusing is needed, although period checks of the alignment and focus, such as weekly checks, should be performed.

A clear understanding of the noise sources for the array detector is important, as the noise will ultimately determine the minimum baseline fluctuation level and, thus, the LOD of the system. Dark noise of the PDA can be attributed to dark current shot noise, diode reset noise and circuit noise, which are not dependent on the number of photoelectrons generated in the diodes (i.e., the input light intensity). According to the data given by the manufacturer, the dark noise ($s_d$) of the PDA is about 3,200 electrons at 0° C. Shot noise is generally defined as the combined noise associated with the random generation of photons from the excitation source and the random generation of photoelectrons in the diode junction, and is equal to the square root of the number of photoelectrons counted in each diode, $(n_e)^{1/2}$. The total rms noise level(s) of the PDA in the absence of flicker noise (see below) can be expressed using the equation:

$$s = s_d + (n_e)^{1/2}. \tag{1}$$

Therefore, it is desirable to have as high a photon count as possible. The electron well capacity of a diode is generally proportional to the area of the sensing junction. A long but narrow diode will maximize the dynamic range and the spatial resolution (in one dimension) at the same time. This comes with an incr==in dark current such that cooling becomes mandatory.

For the PDA used in this work, the saturation charge for each diode is about 25 pC, or 156 million electrons. This is almost three times as high as the PDA used in previous work (Culbertson et al., *Anal. Chem.* 70: 2629–2638 (1998)). In real absorption detection, however, the diodes should only be 85–90% a saturated to allow room for baseline drift due to uncontrollable variables over the period of data acquisition. The total rms noise for an 85% saturated diode was calculated to be 14,700 electrons according to Equation (1), given sd to be equal to 3,200 electrons. Conversion of this value into absorbance units gave an absorbance noise limit of $4.7 \times 10^{-5}$.

Actual noise was measured from singleiode electropherograms. The tungsten lamp was used as the light source and was moved back and forth behind the capillary array to control the input light intensity and, thus, the number of photoelectrons generated at the diode junction. The measured rms noise level of one diode is linearly proportional to the square root of the number of photoelectrons generated at the diode junction. The intercept of the linear regression of the curve can be related to the rms dark noise according to Equation (1). The measured intercept value was 3,266 electrons, which was close to what was given by the manufacturer, i.e., 3,200 electrons. Also, the measured slope, 0.92, was close to the theoretical value of 1. When the diode was more than 25% saturated with the tungsten lamp as the light source, the major noise source was shot noise. This could be attributed to the relatively low dark noise of the thermoelectrically cooled PDA and the superior stability of the battery-powered DC tungsten lamp (thus a negligible flicker noise). When a PDA was used at room temperature, the rms noise level was at least 5 times higher. The measured rms noise of the diode at 85% saturation level can be converted to an absorbance unit of $4.8 \times 10^{-5}$, which is close to the expected noise limit of $4.7 \times 10^{-5}$. When the hand-held mercury lamp was used, the average measured rms noise for one diode was $9.0 \times 10^{-5}$ at 85% saturation level, which was about two times higher than the expected value. This is believed to be due to the additional intensity flicker noise associated with the mercury lamp.

Mathematical smoothing can reduce the noise significantly without distorting the signal if properly used. To ensure that more data points can be used for smoothing, without sacrificing temporal response, a higher data acquisition rate needs is to be employed. For the PDA detector, data acquisition rate is limited by the digitization rate and the exposure time. The A/D converter in our system is capable of fimctionifig at 25 kHz. So, 40 msec is the minimum exposure time for each data point in the 1024 array. With the tungsten or mrery lamp as the light source in this experiment, a 40-msec exposure time was more than sufficient to attain around 85%. saturation level for all diodes. Normally, an analyte peak is more than 10 sec in width, and 9 data points are enough to represent a typical chromatographic or electrophoretic peak. So, up to 25 data points (1 sec in time) can be used for smoothing with little sacrifice of the width of the analyte peaks. Different kinds of smoothing approaches were compared, and boxcar smoothing proved to be the most efficient method to suppress the noise here. After 25-point boxcar smoothing, the average rms noise was lowered to $1.33 \times 10^{-5}$ AU at 85% saturation level with the tungsten lamp as the light source. One can consider smoothing as increasing the dynamic range (electron well depth) of the diodes after the fact. The observed enhancement factor is close to the factor of 5 predicted by Equation (1).

Figure 3:
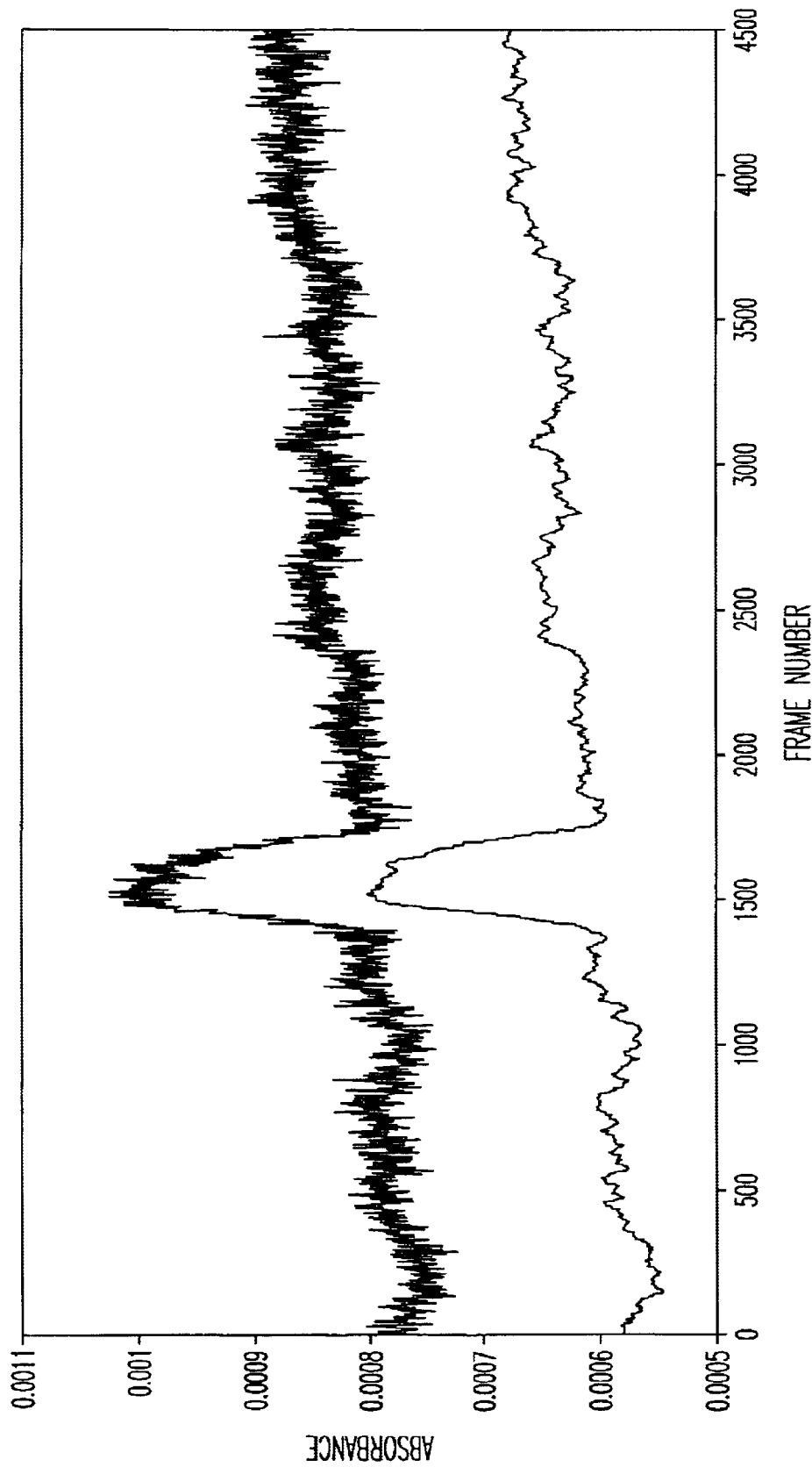
FIG. 3 is a graph of absorbance vs. frame number.

To probe the actual detection limits achievable using this capillary array absorption detection system, electrophoresis of rhodamine 6G, at the concentration of $4 \times 10^{-7}$ M in 1×TBE buffer solution was performed using 1×TBE as the running buffer. The sample was hydrodynamically injected for 6 sec at a height difference of 8 cm. No sample stacking was expected unde these conditions. Capillary electrophoresis was run at 250 V/cm. Detection was performed at a wavelength of 552 nm, defined by an interference filter with 10-nm bandwidth The electropherogram from one capillary in the array is shown in FIG. 3, which is a graph of absorbance vs. frame number, in which the top trace represents the raw data and the bottom trace represents the data with a 25-point boxcar smoothing. The S/N for the rhodamine 6G peak was about 8 (based on a peak height of 0.0002 and an rms noise between frame 1950 and frame 2250 of $2.6 \times 10^{-5}$), which was near the detection limit predicted by Eq. (1). After 25-point boxcar smoothing, the S/N ratio was improved to about 45, as shown in FIG. 3. The resulting $1.8 \times 10^{-8}$ M LOD (S/N=2) for rhodamine 6G injected is comparable to what most commercial single capillary Cou ld achieve.

Figure 4:
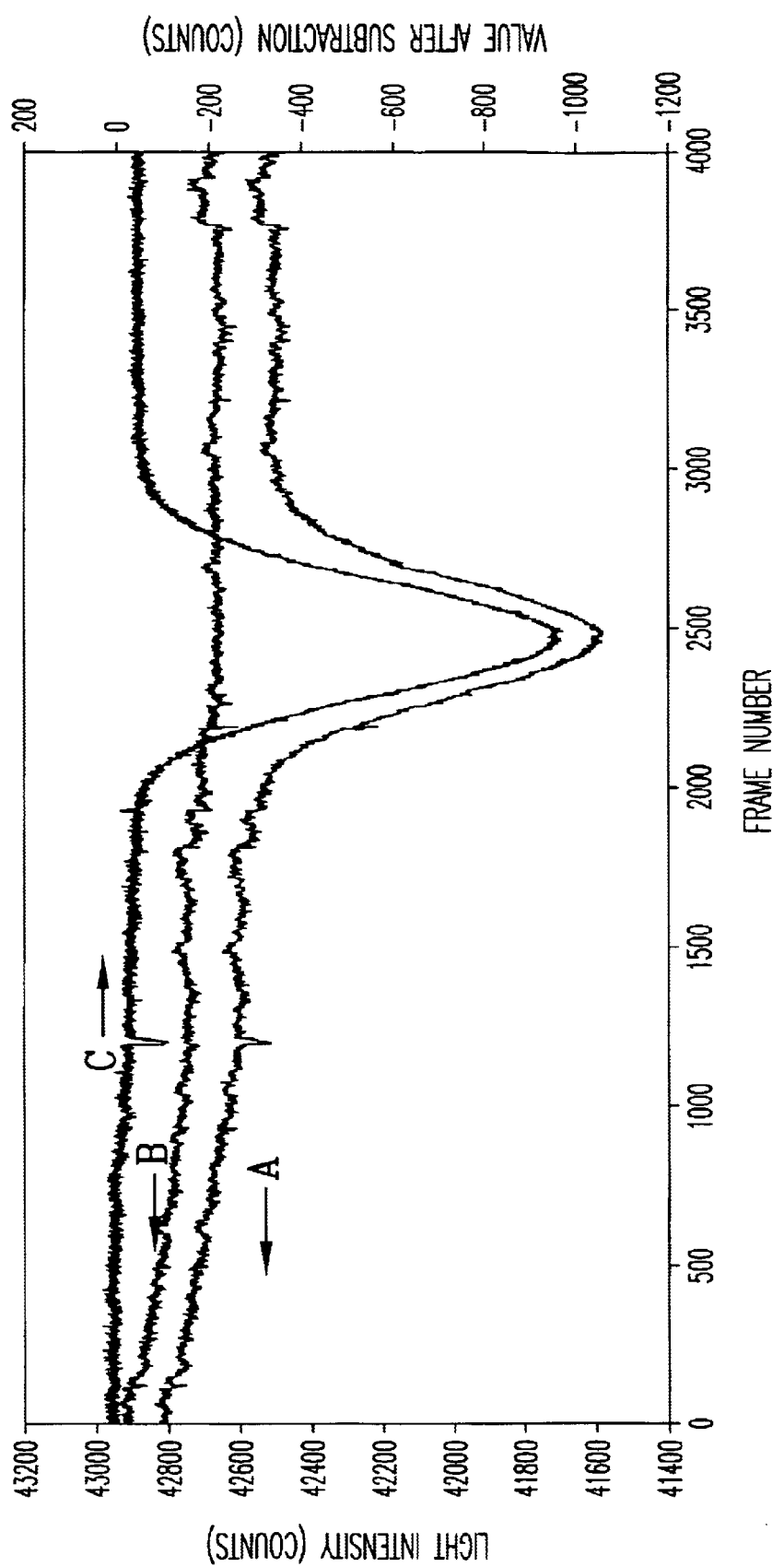
FIG. 4 is a graph of light intensity (counts) vs. frame number vs. value after subtraction (counts).

The hand-held mercury lamp used in this experiment had much more fluctuation than the tungsten lamp did, but less than the pen-light mercury lamp used in previous work (Culbertson et al. (1998), su ra). This is inherent to the discharge nature of the mercury source as compared to Joule heating in the tungsten source. Wile the battery-operated tungsten lamp provided negligible flicker noise in the system, a double-beam scheme was employed to cancel the flicker noise due to the mercury lamp. Certain capillaries in this 96-capillary array were injected with blank samples (suffer solution), and the signals from them were used as reference signals Signals from other capillaries were normalized to the level of the reference signal from the nearest reference capillary, and then the reference signal was subtracted from the normalized signals. FIG. 4, which is a graph of light intensity (counts) vs. frame number vs. value after subtraction (in counts), in which (A) is the electropherogram before noise cancellation, (B) is the reference signal from a blank capillary, and(C) is the electropherogram after noise cancellation, shows the effect of the noise cancellation scheme for a signal at about 85% saturation level. The baseline drift and the intermediate-term noise (i.e., those on the time scale of the signal peaks) were reduced. After nonnalization to the reference signal, the nns noise of the signal was lowered to $6.0 \times 10^{-5}$ AU from $9.1 \times 10^{-5}$ AU. The short-term (high frequency) noise was actually a bit higher. However, these were adequately smoothed out by the boxcar algorithm described above. It was found that, in this 96-capillary array, the blank signal from one capillary could act well enough as the reference for signals from ten capillaries on each side. So only five reference capillaries were needed in the entire 96capillary array. We note that since the data in each diode was acquired consecutively by the digitizer, true temporal correlation of the flicker noise still does not exist between the reference and the measurement channels. This contributes to the short-term noise. This aspect of the system could potentially be improved in the future with more sophisticated diode arrays with flexible clock functions.

Figure 5:
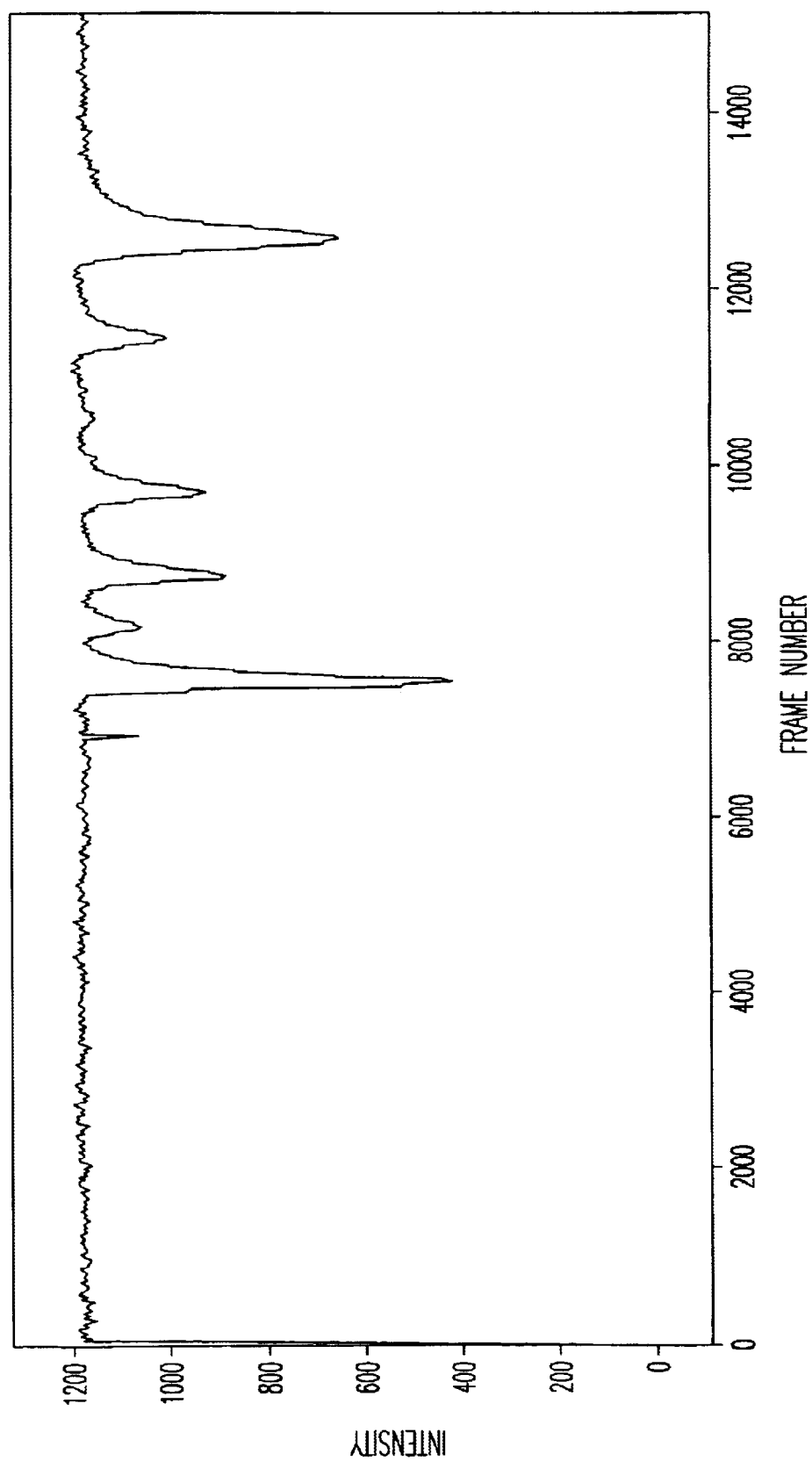
FIG. 5 is a graph of intensity vs. frame number.

FIG. 5, which is a graph of intensity vs. frame number, shows the result of the MEKC separation of five neutral (polyaromatic hydrocarbons) compounds, which are, in order, 9,10-diphenyl-anthracene ($9 \times 10^{-5}$M), benzo[ghi] perylene ($1 \times 10^{-4}$ M), benzo[a]-pyrene ($6 \times 10^{-5}$M), benz[a] anthracene ($4 \times 10^{-5}$M), fluoranthene ($1 \times 10^{-4}$ M) and anthracene ($5 \times 10^{-5}$M). The LOD (S/N=2) was $1.9 \times 10^{-6}$M before smoothing and $9.2 \times 10^{-7}$M after smoothing. The final noise level was higher by about 2-fold compared to the CZE separation experiment due to the higher intensity fluctuation of the hand-held mercury lamp, as discussed above.

The MEKC separation also generated very high current, which is 30 $\mu$A per capillary and about 3 mA for the whole array. Therefore, a large amount of heat was produced during the separation. Some cooling approaches needed to be employed to help the heat dissipation. It was found that the hottest part in this setup during the separation was the detection window. This was because all of the capillaries were densely packed together in this region. To avoid mechanical vibrations in the capillary array, which would bring about excess amounts of noise, a laminar flow of nitrogen gas was created in parallel to the detection window of the capillary array to carray away the heat generated in this region. After the nitrogen cooling approach was employed, heat dissipation was not a problem in this setup.

To minimize the cross-talk between adjacent capillares, the image of a capillary on the face of the PDA needs to be big enough to ensure that the diode corresponding to the center of the capillary receives minimal stray light from adjacent capillaries. It was found if the image of one capillary covers more than 8 diodes in the PDA, cross-talk was less than 0.2%, which is negligible for the multiplexed analysis. Cross-talk was also found to be related to the spatial alignment of the capillary array. We found that the image of each capillary in the array needs to be parallel to the diodes in the PDA. Otherwise the signal from more than one capillary may cross over each diode (which is narrow but long) and cause more cross-talk. The array also needs to be confined to a plane, or else imaging will not be uniform for each capillary. Finally, vibrations in the capillaries, especially when high voltage is applied or when cooling fans are improperly situated, will cause additional flicker noise in the system. Rigid mounting of the array and of the optics is, therefore, critical.

Figure 6:
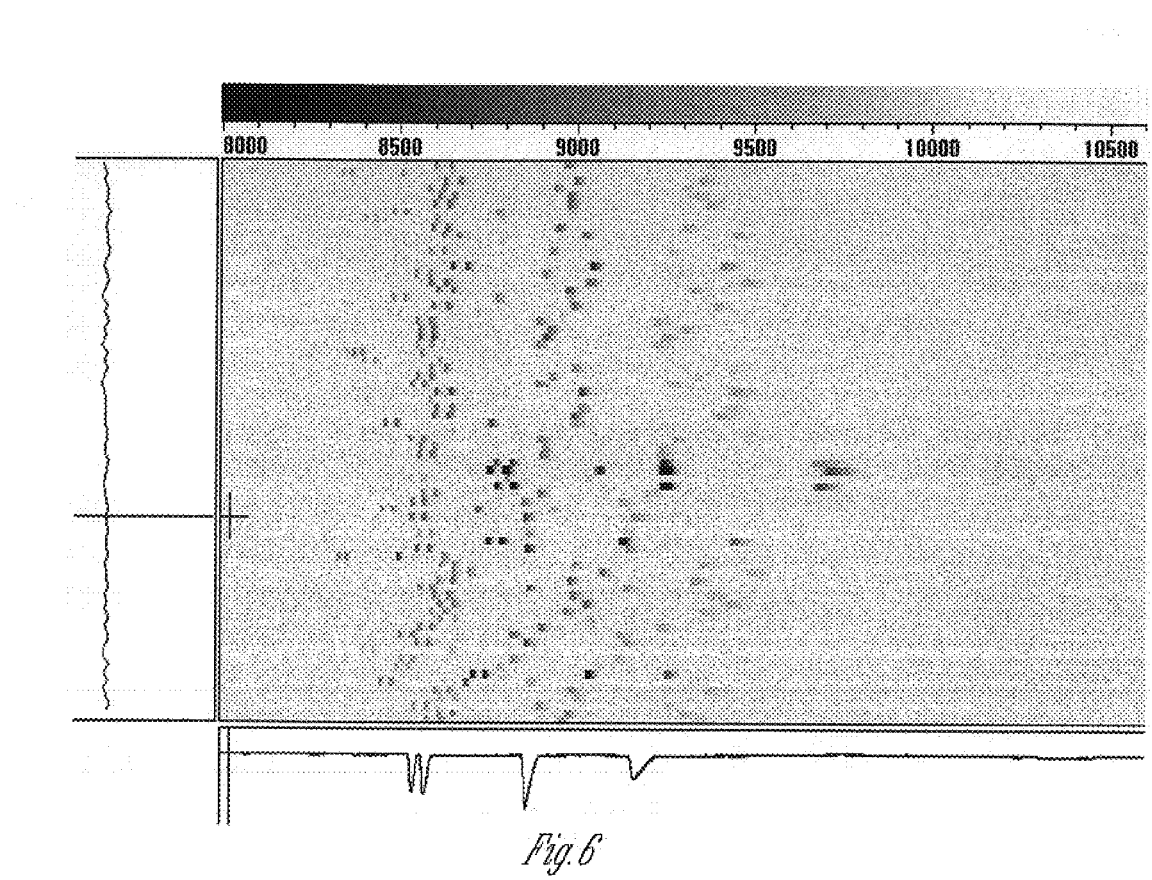
FIG. 6 is the result of CZE separation of four visible dyes in a 96 capillary array.

FIG. 6, which is the result of CZE separation of four visible dyes in the 96 capillary array, in which the order of dyes is 5CF ($4 \times 10^{-5}$ M), 6CF ($4 \times 10^{-5}$ M), F ($8 \times 10^{-5}$ M) and DADCF ($1.2 \times 10^{-4}$M), the horizontal direction represents the location of the capillaries, the vertical direction represents migration time from 5.3 to 7.0 min, the top plot represents intensity across the array, and the left plot represents intensity along one of the capillaries. Relatively uniform separation resolution and S/N distribution can be observed from the reconstructed image file. Cross-talk between adjacent capillaries was not observable, as expected for this analyte concentration range.

Figure 7:
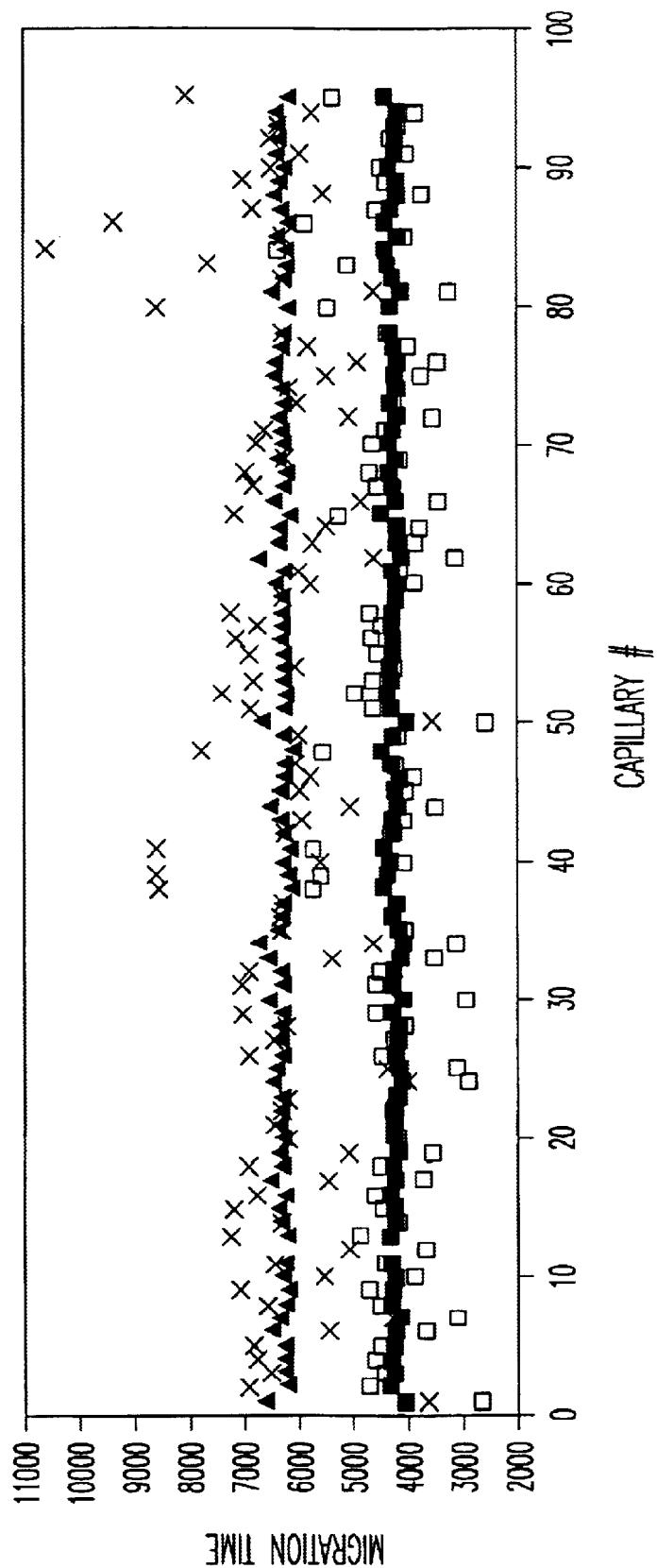
FIG. 7 is a graph of migration time vs. capillary number.
Figure 8:
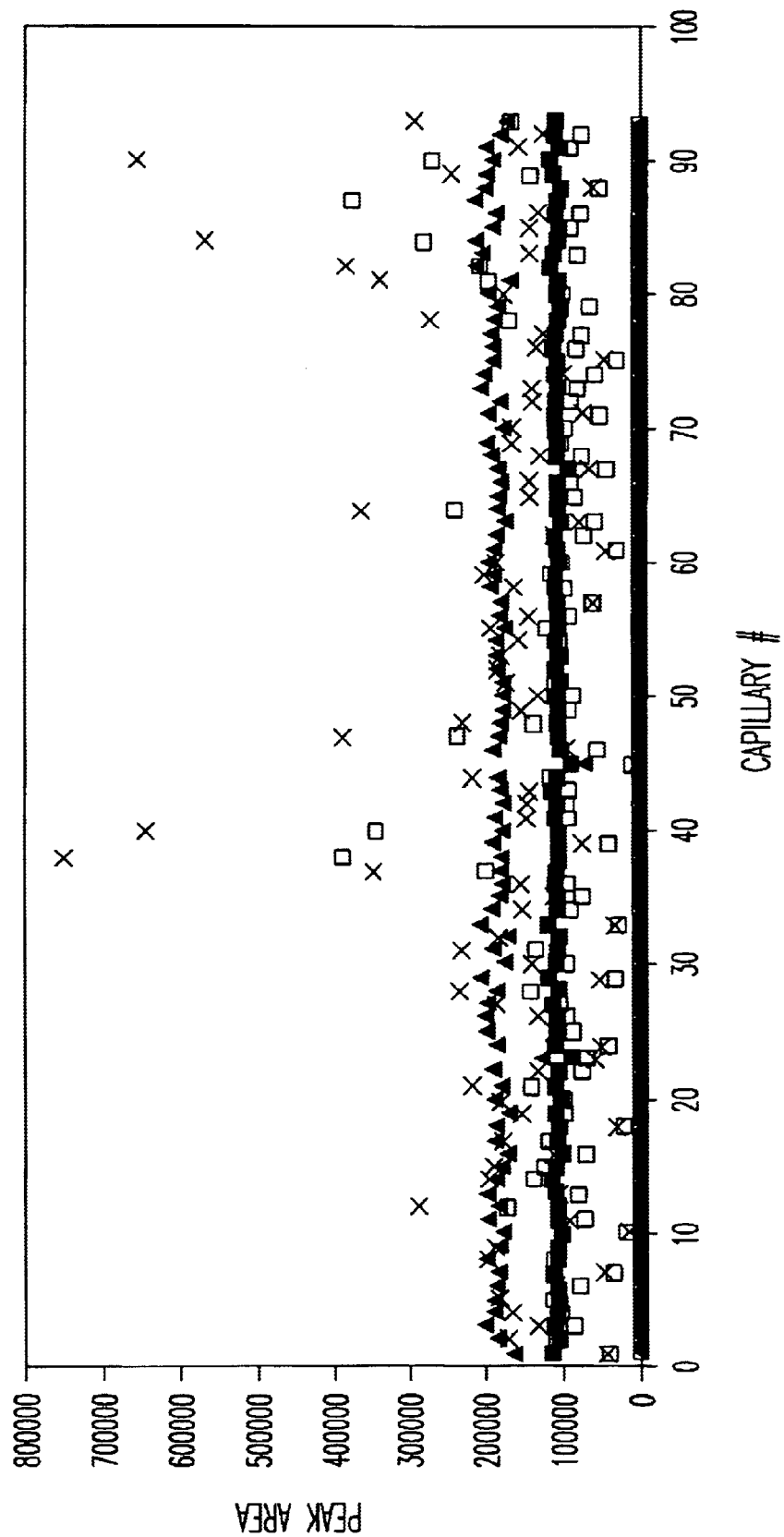
FIG. 8 is a graph of peak area vs. capillary number.

The results for multiplexed CE indicate that the migration times are highly nonuniform among the capillaries. This is to be expected from the absence of temperature regulation and variations in the column surfaces. We have demonstrated that an internal standardization scheme can be employed to normalize the results among the capillaries so that the migration times and the peak areas are reliable enough for high-throughput applications. FIG. 7, which is graph of migration time vs. capillary number in which the open symbols represent raw data and the closed symbols represent data normalized by two internal standards for two fluoresceins, confirms that, by using the first and the last peaks as the two internal standards, both the migration times and the peak areas become uniform across the array. For the second and third peaks the relative standard deviations (RSDs) of migration times were reduced from 17% and 22% to 1.9% and 2.0%, respectively, and the RSDs of peak areas were reduced from 65% and 87% to 3.8% and 8.8%, respectively. In the case of peak areas, two capillaries (#23 and #45, see FIG. 8, which is a graph of peak area vs. capillary number in which the open symbols represent raw data and the closed symbols represent data normalized by two internal standards for two fluoresceins) dominated the contributions to the RSDs. If these two capillaries were omitted from the statistical analysis, the RSDs were lowered to 2.9% and 5.3%, respectively. The fact that this normalization scheme (Xue et al., *Anal. Chem.* 71:2642–2649 (1999)) works equally well with the absorption detector here shows that the data in FIG. 7B are all within the linear range of the detector. This is not surprising, since at no time did the intensity decrease by more than 15% (FIG. 6). For larger absorptions, a logarithmic correction will need to be applied to maintain a linear response.

This example demonstr s for the first time a high-throughput system for analyzing multiple samples simultaneously using absorption detection. Uniform separation efficiency and good S/N were obtained. The LOD achievable for such a system, such as the 96-capillary array electrophoresis system described above, is comparable to those for commercial single-capillary electrophoresis machines using absorption detection. The separation of ionic and of neutral analytes were demonstrated by zone electrophoresis and by MEKC, respectively. Consequently, the capillary array electrophoresis system can do everything single-capillary electrophoresis absorption instrbents can do, only with much higher throughput. Potentially, the present inventive system also can serve as an alternative to HPLC in many applications. No moving parts were used in this system. Once the positions of all components are fixed, the only thing that needs to be adjusted is the focal point of the camera lens, just like taking a picture, to get the best focused image of the capillary array. One focused, no noticeable changes in the system were observed over many days. Also, no lasers are used, thus the system should besmaller, more cost effective and easier to use and maintain than the multiplexed laser-reduced fluoresce CE systems. Besides, the analytes do not have to be fluorescent to be detected. The absorption wavelength can be selected by simply changing a filter. Since the sample injection process involves only moving different microtiter plates under the injection block and can be fully automated, it should be possible to obtain a true throughput that is 100 times higher than what conventional single CE absorption deternanations can achieve.

Example 2

This example demonstrates the application of the present invention to genetic typing and diagnosis.

Based on the 96-capillary array electrophoresis system of Example 1, DNA analysis protocols were designed to take advantage of capillary array gel electrophoresis and absorption detection based on the inherent spectral properties of the DNA bases and the fact that a 100-bp DNA contains 100 absorbing units that can provide excellent net absorptivity for sensitive detection. The method was tested on two broadly used PCR protocols using typical concentrations of starting materials.

Samples were prepared as follows:
Polymerase Chain Reaction
1. Multiplexed PCR for Variable Number of Tandem Repeats (VNTR) loci AmpliFLP D1S80 PCR amplification kit was purchased from Perkin-Elmer Foster City, Calif.). The kit included D1S80 PCR Reaction Mix (containing two D1S80 primers, AmpliTaq DNA polymetase and dNTPs in buffer), $MgCl_2$ solution and Control DNA 3(humangenomic DNA of D1S80 type 18, 31 inbuffer). The PCR mixtures used were as follows:

| | |
|---|---|
| Positive Control: | 20 µl of D1S80 PCR Reaction Min 10 µl of $MgCl_2$ solution and 20 µl of Control DNA3. |
| Negative Control: | 20 µl of D1S80 PCR Reaction Mix, 10 µl of $MgCl_2$ solution and 20 µl of autoclaved D1 $H_2O$. |

The polymerase chain reactions were performed with the following parameters: 30 cycles of denaturation at 95° C. for 15 sec, annealing at 66° C. for 15 sec, and extension at 72° C. for 40 sec. The thermal cycler used was a Perkin-Elmer GeneAmp PCR system 2400.

2. PCR for Human Immnunodeficiency Virus (HIV)

The HIV testing kit (Perkin-Elmer) included positive control DNA that includes all parts of the HIV-1 genome, negative control DNA, HIV primers, AmpliTaq DNA polymerase, dNTPs, PCR reaction buffer and MgCl$_2$ solution. The PCR mixtures used are listed in Table 1. The protocol for the Perkin-Elmer GeneAmp thermal cycler is 40 cycles of denaturation at 95° C. for 30 sec, annealing and extension at 62° C. for 1 min. The annealing and extension temperatus were the ame for this amplification.

TABLE 1

PCR mixtures (or HIV amplification

| Component | Addition Order | Volume | Final Concentration |
|---|---|---|---|
| Autoclaved, deionized water | 1 | 32.8 µl | |
| 10x PCR buffer II | 2 | 5 µl | 1x |
| DNTPs | 3 | 1 µl each | 200 µM each dNTP |
| HIV-1 primer 1 (SK38) | 4 | 1 µl | 0.5 µM |
| HIV-1 primer 2 (SK39) | 5 | 1 µl | 0.5 µM |
| AmpliTaq DNA polymerase | 6 | 0.2 µl | 1 unit |
| 25 Mm MgCl$_2$ solution | 7 | 5 µl | 2.5 mM |
| Positive Control DNA or Negative Control DNA | 8 | 1 µl | 0.5 µg human placental DNA |

DNA Purification

All PCR products were purified with Microcon YM-30 centrifugal filter devices (Millipore, Bedford, Mass.). After the purification, salts, dNTPs and most HIV-1 primers were eliminated from the DNA samples.

The 96 capillary array electrophoresis system with photodiode array absorption detection as described in Example 1 was used. A DC-powered mercury lamp (UVP Inc., Upland, Calif.) was used as the light source, which gave lower noise levels than the AC-powered mercury lamp used in previous work. Tbe absorption wavelcngth was set at 254 nm by an interference filter (Oriel). The total length of the capillaries was 55 cm, with 35-cm effbctive length. The capillary array was first flushed with deionized water and then with 1 ml of 2% PVP at a pressure of 100 psi. While the injection ends were immersed in the buffer resrvoir, 0.5 ml of 2% PEO (600,000 MW) sieving matrix was pushed into the capillary bundle at 100 psi. The procedure roughly took 20 min. After the gel filling, ethdidum bromide was added to the buffer reservoirs at the concentration of 1 µg/ml . The system was then pre-run for 10 min with the electric field strength at 150 V/cm. Afte the pre-run, ethidium bromide should have spread out eveny in the sieving matrix through electrical migration. Ethidium bromide is known to make the DNA fiagments mom rigid, thereby leading to sharper bands in CGE. It was not expected to alter signiff-cantly the absorption strength of the DNA fragments in this study. The samples were injected electrokinetically at 150 V/cm for 15 sec. A field strength of 150 V/cm was employed for the separation. The total current was about 620 µA during the seperation process. Twelve different samples were used in the 96-capillary array resis experiment, which are detailed in Table 2. Each type of sample was injected into and run in eight different capillaries in the 96-capillary array.

TABLE 2

Sample description in the capillary array electrophoresis

| Sample No. | Description |
|---|---|
| 1 | 4 µl of HIV-1 primer (SK38) |
| 2 | 4 µl of purified HIV-1 negative PCR product |
| 3 | 4 µl of purified HIV-1 positive PCR product |
| 4 | 4 µl of 100 bp ladder |
| 5 | 3 µl of purified HIV-1 negative PCR product with 1 µl of 100-bp ladder |
| 6 | 3 µl of purified HIV-1 positive PCR product with 1 µl of 100-bp ladder |
| 7 | 4 µl of purified D1S80 negative PCR product |
| 8 | 4 µl of purified D1S80 positive PCR product |
| 9 | 4 µl of 50-bp ladder |
| 10 | 3 µl of purified D1S80 negative PCR product with 1 µl of 50-bp ladder |
| 11 | 3 µl of purified D1S80 positive PCR product with 1 µl of 50-bp ladder |
| 12 | 4 µl of DI H$_2$O |

Figure 9:
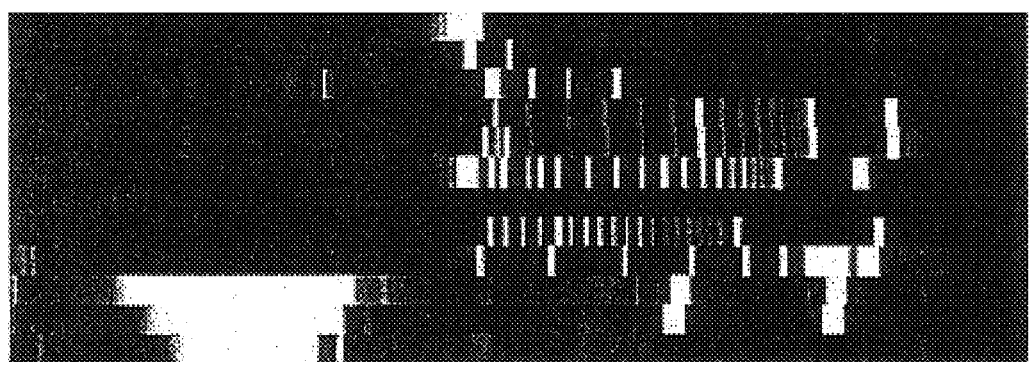
FIG. 9 is a reconstructed twodimensional electropherogram for capillary array electrophoresis.

FIG. 9, which is a reconstructed two-dimensional electropherogram for capillary array electrophoresis, in which the 12 capillaries (corresponding to the 12 samples described in Table 2) are aligned vertically and the migration direction is from left to right, shows the result of the capillary array gel electrophoresis for DNA analysis as a reconstructed "gel" image. The vertical direction represents the capillary array arrangement, while the horizontal direction represents the migration time. All separations were finished within 25 min. Capillary #84 (Sample type 11, see Table 2) showed bad separation resolution after 350 base pairs. The other 95 capillaries gave reasonable separation and good signal-to-noise ratios. The migration times and peak intensities were highly non-uniform among the capillaries. This was to be expected from the absence of temperature regulation and variations in the column surfaces. An internal standardization scheme can be employed to normalize the results among the, capillaries so the migration times and the peak areas are reliable enough for high-throughput applications.

Figure 10:
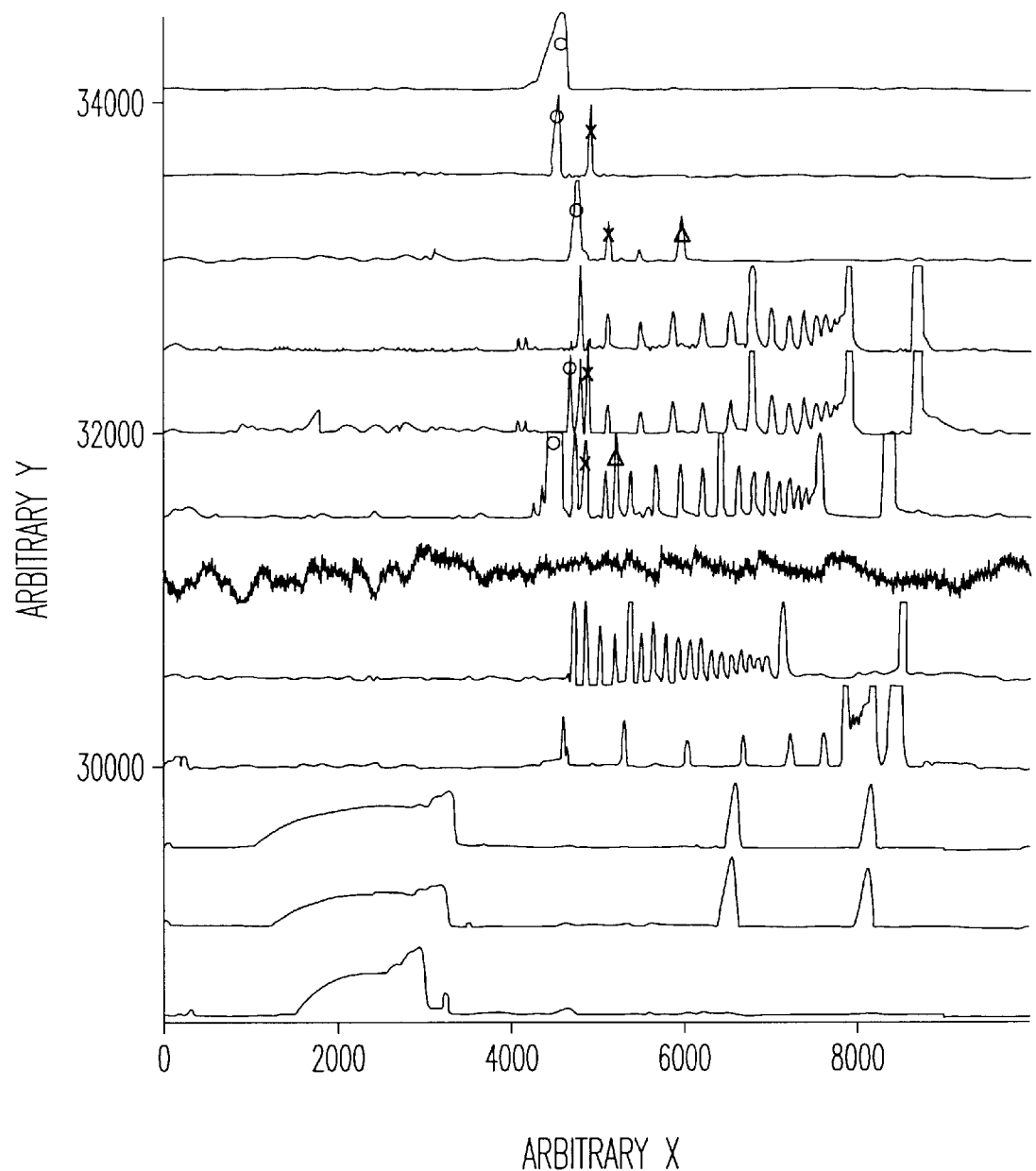
FIG. 10 is a set of extracted electropherograms for capillary array electrophoresis.

Actual electropherogmrns were extracted from capillaries #3, 9, 17, 25, 33, 41, 49, 57, 65, 73, 85 and 89 to represent each type of sample described in Table 2, and are shown in FIG. 10, in which the 12 capillaries (corresponding to the 12 samples described in Table 2) are stacked vertically accordingly to the order in FIG. 9 and the migration times are plotted from left to right. In capillaries #9–16 and #17–24, negative and positive HIV-1 PCR products were injected respectively. The positive and negative results can be easily differentiated through the HIV-1 gag fragment peak (triangle), which appeared only in the clectropherograms from capillaries #17–24. Both the positive and negative HIV-1 PCR samples also contained the excess primers (circle) and the primer dimers (cross). To provide an even higher level of confidence for identification, despite the variation of migration times among capillaries, the HIV-1 gag fragments, primers and primer dimers can be sized by mixing the PCR products with 100-bp DNA ladders (capillaries #25–32), and injecting them into capillaries #33–40 and #41–48. The electropherograms from the latter two groups of capillaries showed that the HIV-1 gag fragment is about 115 bp and the primer dimer is about 60 bp.

In the electropherograms from capillaries #1–8, the HIV-1 primers gave broad peaks, which we believe are due to sample overloading. Deionized H$_2$O was injected into capillaries #89–96, which gave blank electropherograms. These electrophergrams served as blank references and were suiracted from the signal in the other capillaries to cancel out the flicker noise from the mercury lamp, as reported before. The electropherograms from capillaries #49–56 showed negative D1S80 PCR results, where only the primer peaks can be observed The electropherograms from capillaries #57–64 showed positive D1S80 genotyping PCR results. Two component peaks (D1S80type 18 and 31) can be observed as expected from the heterozygous samples in adtitfi to the very broad primer peaks. Again, to increase the confidence level for identification, the two D1S80 components as well as the primer were roughly sized by mixing each PCR product with a 50-bp ladder (capillaries #65–72) and injecting them into capillaries #73–80 (negative) and #81–88 (positive). The results showed the two D1S80 components to be about 400-bp and 600bp.

Current high-throughput approaches to the analysis of PCR products are based primarily on electrophoretic separation and laserxcited fluorescence detection. This example demnonstrates that the present invention can be applied to genetic typing and diagnosis based simply on UV absorption detection. The additive contribution of each base pair to the total absorption signal provides adequate detection sensitivity for analyzing most PCR products. Not only is the use of specialized and potentially toxic fluorescent labels eliminated, but also the complexity and cost of the instrumentation are greatly reduced. For example, no lasers are used. UV absorption detection of DNA products reduces the cost of analysis since it does not require labeling. The capillary array was flushed with water in between runs and did not show any degradation over tens of runs in a one-month period. Since the sample injection can be fully automated, this example demonstrates that it should be possible to obtain a true DNA analysis throughput that is 100 times (scalable to 1,000 times) higher than what commercial single capillary gel electrophoresis systems can achieve, at relatively low cost.

Example 3

This example demonstrates the application of the present invention to high-throughput comprehensive peptide mapping of proteins.

An experimental CE setup for multi-dimensional 96-capillary array electrophoresis similar to that of Example 1 was used. Briefly, a total of 96 fused-silica capillaries Polynicro Technologies, Inc., Phoenix, Ariz.), 50 $\mu$m i.d. and 360-$\mu$m o.d., with 50-cm effective length and 70-cm total length were packed side by side at the detection window and clamped between two flat surfaces of a plastic mount. The window was created after packing by using an excimer laser beam to burn off the polyimide coating. At the ground end (outlet), every 12 capillaries were bundled together to allow simultaneous filling of six-different buffers for six-dimensional peptide mapping. At the injection end, the capillary array was spread out and mounted on a copper plate to form an 8×12 format with dimensions to fit into a 96-well microtiter plate for sample introduction. Gold-coated pins (96) (MillMax Mfg. Corp.) were mounted on the copper plate near the capillary tips to serve as individual electrodes, with the capillary tips slightly extended (~0.5 mm) beyond the electrodes to guarantee contact with small-volume samples. A high-voltage power supply (Glassman High Voltage, Inc., Whitehorse Station, N.J.) was used to drive the electrophoresis.

The light source, filter, capillary array holder, and PDA detector were all contained in a light-tight met al box attached to an optical table as described above. As the light source, a 213.9-nm zinc lamp (model ZN-2138, Cole-Parmer) was used for UV absorption detection. The transmitted light from the capillary array pased through an interference filter (Oriel) and a quartz lens Nikon; f.l.=105 mm; F=4.5). An inverted-image of the capillary array at a nominal magnification factor of 1.2 was created by the quartz lens on the face of the PDA. The PDA (Hamarnmatsu model S5964, Hamamatsu, Japan) incorporated a linear image sensor chip (1024 diodes, 25-$\mu$m in width, 2500-$\mu$m in height), a driver/amplifier circuit, and a temperature controller. The built-in driver/amplifier circuit was interfaced to an IBM-compatible computer (233-MHz Pentium, Packard Bell) via a National Instrument PCI E Series multifimction 16-bit I/O board. All codes used to operate the PDA and to acquire the data were written in house using Labview 5.0 software (National Instruments, Austin, Tex.).

The raw data sets were converted into single-diode electropherograms by another in-house Labview program. Data treatment and analysis were performed using Microsoft Excel 97 and GRAMS/32 5.05 (Galactic Industries).

In the multi-dimensional CE experiments, the capillary array was first flushed with mcdanol and then water for cleanup. The six running buffers used for four-dimensional CZE separations and two-dimensional MEKC separations were as follows: (1) 50 mM Trizam®·Phosphate buffer (pH 2.5 with $H_3PO_4$), (2) 50 mM sodium acetate buffer (pH 5.0 with acetic acid), (3) 0.1 M Trizam®·Base/0.1 M Tricine Siffer (pH 8. 1), (4) 0.1 M CHES/0. 1 M NaOH (pH 9.3), (5) 0.1% Tween 20 in 50 mM sodium acetate buffer (pH 5.0 with acetic acid), and (6) 7% Tween 20 and 10 mM SDS in 0.1 M Trizma®·Base/0.1 M Tricine buffer (pH 8.1). The samples were put into a 96-well microtiter sample plate (1 $\mu$l/well) and gravity injected at the anode for 60 sec at 8-cm height. The applied electric field was +157 V/cm and electrophoresis was performed at ambient temperature. After each run, the capillaries were rinsed with 0.1 M NaOH, water, and running buffer for 5 min each.

All CE separations for CZE and MEKC analyses were optimized on an ISCO (Lincoln, Nebr.) Model 3140 Electropherograph System before the multi-dimensional multiplexed CE runs. Bare fused-silica capillaries (Polymicro Technologies, Inc., Phoenix, Ariz.) with 50-cm effective length and 75-cm total length (50-$\mu$m i.d. and 361-$\mu$m o.d.) were used. Four different buffer systems were investigated for CZE separations and two different buffer systems were also investigated for MEKC separations. The opti compositions are described above. The samples were introduced with hydrodynamic flow by placing the inlet of the capillary into the sample vial and raising the sample vial 30 cm above the exit vial and allowing the sample to siphon into the capillary for 10 sec. The applied electric field was +227 V/cm and electrophoresis was performed at ambient temperature. The detection wavelength was set at 214 nm for monitoring peptide framents. After each run, the capillary was rinsed with 0.1 M NaOH, water, and running buffer in order for 5 min each.

Tryptic digestion of BLGA and BLGB was carried out according to the procedure of Cobb et al. ((1989), supra) without the dialysis and lyophilization steps. A mixture of 2 mg/ml BLG and trypsin was prepared with a 10 mM Trizma®·Base and 50 mM ammonium acetate buffer (pH 8.2) containing 0.1 mM calcium chloride. Trypsin was added at a trypsin-protein ratio of 1:50 (w/w), and the digestion mixture was incubated at 37° C. for 5 hr. The digest was directly injected into the separation CE system without filtration.

Bovine β-lactoglobulin (BLG) is the major whey protein of cow's milk. Mature bovine BLG has 162 residues as shown in FIG. 11 [SEQ ID NO: 1], which represents the peptide maps of three variants of BLG. Three variants of BLG, labeled as A, B, and C, commonly occur in cow's milk. Variants A and B differ at two sites: aspartic acid (D) 64 in BLGA is changed to glycine (G) in BLOB, and valine (V) 118 in BLGA is changed to alarune (A) in BLOB. Variants B and C differ at one site: glutamine (Q) 59 in BLGB is changed to histidine (H) in BLGC (Bin et al., *Protein Science* 8: 75–83 (1999)). Tryptic digestion is quantitative and very specific because trypsin cleaves only at the C-terminal side of lysine and arginine residues. The theoretical fragments are listed in Table 3. In the case of BLG, seveteen different peptides exist after ryptic digestion.

Up to the present, peptide mapping of proteins is primarily based on the cleavage of proteins with enzyme or chemical agents, followed by a one- or two-dimensional separation of the resulting peptide fragments. While the resolution of peptide fragments achieved by oneimensional separation is often insufficient to resolve the complex mixture of peptides, the conventional two dimensional techniques suffer from the difficulty of efficiendy recovering uncontaminated peptides from the first dimension to transfer to the second dimension. Also, two-dimensional separation conditions have to be changed according to the sample protein. To overcome these problems a six-dimensional system was used. By combining four different CZE condi-

TABLE 3

Theoretical products of tryptic digest of BLGA and BLGB

| Expected fragment | Sequence | Residues |
|---|---|---|
| 1 | L—I—V—T—Q—T—M—K | 1–8 |
| 2 | G—L—D—I—Q—K | 9–14 |
| 3 | V—A—G—T—W—Y—S—L—A—M—A—A—S—D—I—S—L—L—D—A—Q—S—P—L—R | 15–40 |
| 4 | V—Y—V—E—E—L—K—P—T—P—E—G—D—L—E—T—L—L—Q—K | 41–60 |
| 5 | W—E—N—D—E—C—A—A—Q—K (W—E—N—G—E—C—A—Q—K)$^a$ | 61–69 |
| 6 | K | 70 |
| 7 | I—A—A—E—K | 71–75 |
| 8 | T—K | 76–77 |
| 9 | I—P—A—V—F—K | 78–83 |
| 10 | I—D—A—L—N—E—N—K | 84–91 |
| 11 | V—L—V—L—D—T—D—Y—K | 92–100 |
| 12 | K | 101 |
| 13 | Y—L—L—F—V—M—E—N—S—A—E—P—E—Q—S—L—V—C—Q—C—L—V—R (Y—L—L—F—V—M—E—N—S—A—E—P—E—Q—S—L—A—C—Q—C—L—V—R)$^a$ | 102–124 |
| 14 | T—P—E—V—D—D—E—A—L—E—K | 125–135 |
| 15 | F—D—K | 136–138 |
| 16 | A—L—K | 139–141 |
| 17 | A—L—P—M—H—I—R | 142–148 |
| 18 | L—S—F—N—P—T—Q—L—E—E—Q—C—M—I | 149–162 |

$^a$The peptides in parenthesis are fragments of BLGB.

Figure 12:
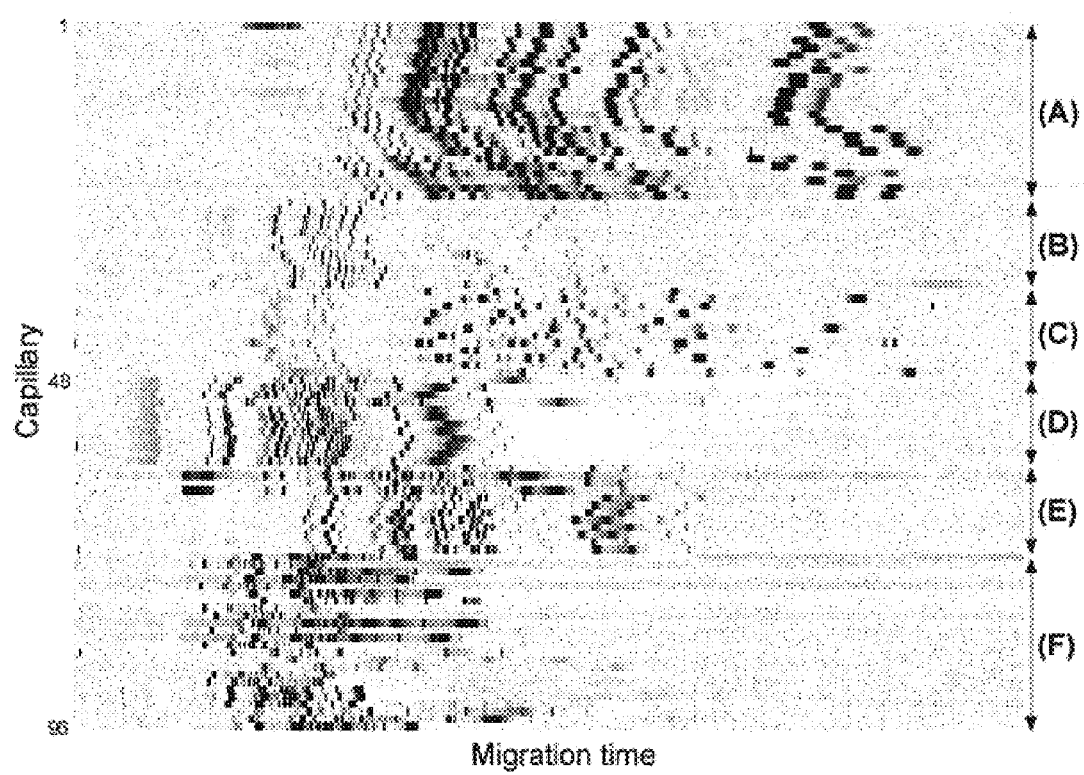
FIG. 12 shows the results of the sixdimensional separations (capillary vs. migration time) of tryptic digests of BLGA and BLGB in the 9&capillay array.

A multiplexed capillary array systen allowed high-thoughput characterization and generation of peptide maps of proteins, after enzymatic digestion, using six-dimensional capillary electrophoresis at a constant applied electric field. In a 96-capillary array image obtained using a zinc lamp and the PDA, the center of each capillary corresponds to a "peak" in the image. Between every two center "peaks," there is a "valley" which corresponds to the wall of the capillary. When the capillary array image was well-focused onto the PDA, the intensities of these valleys became miniize. This feature was used to produce the best focusing. "Spacing peaks" (see above) were eliminated in this study. This results from a special treatment on the window of the capillary array, whereby epoxy glue was applied between the capillaries on the detection window. The epoxy glue greatly strengthened the window area of the capillary array and minimized movement of the capillaries in the electric field. Because the epoxy glue is not UV transent, it absorbed all of the light that would have passed though the spacing of the capillaries and eliminated the "spacing peaks." This further reduced stay light for absorption detection. The zinc lamp provided 213.9-nm light that is well-suited for the absorption detection of peptides. The emitting length of the zinc lamp is about 2 cm, which is long enough for uniform illumination of the entire capillary array (1.5 cm). There was less than 2× variation in optical throughput from the center to the edge of the array. This means that the detection limit varied by less than $\sqrt{2}$×across the array. The zinc lamp was very stable and produced negligble flicker noise, so no doubleba subtraction was necessary in this experiment.

tions at different pHs and two different MEKC conditions, comprehensive and complementary information about the peptides of arbitrary proteins was obtained. As shown in the results of single-capillary runs (FIGS. 15 and 16), the peptide fragments at different separation conditions showed different but related peptide maps. FIG. 12 shows the results of the six-diensional separations of tryptic digests of BLGA and BLGB in the 96-capillaray, in which (A) is 50 mM Trizam®•phosphate buffer (pH 2.5 with $H_3PO_4$), (B) is 50 mM sodium acetate buffer (pH 5.0 with acetic acid), (C) is 0.1% Tween 20 in 50 mM sodium acetate buffer (pH 5.0 with acetic acid), (D) is 0.1 M Trizma®•Base/0.1 M tricine buffer (pH 8.1), (E) is 7% Tween 20 and 10 mM SDS in 0.1 M Trizma®•Base/1.0 M tricine buffer (pH 8.1), and (F) is 0.1 M CHES/0.1 M NaOH (pH 9.3). The vertical direction represents the capillary array arrangement, while the horizontal direction represents the migration time. The applied electric field was +157 V/cm. A column, bare fused-silica capillary with effective/total length of 50/70 cm and 50 $\mu$m i.d. was used. Hydrodynamic injection was conducted for 60 sec at 8 cm height In the singleapillary CE system, when the electric field of +227 V/cm was applied to the 50-$\mu$m i.d. capillary, the current was below 20 $\mu$A at ambient temperature. However, the capillaries were packed side by side in the 96-capillary array system and the dense packing generated a much higher temperature at the same separation condition. Consequently, some of the capillaries can lose current during the separation because of the formation of bubbles. Thus, a lower electric field of +157 V/cm was applied in spite of an increased analysis time. All separations were still completed within 45 min. Although capillaries 87 and 88 showed unusually long separation times and much lower signal levels, all of the other 94-capillaries gave comparable separation times and good signal-to-noise ratios. As shown in the reconstructed image, even for the same separation condition, the migration times and peak intensities were not uniform among the capillaries. This phenomenon is to be expected from the absence of temperature control in the experiment (Xue et al. (1999), supra, and Gong et al. (1999), supra). However, we have demonstrated that an internal standardization scheme can be applied to normalize the results among the capillaries (Xue et al. (1999), supra; and Gong et al. (1999), supra) so that the corrected migration times and peak areas are of sufficient reliability for high-throughput applications.

Figure 13:
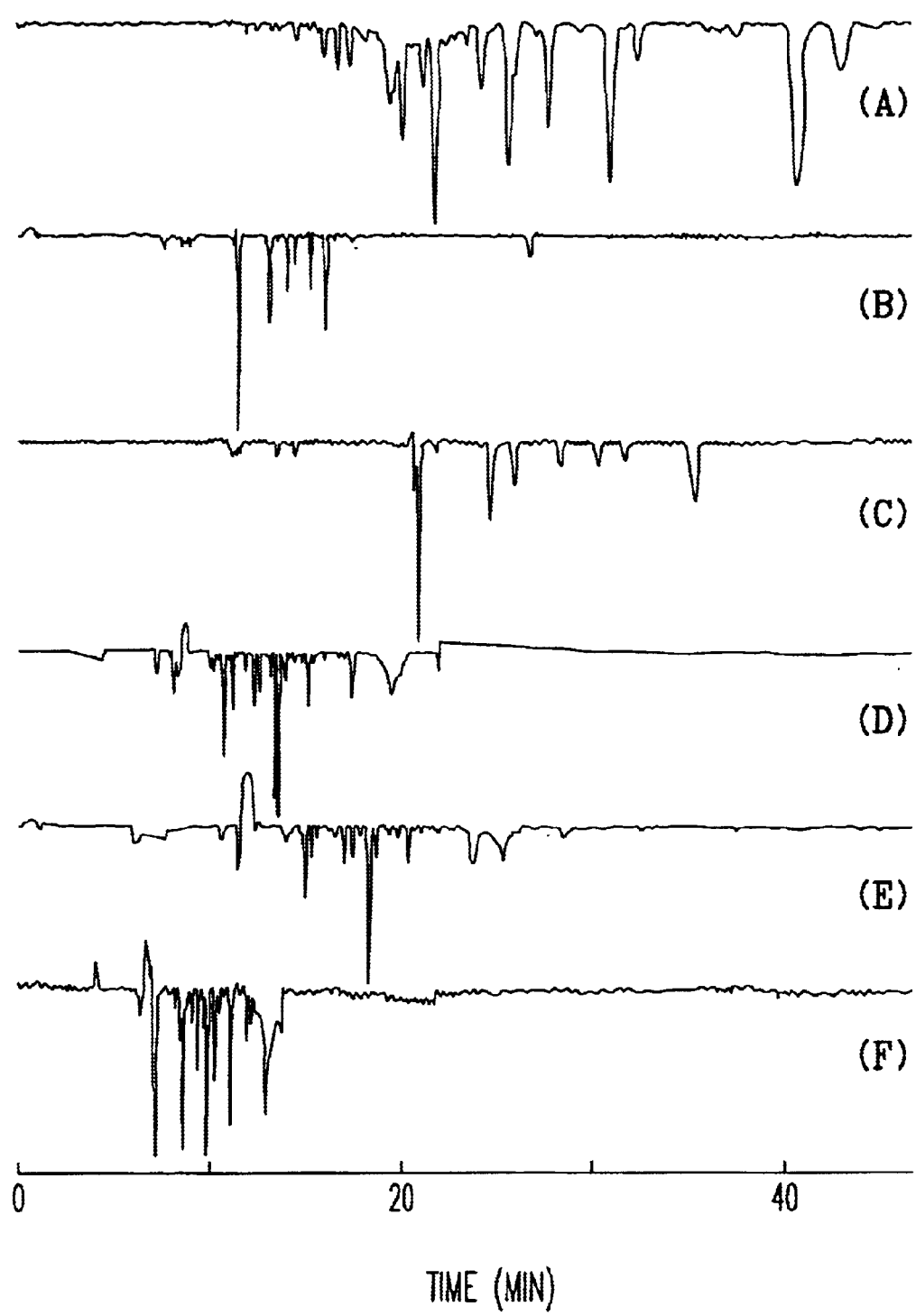
FIG. 13 shows selected electropherograms of BLGA extracted from the data in FIG. 12.
Figure 14:
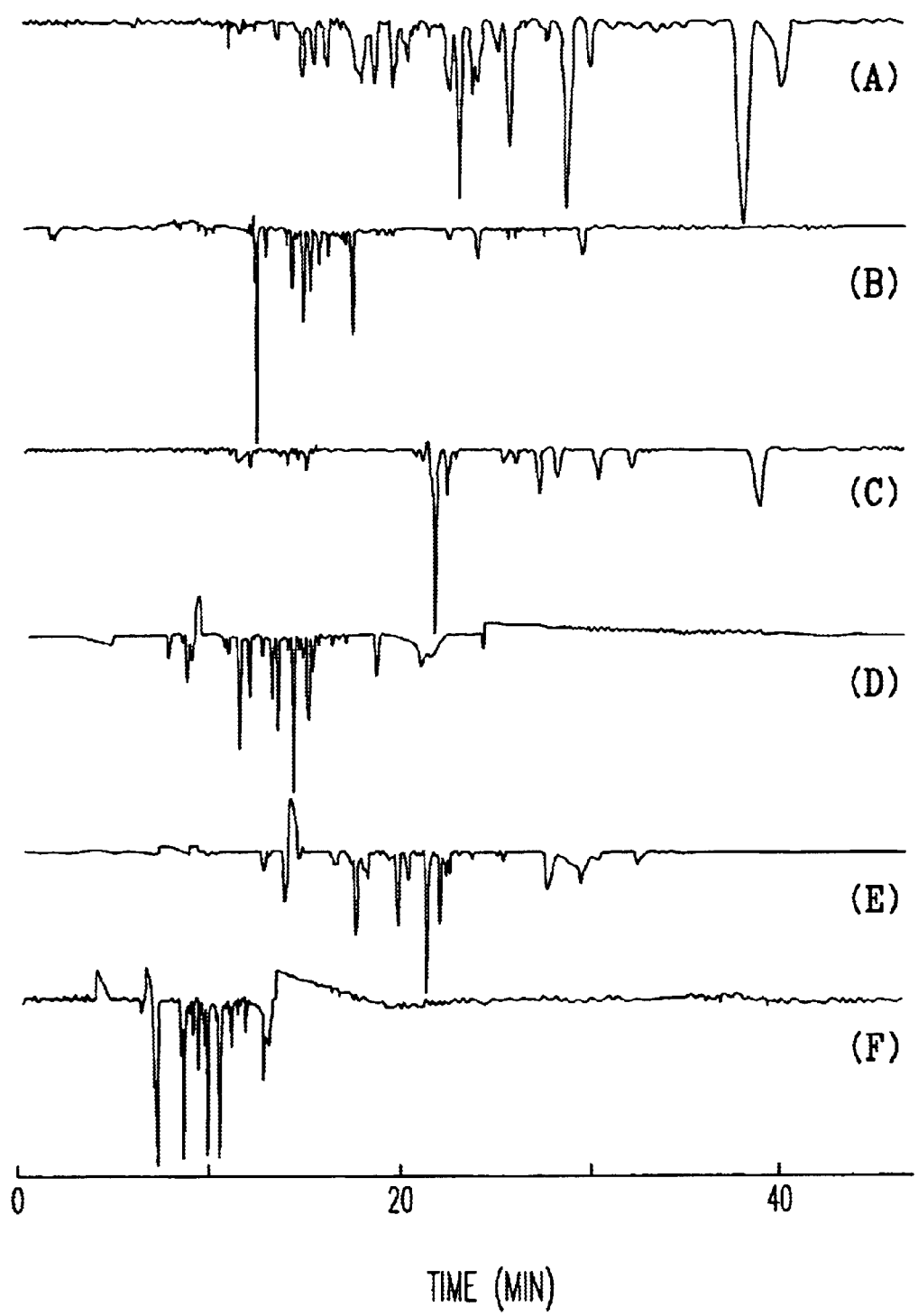
FIG. 14 shows selected electropherograms of BLOB extracted from the data in FIG. 12.

FIGS. 13 and 14 show the extracted electropherograms of BLGA and BLGB, respectively, as derived from the six-dimensional data in FIG. 12. The individual maps are virtually identical to the singlepillary results. The peptide patterns of BLGA and BLGB can be easily differentiated each of the six-dimensional separation conditions. Compared with the single-capillary run, 0.1% Tween 20 in 50 mM sodium acetate buffer (pH 5.0) gave slower migration times in the 96-capillary array. In part, this was due to the lower applied electric field (+157 vs. +227 V/cm). Tween 20 (0.1%), instead of Tween 20 (0.2%), at the MEKC condition was used in the array because the latter would have resulted in even longer analysis times.

Since peptides are polymers of amino acids, they typically have a limited number of charged states in their structure depending on the presence of amino acid moieties with ionizable side chains (Landers et al., *Handbook of Capillary Electrophoresis*, CRC Press (1997), pp. 219–221). This determines the pH ranges for CE separations beyond which no theoretical optimization can be performed. At pH <2, all ionizable groups of peptides will be protonated. The number of basic residues in the peptide chain will determine the overall charge-state of the molecule. At pH >10, all ionizable groups will be de-protonated, resulting in a negatively charged peptide. At these extreme pH conditions, the separation of peptides cannot be adjusted. At intermediate pHs, partly ionized termini and side chain residues allow optimization of the peptide separation. Therefore, four different pH conditions, i.e., pH 2.5, 5.0, 8.1, and 9.3, were selected for the separation of peptide fragments. Since ionization of peptides generally occurs over a pH range of 2.5–3.0, these pHs are sufficiently fair apart to give independent electropherograms but are close enough to form a continuous (combinatorial) set of conditions.

FIG. 15 shows typical peptide maps of BLGA and BLGB at four pH conditions for CZE using a single capillary after tryptic digestion, in which (A) is 0.1 M CHES/0.1 M NaOH (pH 9.3), (B) is 0.1 M Trizma®·Base/0.1 M tricine buffer (pH 8.1), (C) is 50 mM sodium acetate buffer (pH 5.0 with acetic acid), and (D) is 50 mM Trizma®·phosphae buffer (pH 2.5 with $H_3PO_4$). The applied electric field was +227 V/cm. Separation was at ambient temperature. A column, bare fused silica capillary with effective/total length of 50/75 cm and 50 µm i.d. was used. Hydrodynamic injection was conducted for 10 sec at 30 cm height. All peptide peaks at the four different separation conditions were well-resolved within about 30 min. Each condition revealed different peptide maps. The separation of peptides above pH 5.0 were completed quickly and efficiently within 15 min (FIG. 15A, B and C). The electropherograms at pH 2.5 showed good resolution in spite of a relatively long analysis time (FIG. 15D). Adsorption of the proteins on the capillary wall in CE can be a serious problem. This can lead to variable migration times, band broadening, and peak tailing. At pH 2.5, much of the negative charge had been titrated off the silica walls of the capillary such that there was little coulombic interaction between the peptide and the wall. This is not true of other pH conditions. Therefore, high ionic strengths were used in the running buffers to provide efficient separations because of reduced interaction between the peptide fragments and the capillary wall.

Figure 15A:
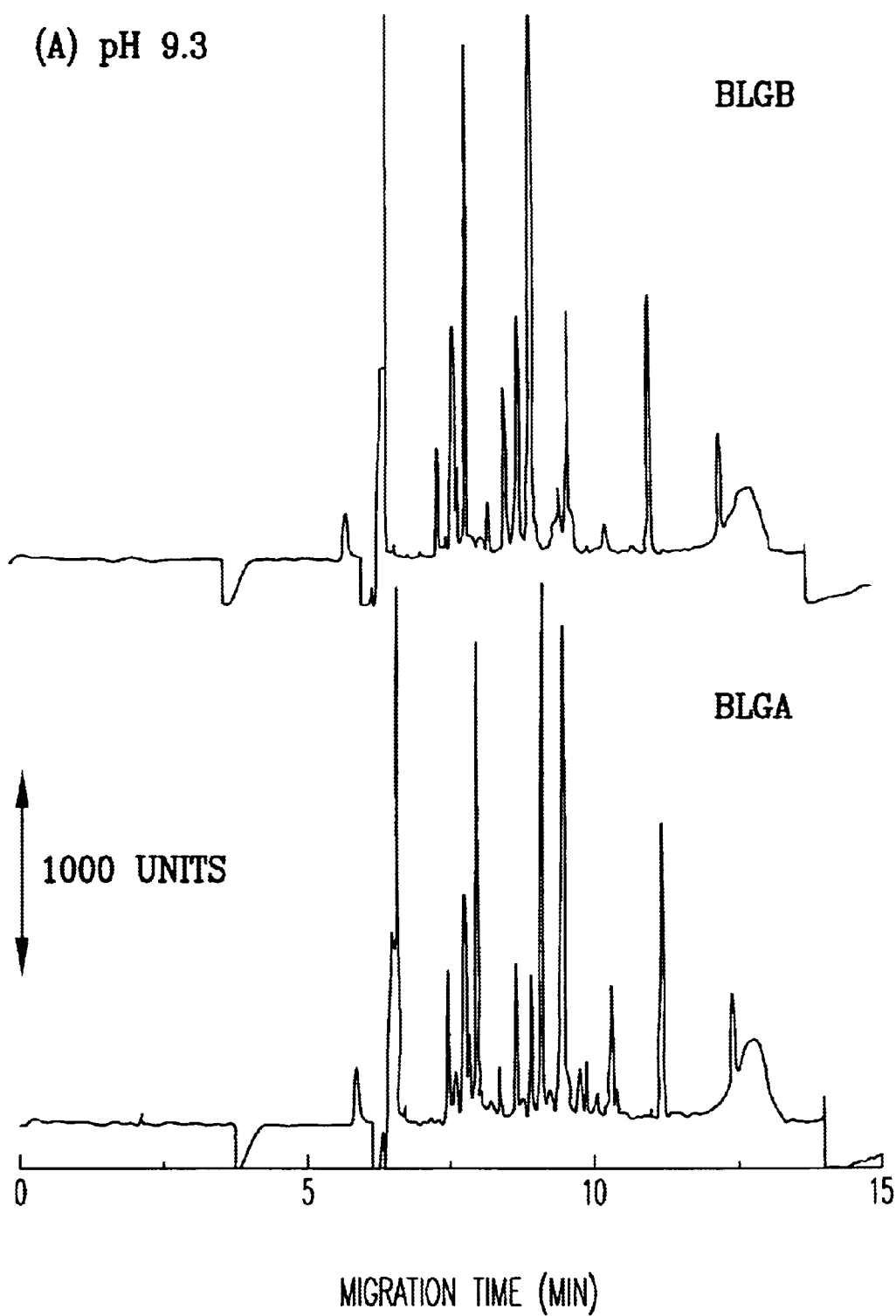
FIGS. 15A–D show typical peptide maps of BLGA and BLOB at four pH conditions (FIG. 15A at pH 9.3.
Figure 15B:
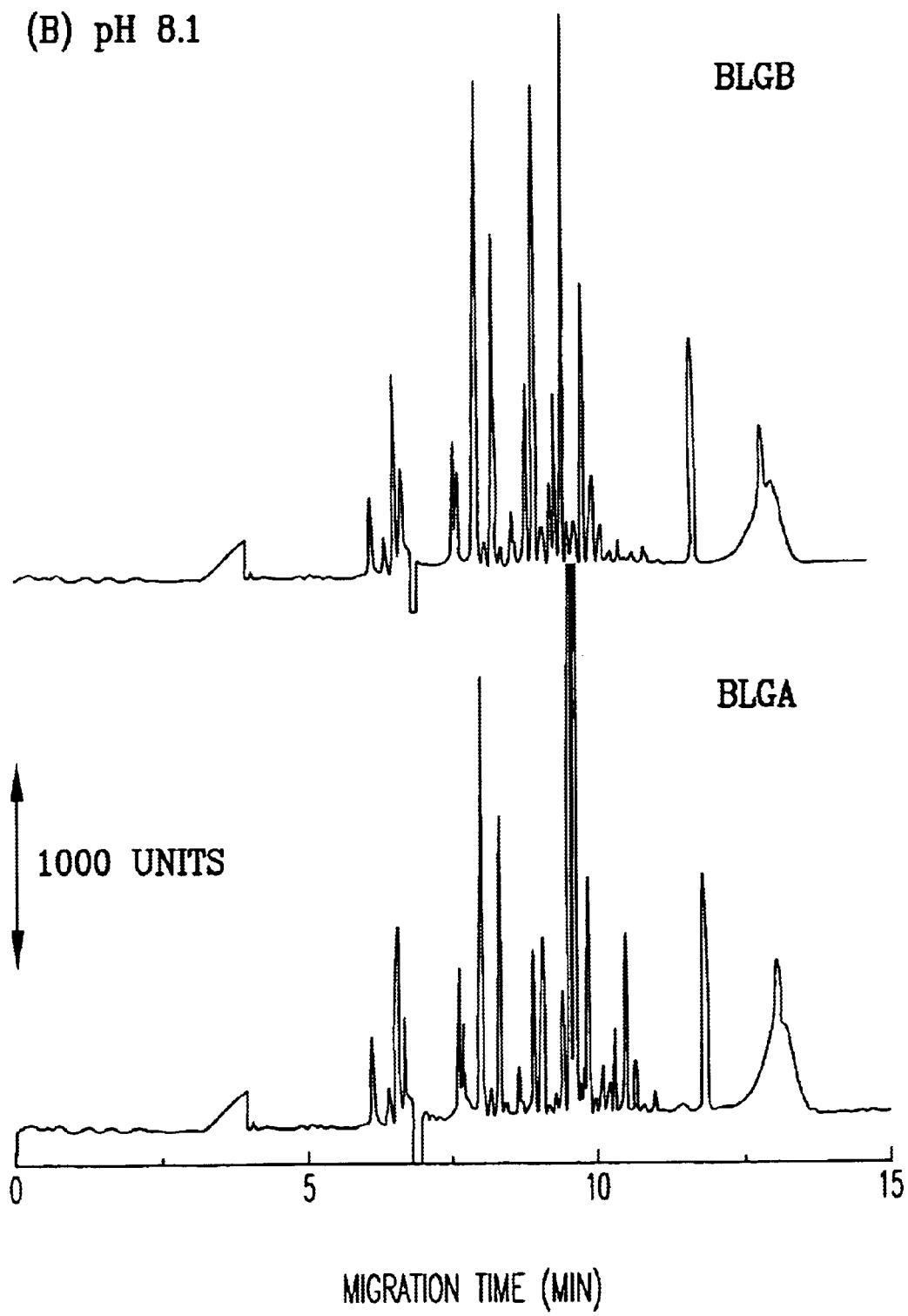

FIG. 15 (FIG. 15A at pH 9.3; FIG. 15B at pH 8.1; FIG. 15C at pH 5.0; and FIG. 15D at pH 2.5) shows the differences in the peptide maps of BLGA and BLGB at four different CZE conditions. Although the amino acid sequences of bovine BLGA and BLGB differ only at two sites (64 and 118, FIG. 11, SEQ ID NO: 11) among the 162 amino acids, the differences in the peptide fragments of BLGA and BLGB could be clearly identified. Peptide mapping by CE is incraingly being utilized as a complement, if not a viable substitute, for the already established technique of HPLC. CE has several advantages over HPLC, including much higher efficiency and a smaller sample requiremenl Moreover, CE also offers a straightforward correlation of migration time with physio-chemical properties. According to the dependence on pH, the net charges of each peptide fragment can be confirmed. nterprettion of the combined peptide maps at the four different conditions (FIGS. 15A–D) showed comprehensive data with overlapping redundancy for the peptides that cannot be obtained using only one separation condition.

Figure 16:
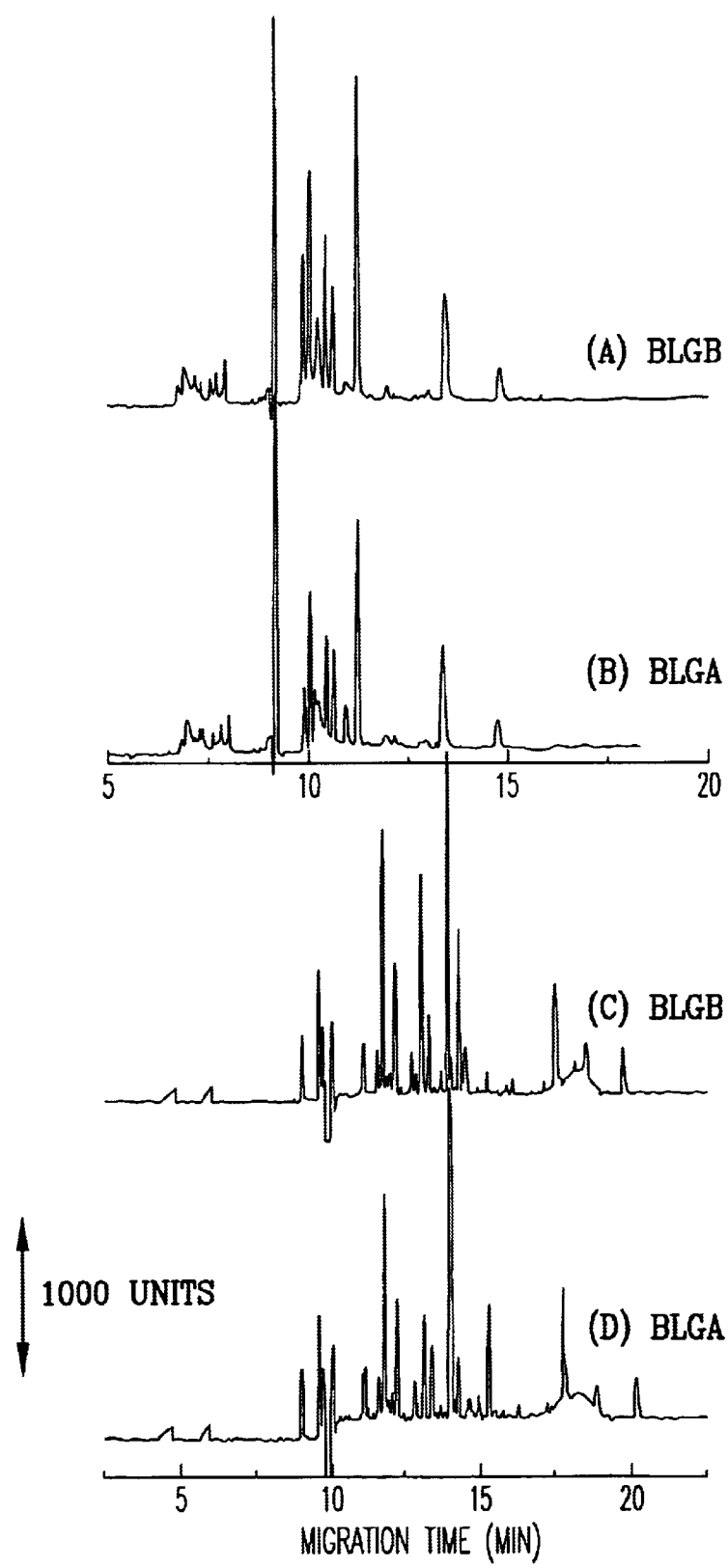
FIGS. 16 shows MEKC peptide maps of BLGA (B and D) and BLGB (A and C) obtained at two different MEKC conditions using a nonionic surfactant (A and B) and/or the combination of nonionic and anionic surfactant (C and D).

The addition of surfactants to the running buffer can add several new aspects to the separation mechanism. Above their critical micelle concentration, the surfactants form micelles, introducing a pseudo-stationary phase into the running buffer. FIG. 16 shows MEKC peptide maps of BLGA and BLGB obtaine at two different MEKC conditions using a nonionic surfactant, Tween 20 (i.e., 0.2% Tween, 20 in 50 mM sodium acetate buffer (pH 5.0 with acetic acid) (A and B), and/or the combination of nonionic and anionic surfactant, Tween 20+SDS (i.e., 7% Tween and 10 mM SDS in 0.1 M Trizima®·Base/0.1 M tricine buffer (pH 8.1) (C and D). The use of the surfactants in the intermediate-pH range was appropriate because more neutral peptides should exist there th at the extreme pHs such as pH 2 or 10.

Figure 15C:
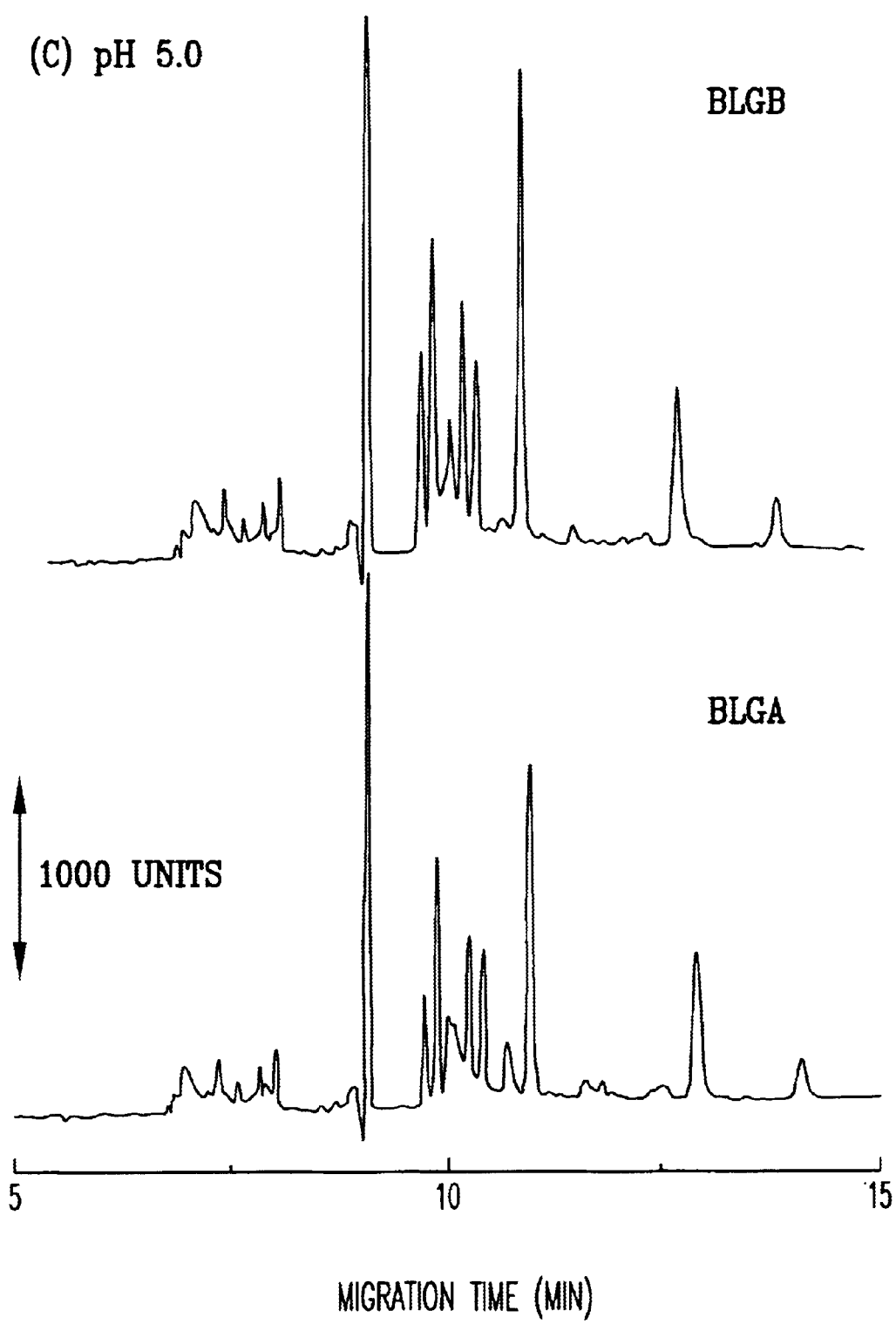
Figure 15D:
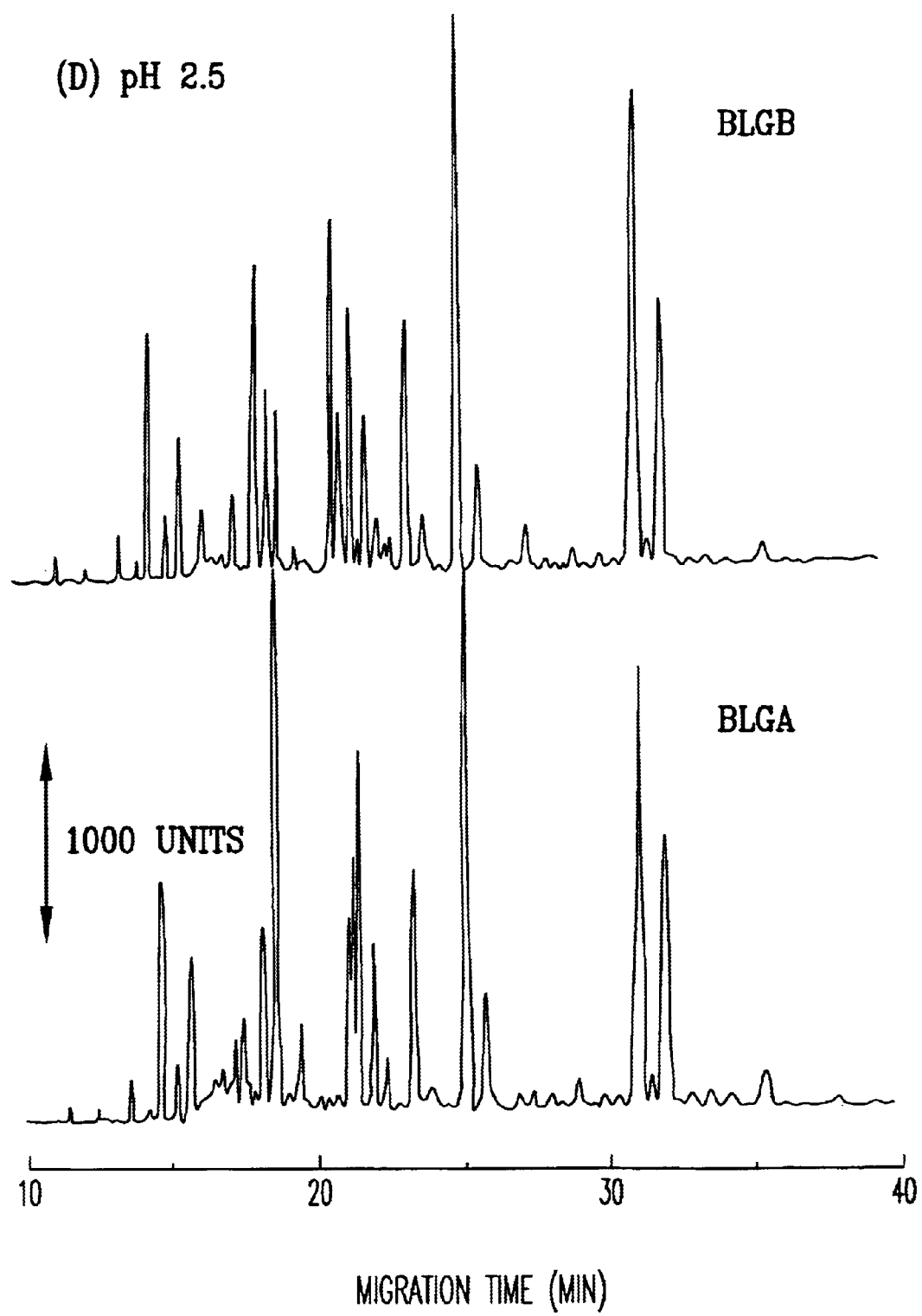

In the MEKC conditions using a nonionic surfactant (MEKC II conditions) (FIGS. 16, A and B), the electmpherogrnms showed higher resolution compared to the electropherogrmms obtained using CZE conditions (FIG. 15C). There are some minor shifts in relativepeu positions, mostly for the early eluting components. At pH 5.0, as the concentration of the nonionic surfactant Tween 20 is increased, the resolution of peptide fragments increased without an increase in the current. Although all of the peptide fragments showed baseline separation above 0.3% Tween 20, the analysis time was approximately 1 hr. Under the applied electric field of +227 V/cm, 0.2% Tween 20 was sufficient to improve the resolution compared to CZE. This buffer was selected so that the analysis time can be kept under 20 min.

Figure 17:
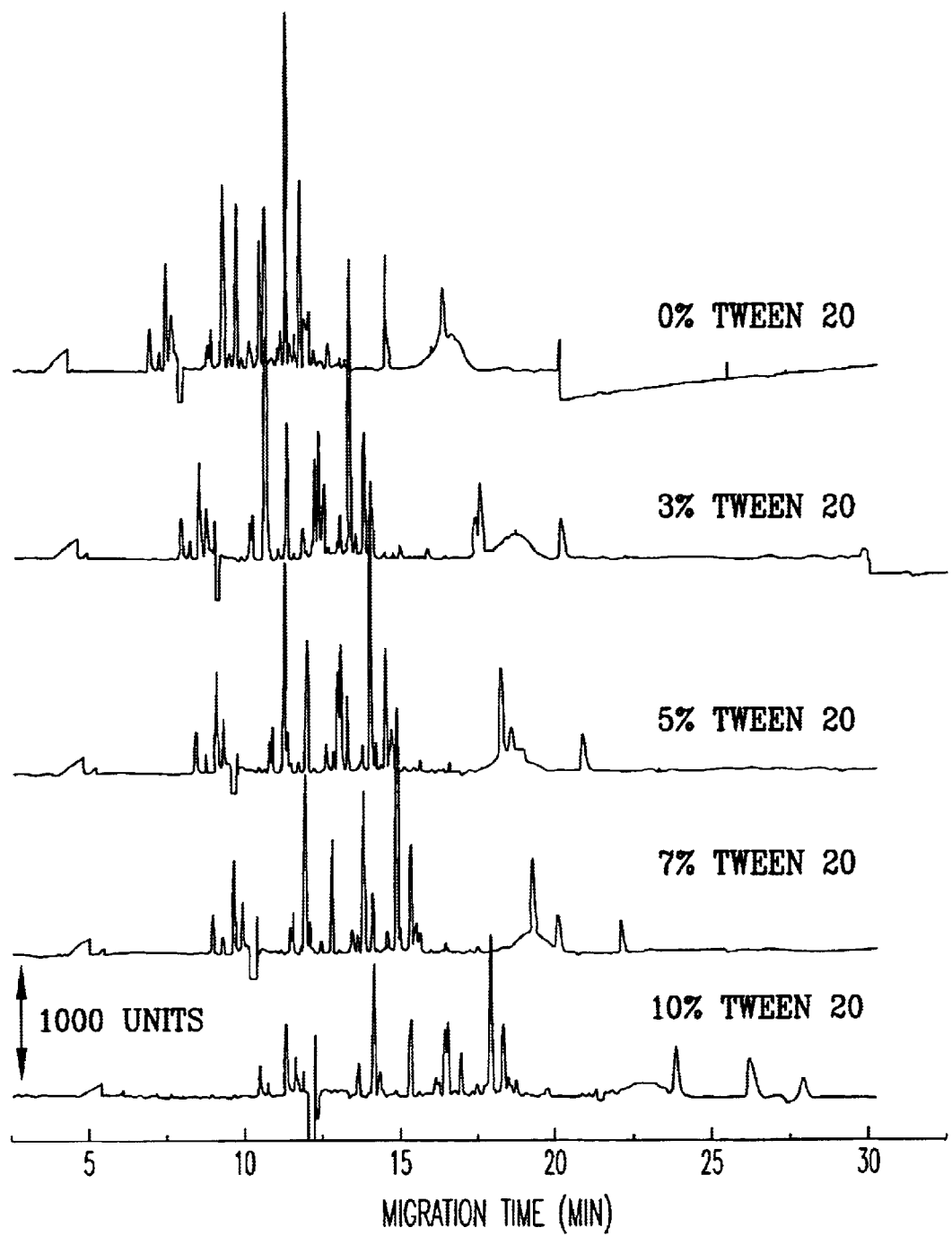
FIG. 17 shows the effect of Tween 20 concentration at pH 8.1 on the MEKC peptide maps for BLGB in terms of migration time (min).

In the MEKC conditions using the combination of nonionic and anionic surfactants (MEKC II conditions) (FIG. 16, C and D), the higher concentration of Tween 20 and the anionic surfactant SDS were needed to increase the resolution. Because higher pH caused larger mobilities for the peptide fragments in solution, a lower frequency of dynamic partition into the micelles resulted. However, as the concentration of surfactants in the running buffer is increased to favor partition, the analysis time also increased and the sensitivity decreased. So, 7% Tween 20 and 10 mM SDS were chosen as optimal surfactant concentrations for MEKC II. The unique advantage of combining Tween 20 and SDS led to the full resolution of all peptide fragmnts, enabling higher resolution for both neutral peptides and same-charged peptides. FIG. 17 shows the effect of Tween 20 concentration at pH 8.1 on the MEKC peptide maps of BLGB in terms of migration time (min). It is clear that both resolution and selectivity are affected by the surfactant. The patterns of the peptide mnaps obtained at the six different CE conditions above (FIGS. 15 and 16) were reproducible as judged by comparing the results of five repeated injections in each case.

This example demonstrates high-throughput, multi-dimensional peptide mapping of proteins in accordance with the present invention, such as by using multiplexed capillary electrophoresis. Unique fingerprints of closely related sample proteins, BLGA and BLGB, on a 96-capillary array with six different separation conditions were obtained withi 45 min. The 214-nm monitoring of peptide bonds is univesal but also very complex because a typical map generally contains 20–150 peaks (Dong et al. (1992), supra) and all of the fragments should ideally be totally resolved. Maps of unknown proteins are not unambiguous by using only one- or two-dimensional separation. With six complementary separation conditions, there is no need to reoptimize the protocol for each new sample. The instrumental set-up is simplified and automation of the method becomes possible. Most importantly, this multi-dimensional and multiplexed peptide mapping technique is inherently a small-volume and high-throughput approach. For example, although only two proteins are sdied here, sixteen different prroteins can be mapped at the same time starting with $\mu$l samples. Alternatively, different enzymes or chemical agents can be employed to provide complementary sets of peptide maps for further confirmation. For complex unknown samples, internal standards can be used to normalize the migration times and peak areas (Xue et al. (1999), supra; and Gong et al. (1999), supra). The six separaton conditions then can be used to rank order the peptide fragments with respect to their isoelectric points (pIs), very much like a high-resolution gradient elution. The use of different sets of buffer systems in each capillary in the array is in effect a combinatorial approach to developing the best separation conditions for a given group of analytes. This las feature should be generally useful in all applications of CE. Finally, capillary arrays are compatible with on-column digestion of proteins (Chang et al., Anal. Chem. 65: 294–2951 (1993)) so ftha fuill automation in multiple channels (Chang et al. (1992), supra; Zhang et al. (1999), supra; and Zhang et al., Anal. Chew. 71: 1138–1145 (1999)) is possible with sub-microliter volumes of samples and reagents.

Example 4

This example demonstrates the use of the present invention in combinatorial screening of enzyme activity.

The multiplexed capillary system described above was used. A total of 96 fused-silica capillaries (50-$\mu$m i.d., 150-$\mu$m o.d.; Polymicro Technologies, Phoenix, Ariz.) packed side by side with 50cm effective length and 70-cm total length were used for separating reactants, products and enzymes. Preloaded (0.2 ml) 96-well plates were used regulars for carrying out the enzyme reactions. A 254-nm mercury lamp was used for UV absorption detection. A voltage of +11 kV (~157 V/cm) was applied across the capillaries for separation.

During the period of incubation, the plates were covered by plastic film to minimize evaporation of the reaction solution. This allowed the concentrations of enzyme and substrate to remain as stable as possible.

Because of the inhibition of pyruvate on the catalysis of LDH, an optimal concention of pyruvate is important At pH 7.2 and 25° C., 2 mM pymvate is normally suitable for the $M_4$ isoenzye. So, in the reaction buffers (20 mM phosphate, pH ranges from 5.8~8.0), 2.0 mM NADH and ~2.0 mM pyruvate were added as the substrates for the enzymatic reaction. The direction of reaction was chosen as follows:

$$\text{NADH} + \text{pyruvate} \xrightarrow{\text{LDH}} \text{lactate} + \text{NAD}^+.$$

The reaction was allowed to proceed for a fixed period prior to hydrodynamic injection of the reactants, products and enzymes into the capillaries. A solution of 10 mM phosphate with pH of 8.0 was used as the separation buffer. After applying voltage, all components were readily separated due to different mobilities. Since low concentrations of enzyme ($5\times10^{-10}$~$1\times10^{-8}$ M) (pseudo-first-order Jon) were used, the amount of NAD$^+$ formed during a given period of time at a fixed temperature is linearly proportional to the LDH activity. Therefore, the LDH activity can be quantified by measuring the area of NAD$^+$ formed during the fixed incubation period. The areas of the NAD$^+$ peak and the NADH peak were integrated. Because NAD$^+$ and NADH both absorb at 254 nm, while the enzyme does not contribute much to the background at this wavelength, a 254-nm mercury lamp was used. By measuring the absorption coefficients of NAD$^+$ and NADH at 254 nm in a conventional spectrophotometer, the peak areas were converted to amounts. The ratio between the NAD$^+$ amounts formed and the original NADH amounts was calculated. Since a small background reaction exists, blank reactions were monitored and subtracted.

Separate 20 mnM phosphate buffers with pH values of 5.8, 6.3, 6.5, 6.7, 7.0, 7.3, 7.6 and 8.0 were prepared. Buffer solution (175 $\mu$l), 10 $\mu$l enzyme solution, 10 $\mu$l 40 mM NADH and 5 $\mu$l 90 mM pyruvate were added into 96 wells for reaction. Reactions progressed at room temperature. The various final concentrations of enzyme in those solutions were $5\times10^{-10}$ M, $2\times10^{-9}$ M, $3\times10^{-9}$ M, $4\times10^{-9}$ M, $5\times10^{-9}$ M, $6\times10^{-9}$ M, $7\times10^{-9}$ M, $8\times10^{-9}$ M and $1\times10^{-8}$ M. Thus, for every concentration of enzyme, there were 8 different buffer solutions. At the same time, for every buffer solution with a different pH value, there were 9 different concentrations of the enzyme. The reaction mixtures were incubated for 30 min, 78 min, 128 min, 180 min, 308 min, 420 min, 480 min and 1,477 min. After each incubation period, hydrodynamic injection was used to initiate CE analysis. The volumes withdrawn each time from the reaction vials were negligible compared to the starting volumes. Therefore, essentially non-intrusive monitoring was achieved.

Figure 18A:
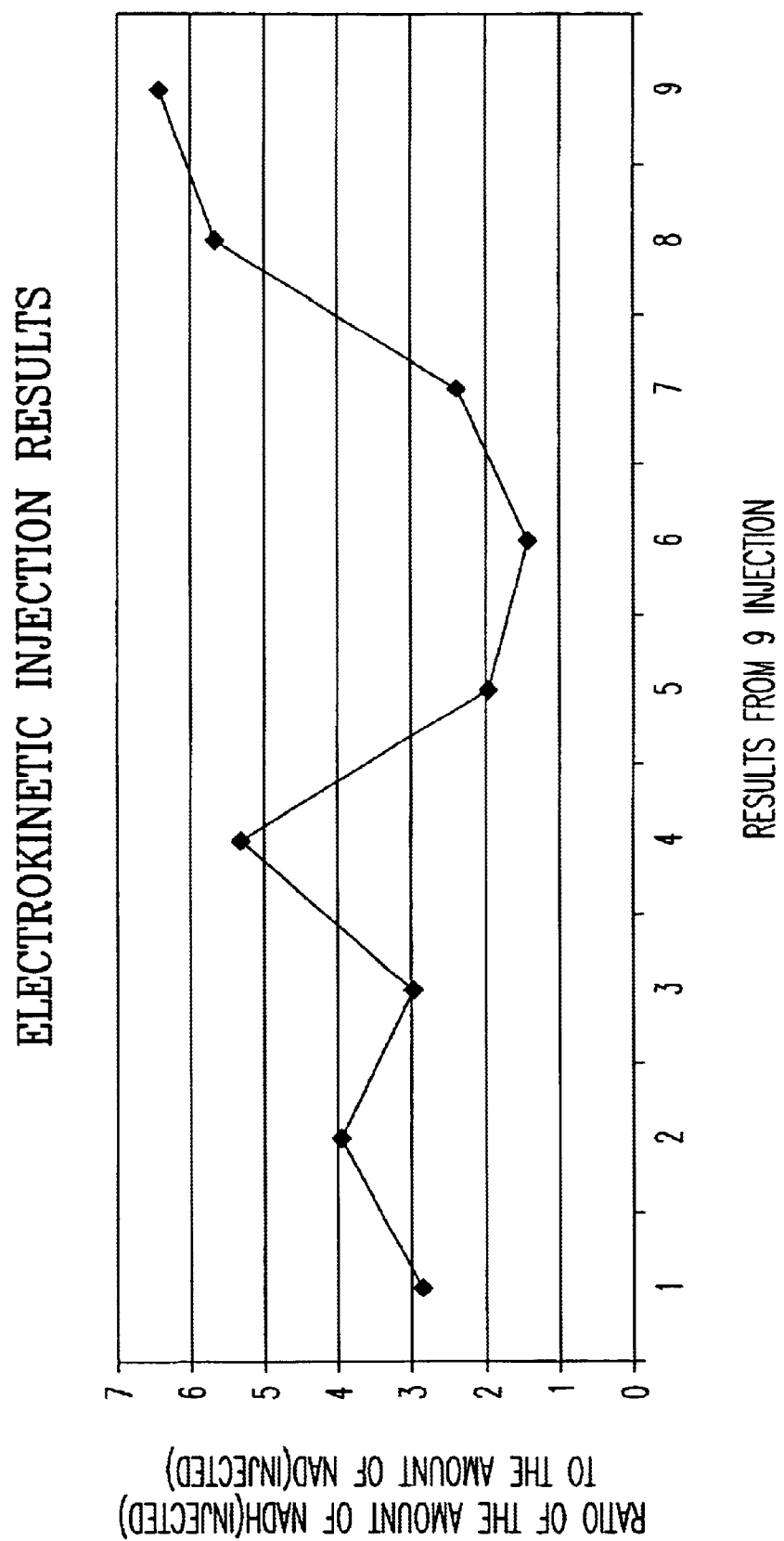
FIG. 18A is a graph of the ratio of the amount of NADH (injected) to the amount of NAD (injected) vs. the results from nine electrokinetic injections.
Figure 18B:
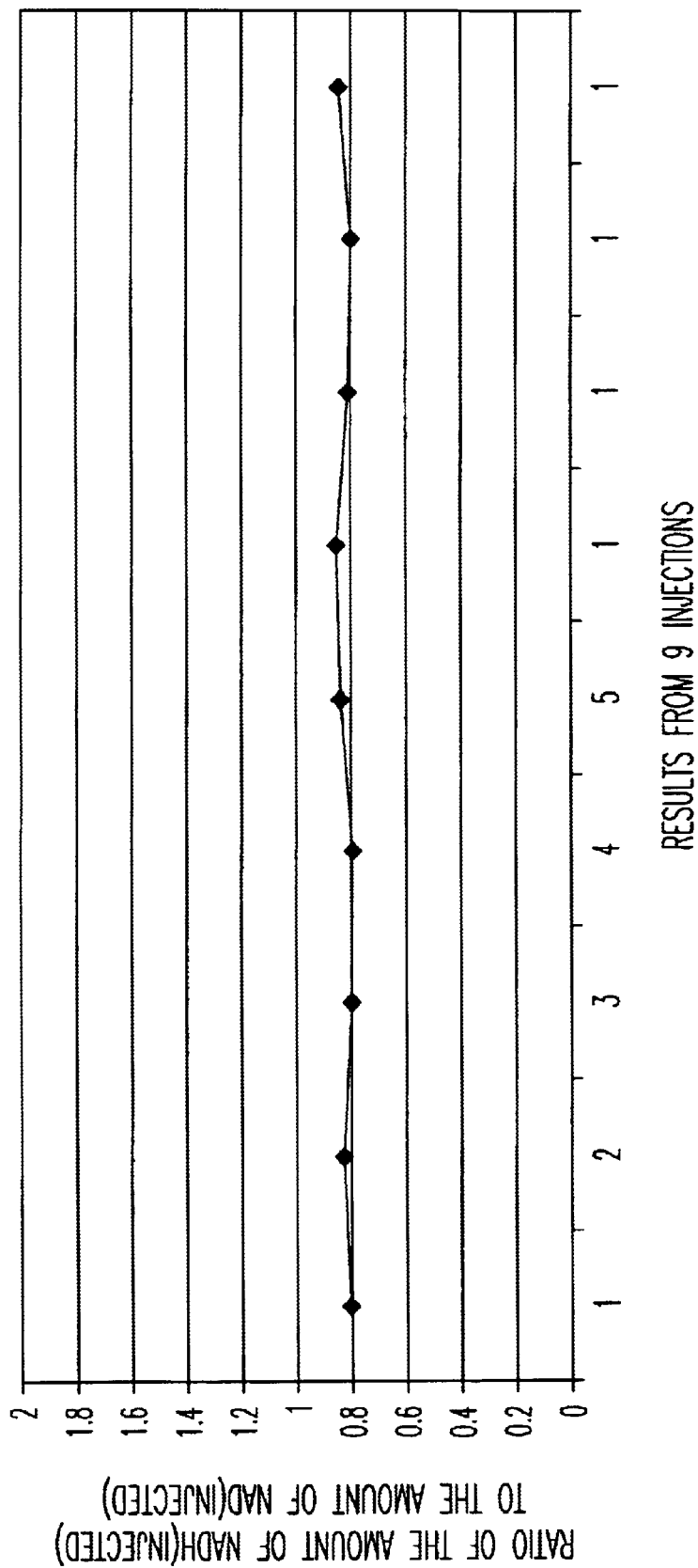
FIG. 18B is a graph of the ratio of the amount of NADH (injected) to the amount of NAD (injected) vs. the results from hydrodynamic nine injections.

The reason for using hydrodynamic injection is that electrokinctic injection would have caused serious errors. This is because of different surface conditions from capillary to capillary, different compositions of the buffer solutions, different capillary temperatures, and different migration velocities of NADH and NAD$^-$ (Lee et al., Anal. Chem. 64: 1226–1231 (1992)). The effect is obvious from a comparison of FIG. 18A, which is a graph of the ratio of the amount of NADH (injected) to the amount of NAD (injected) vs. the rults from nine electrokinetic injections, and FIG. 18B, which is a graph of the ratio of the amount of NADH (injected) to the amount of NAD (injected) vs. the results from nine hydrodynamic injections. There, a solution with 1 mM NADH and 1 mM NAD$^+$ was prepared and injected separately by hydrodynamic injection and electrokinedic injection into 9 different capillaries. A 5 cm difference in height was maintained for 60 sec for the former and +11 kV was applied for 30 sec for the latter. By applying +11 kV to the capillaries, the NADH and NAD$^+$ sample zones were separated and driven across the detection windows. Since all of the solutions had the same NADH and NAD$^+$ concentrations, identical peak areas were expected for the NADH peaks and NAD$^+$ peaks. According to FIG. 18, hydrodynamic injection only caused a very small standard deviation (SD), which was about 0.027 with a mean of 0.817, while electokinetic injection caused serious errors, with an SD of 0.483 and a mean of 3.66. Such an injection problem is more serious in capillary arrays compared to repeated injections in a single capillary because of surface heterogeneity.

The migration times varied from capillary to capillary, because the conditions of the capillaries were different. Despite the different migration times, the NADH and NAD$^+$ peaks were easily identified in this simple mixture. These peak areas were used for quantitation. After each incubation period, the fraction of NADH converted to NAD$^+$ was calculated using the following equations:

$$\text{amount of } NADH \text{ (reacted)} = NAD^+ \text{area} \times \frac{\varepsilon_{NADH}}{\varepsilon_{NAD^+}}$$

$$\text{fraction of } NADH \text{ (reacted)} = \frac{\text{amount of } NADH \text{ (reacted)}}{\text{amount of } NADH \text{ (reacted)} + NADH \text{ area}}.$$

Figure 19:
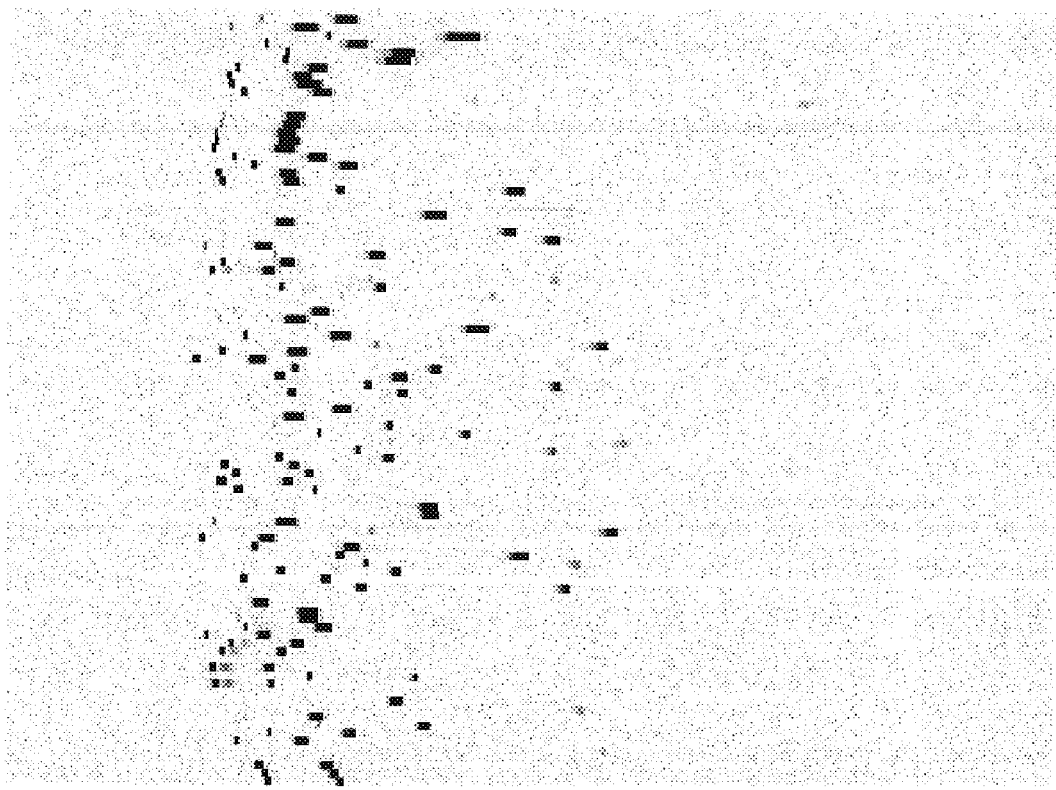
FIG. 19 is a reconstructed absorption image of combinatorial screening of enzyme activity in a 96 capillary array in which the capillaries (1–96) are displayed from top to bottom and migration time (0–33 min) is plotted from lefi to right.

As stated before, the fraction of NADH (reacted) then could be used to represent the activity of the enzyme whenever this reaction is pseudo-first-order. The use of a ratio avoids problems with variations in detection sensitivity and injected amounts among capillaries. Additonal corrections for the different speeds of the analytes passing the detector were nude since hydrodynamic injection was employed (Lee et al. (1992), Since 8 pH conditions and 9 enzyme concentrations were screened, there were a total of 72 channels (capillaries) where products were detected. In addition 16 channels of background reaction (8 pH conditions with substrates but no enzymes) were monitored. The other 8 channels in the ar=ay were filled with the buffer (no substrate and no enzyme) as the absorption reference. The entire data set for the 96-capillary array is shown as a reconstructed image in FIG. 19, which is a reconsructed absorption image of combinatorial screening of enzyme activity in a 96 capillary array in which the capillaries (1–96) are arnged from top to bottom and migration time (0–33 min) is plotted from left to right. The change in electroosmotic flow from one capillary to the next and temperature variations are the main reasons for substantial variations in migration times among the channels. Even larger variations are expected because the sample pH and sample ionic strengths are all different. The capillary walls will become dynamically altered as a result of injection. internal standards can be employed to normal the migration times, but were not needed for the simple electropherograms in this study. The intensity variations in FIG. 19 are partly due to uneven illumination but mostly due to the expected variations in the extents of reaction in each channel.

Figure 20:
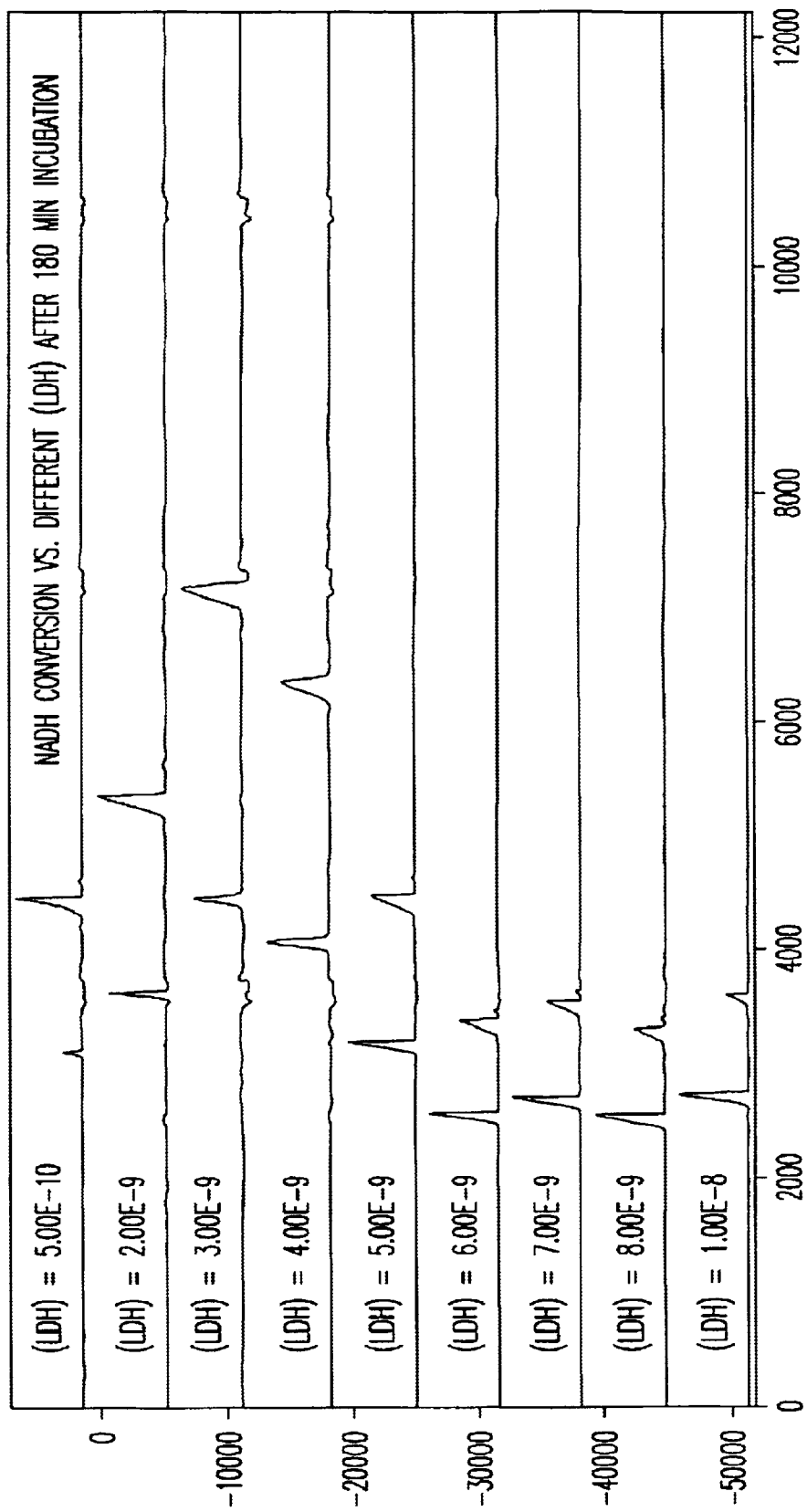
FIG. 20 is an electropherogram of products after 180 min reaction for different LDH concentrations at pH=7.
Figure 21:
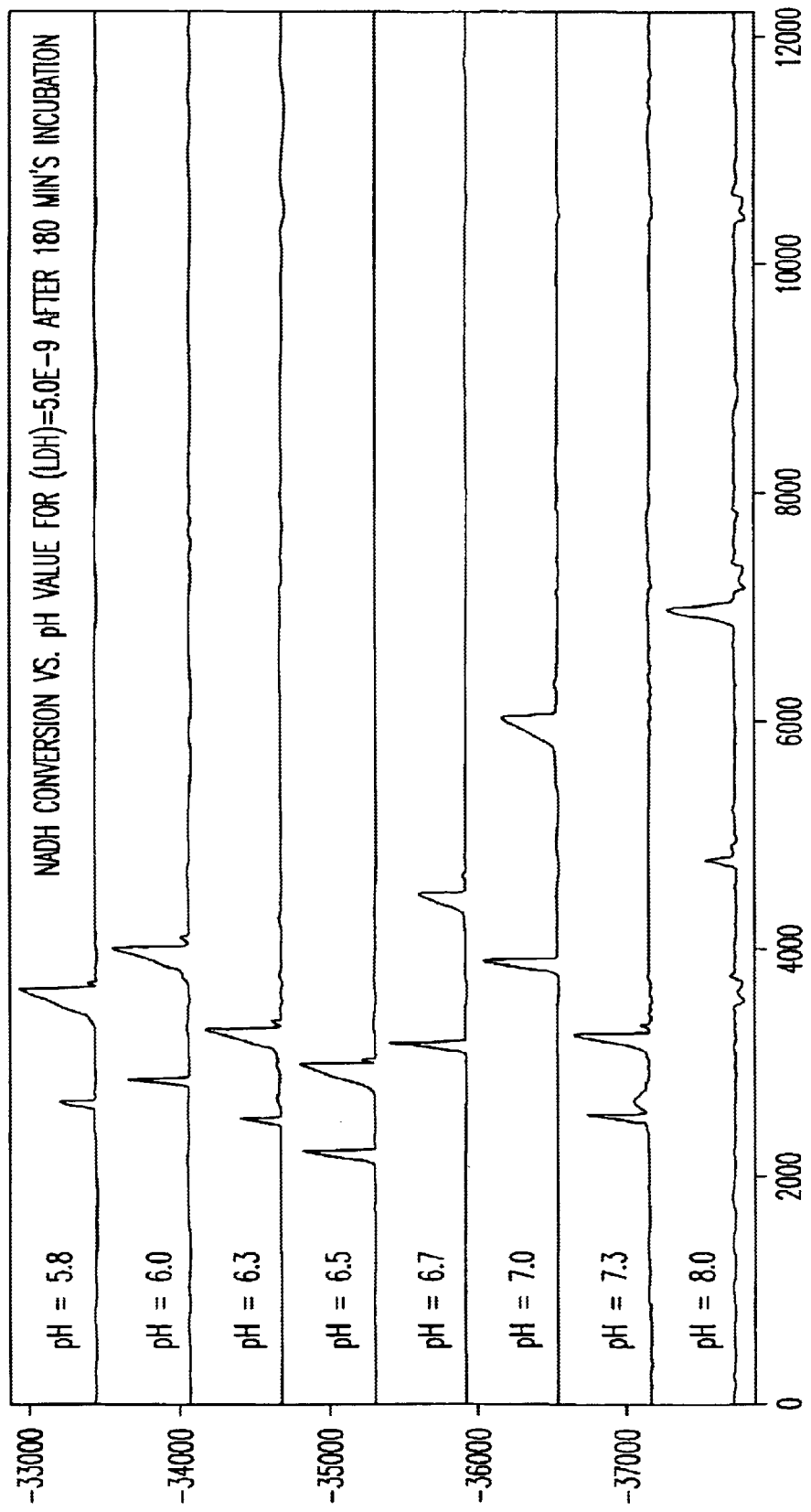
FIG. 21 is an electropherogram of products after 180 min reaction for different pH at an LDH concentration of $5 \times 10^{-9}$ M.

Extracted electropherograms for activity screening are shown in FIGS. 20 and 21. At a constant pH FIG. 20), it is easy to see that the extent of reaction increases with LDH concentration (left peak is NAD (product); right peak is NADH (reactant); from top to bottom, the concentrations are 0, 0.5 nM, 2 nM, 3 nM, 4 nM, 5 nM, 6 nM, 7 nM, 8 nM and 10 nM; the enzyme is not detected at this concentration). At a fixed LDH concentration, i.e., 5×10$^{-9}$ M (FIG. 21), it can be seen that there is an optimum pH where the LDH activity is the highest (left peak is NAD$^+$ (product); right peak is NADH (reactant); from top to bottom, the pH are 5.8, 6.3, 6.5, 6.7, 7.0, 7.3, 7.6 and 8.0; the enzyme is not detected at this concentration).

Figure 22:
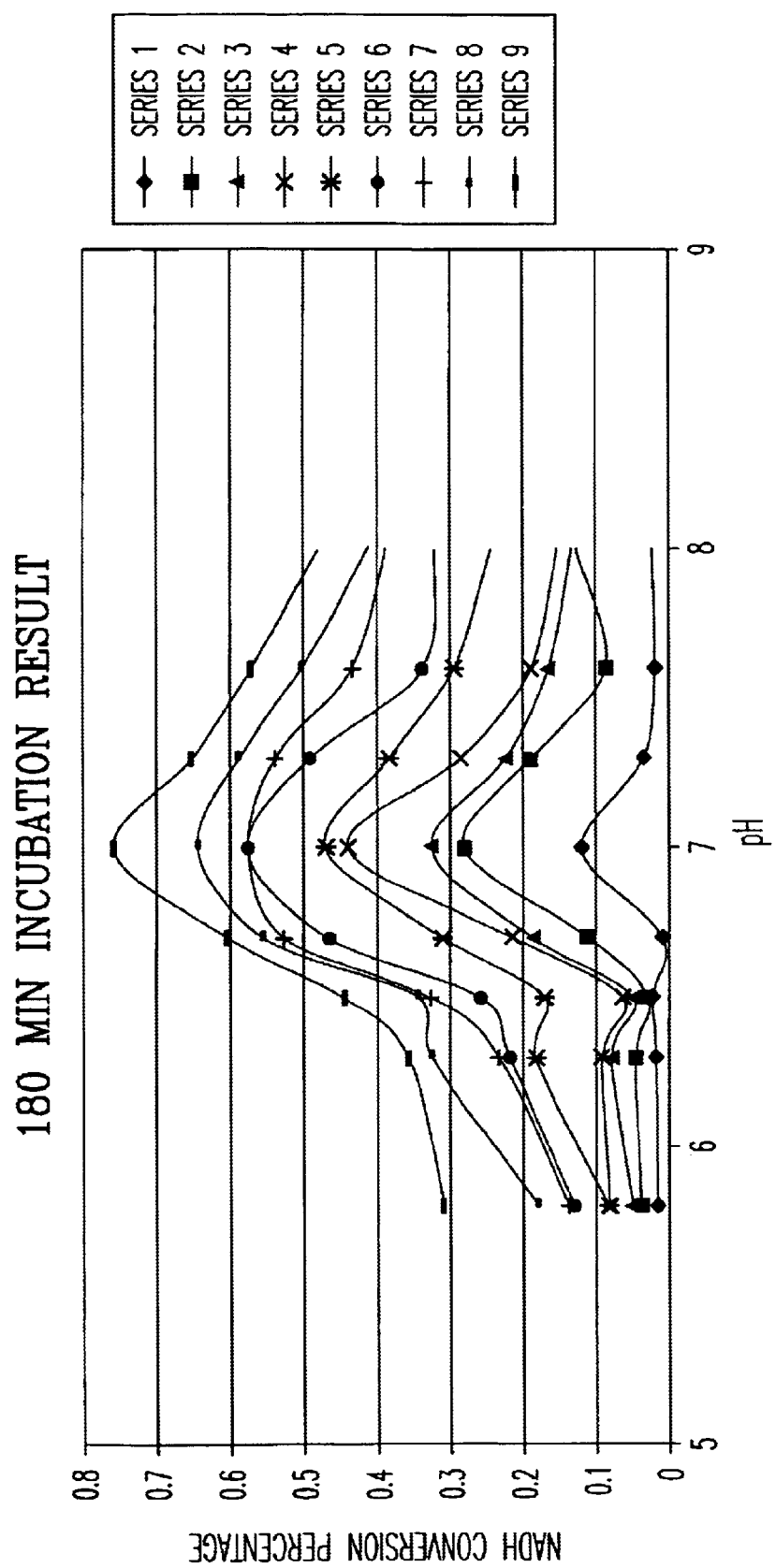
FIG. 22 is a graph of NADH conversion percentage vs. pH for series 1–9 at 180 min incubation.
Figure 23:
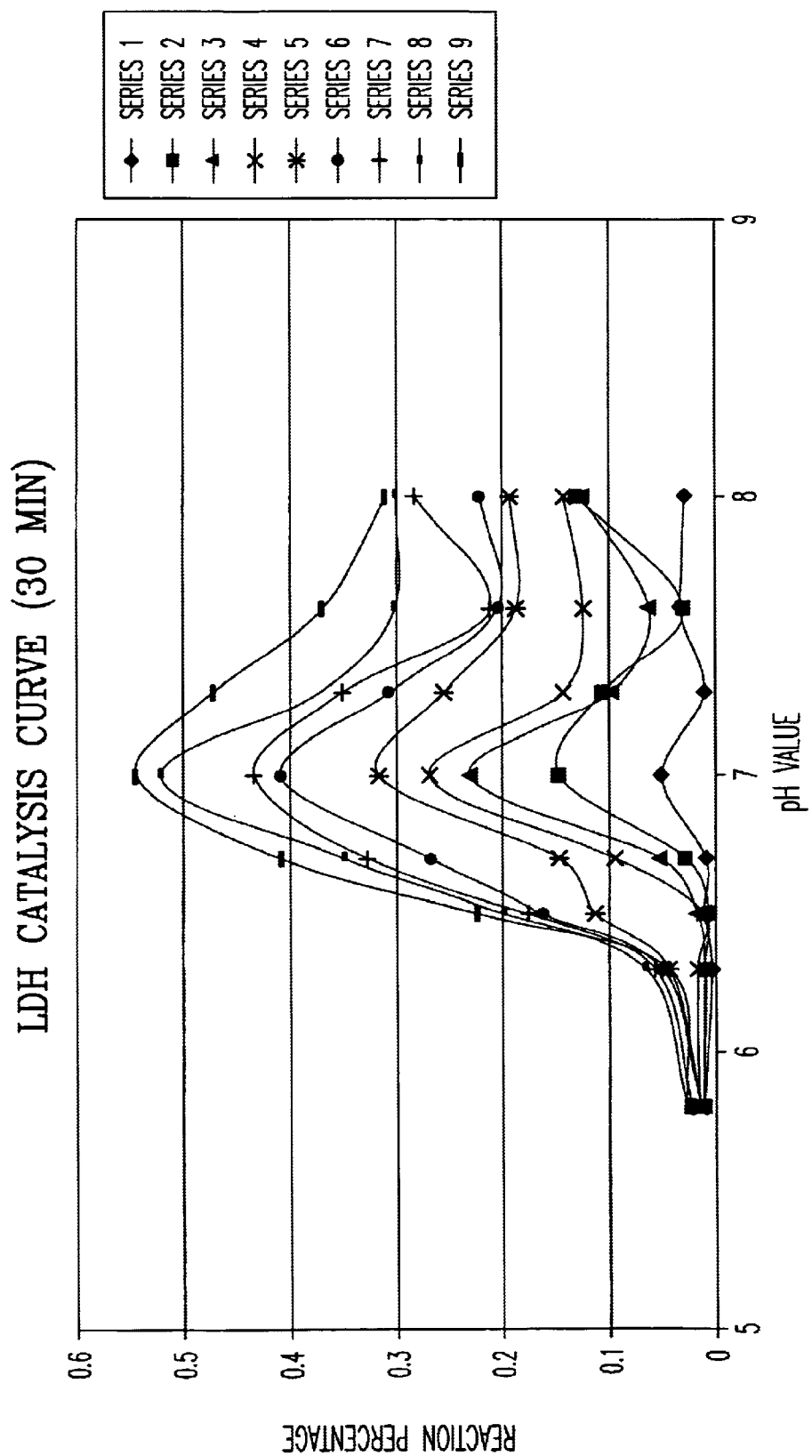
FIG. 23 is a graph of reaction percentage vs. pH for series 1–9 for 30 min of LDH catalysis.
Figure 24:
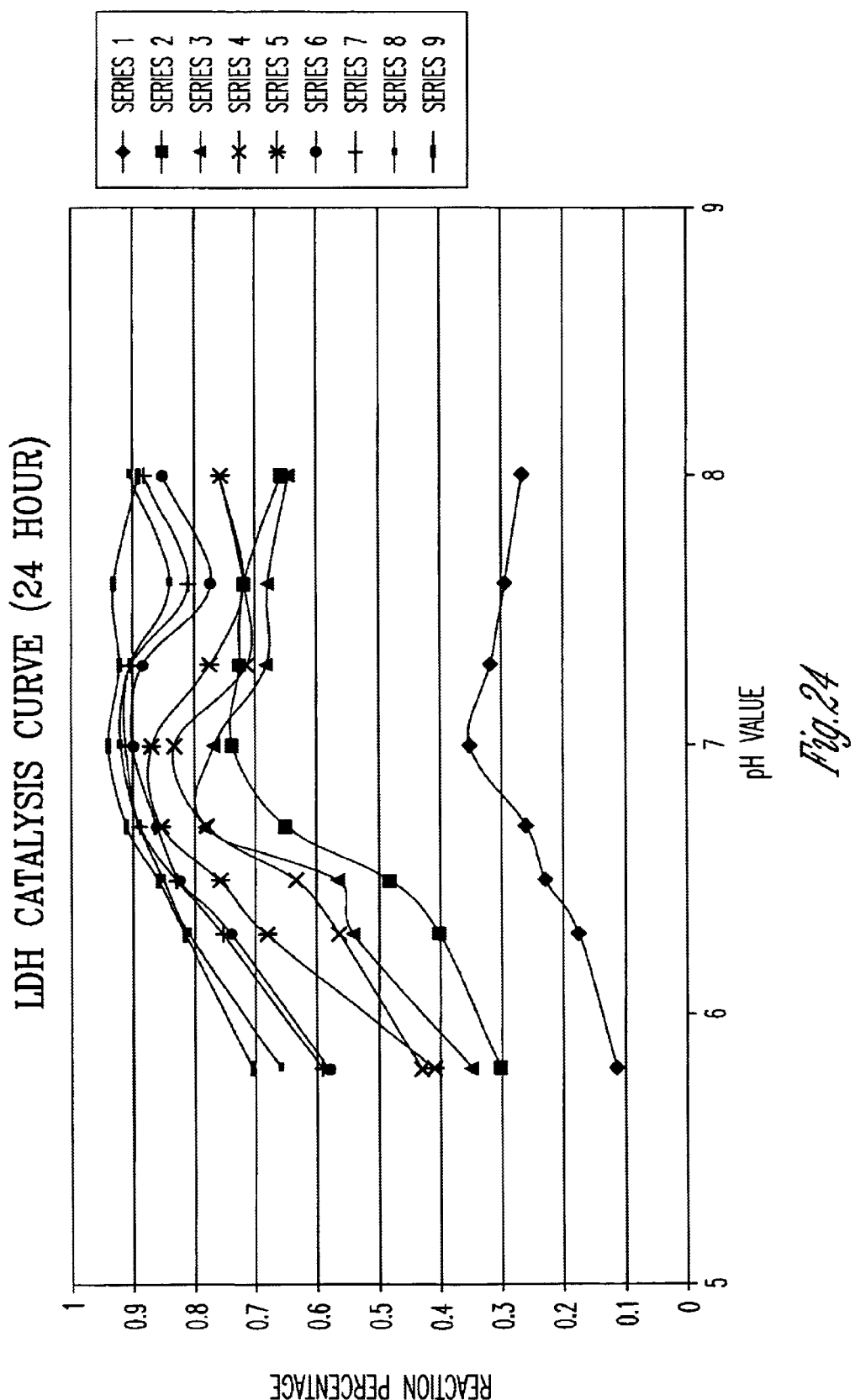
FIG. 24 which is a graph of reaction percentage vs. pH value for series 1–9 for 24 hr of LDH catalysis.

The quantitative optimization results shown in FIG. 22, which is a graph of NADH conversion percentage vs. pH for series 1–9 at 180 min incubation, need to be examined more carefully by repeated sampling of the reaction mixture at well-defined time intervals. For short reaction times (FIG. 23, which is a graph of reaction pertentage vs. pH for series 1–9 for 30 min of LDH catalysis), there is a linear increase in the extent of reaction as a function of LDH concentration for all pH conditions. This is ideal behavior. For long reaction times (FIG. 24, which is a graph of reaction percentage vs. pH value for series 1–9 for 24 hr of LDH catalysis), nonlinearity is observed, especially when the fraction reacted exceeds 0.6. The reason for this is saturation of the reaction When a significant frction of the reagent (NADH) is consumed, the pseudo-first-order reaction description fails. The remedy is to use higher reagent concentrations or to stay with short reaction times. This feature shows the importance of monitoring the full kinetics of reactions as opposed to single-point monitoring. FIG. 24 by itself would have led to the incorrect conclusion that there is not much difference in enzymatic activity over a broad pH range.

Example 5

This example demonstrates the use of the present invention in combinatorial screening of homogeneous catalysis and the optimization ofa homogeneously catalyzed synthetic organic reaction.

The present inventive method was used to analyze a new palladium-catalyzed annulation reaction (Zhang et al., *J. Organometal. Chem.* 576:111–124 (1999)), which readily affords γ-carbolines, noteworthy for their biological activity. The optimal reaction conditions and the regiochemistry for this type of annulation are generally highly dependent on the nature of the palladium catalyst and the base employed. Previous efforts to optimize this process employed 5% Pd(OAc)$_2$, 10% PPh$_3$ and Na$_2$CO$_3$ as base and afforded a 1:1 ratio of isomers A/B in essentially a quantitative yield.

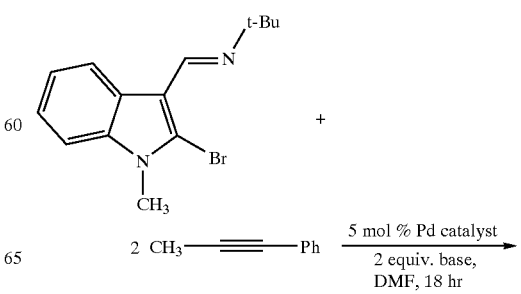

-continued

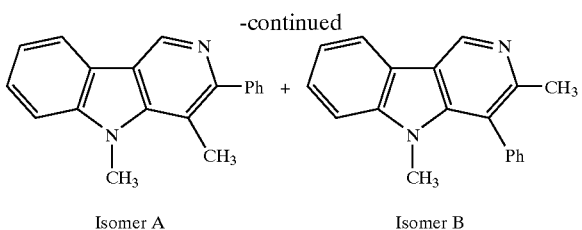

Isomer A     Isomer B

Figure 25:
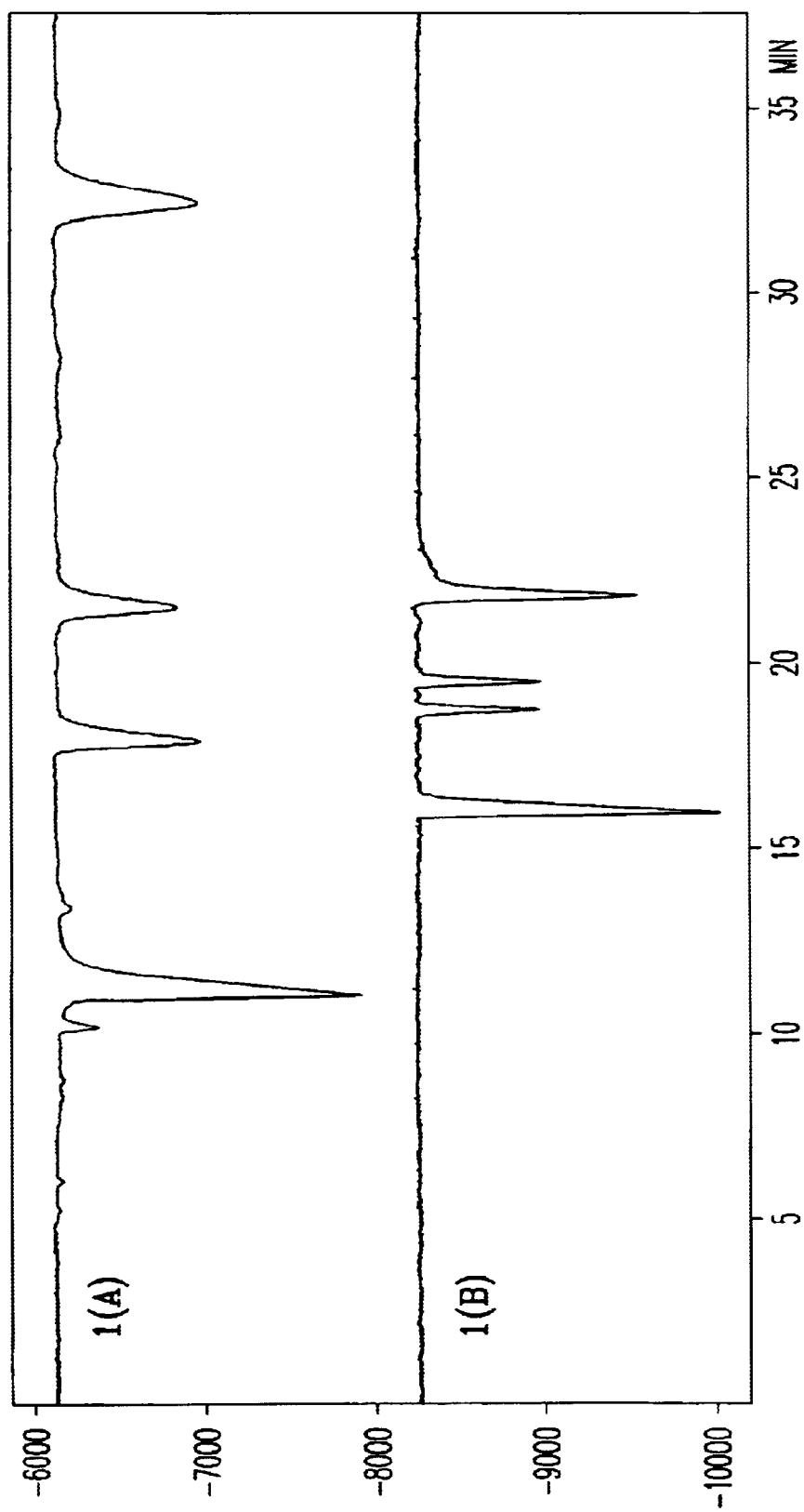
FIG. 25 shows the separation of two isomeric forms (A and B) of the product from the reagents and the internal standard using two different buffers (1a and 1b).

The nature of this and other catalytic reactions is that a lot of parameters can affect the yield and "optimum" conditions are often found by trial and error. The above reaction was run using 0.25 mmole in 5 ml of dimethyl fornamide (DMF). The volume was reduced to 120 μl by using 6 mm O.D. glass tubes sealed at one end and arranged in a 96-well format. The individual components were added as a DMF solution or as a slurry by pipetting. Septums were used to cap the reaction tubes to prevent evaporation. All reactions were thus run on a 5 μmole scale. Heating was provided by a dry heat bath kept at 110° C. As an internal standard, 1 μmole of norhanman was added to the reaction mixture. No catalytic effect on the system from the addition of the norharman was observed in control experiments. FIG. 25 shows the separation of the two isomneric forms (A and B) of the product from the reagents and the internal standard using two different buffers (40 mM $NH_4OAc$ and 0.75% formic acid in methanol for 1a; 40 mM $NH_4Oac$ and 0.75% formic acid in 80% DMf/20% $H_2O$ for 1b), with an applied electric field of 140 V/cm, using bare, fused-silica capillaries with an effective/total length of 50/75 cm and 50 μm I.D. hydrodynamic injection for 15 sec at 8 cm height. Ethanol and pure DMF were also tested, but the separation was not acceptable. No bubbles were found in CAE, even when a low boiling point solvent, such as methanol, was used.

One important feature of the experimental protocol is that the reaction mixture was injected into CAE without diluting or quenching before analysis. At predetermined times during the reaction, the reaction block was removed from the heating platform, quickly cooled and put under the injection ends of the capillary array. No deleterious effect on the catalytic system was observed by this operation. By avoiding sample manipulation (e.g. by pipeeting out of the reaction vials), errors associated with transfer and contamination can be reduced. The CAE running buffer should be compatible with the reaction buffer for hydodynamic injection. When using methanol as the buffer, injection was not uniform. Only about half of the 96 capillaries had adequate signal. It was not possible to increase the injection time, because some capillaries then became overloaded When DMF-based buffer was used, all 96 channels had uniform signal over three consecutive runs. This buffer compatibility issue for CAE may be attributed to the differences in solution properties, such as viscosity and surface tension, and was not observed in single-capillary experiments. The total analysis time is typically 60 min, plus 30 min for capillary cleaning Judging from the resolution in FIG. 25, the capillaries could have been shortened to 25% of the effective length to provide analysis times of 15 min.

Figure 26:
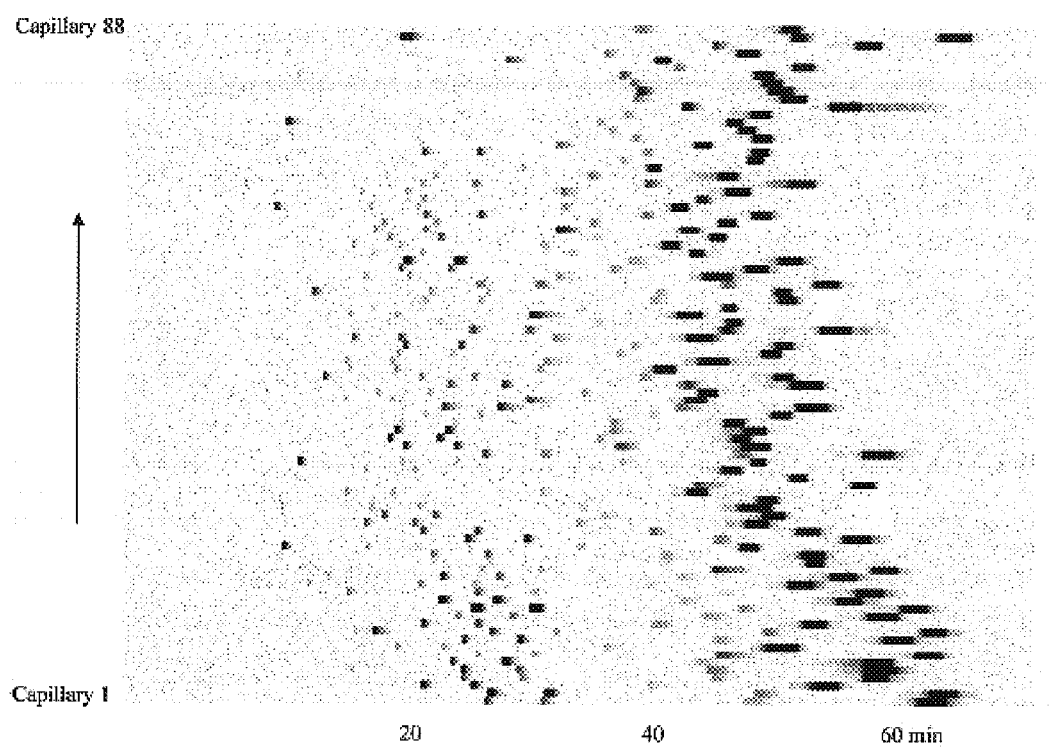
FIG. 26 shows a 96 capillary separation for the reaction conditions for 1b in FIG. 25 and a hydrodynamic injection of 1 min, in which the horizontal direction spans 88 capillaries (the remaining 8 capillaries contained solvent only and were not plotted) and the vertical direction represents time.
Figure 27:
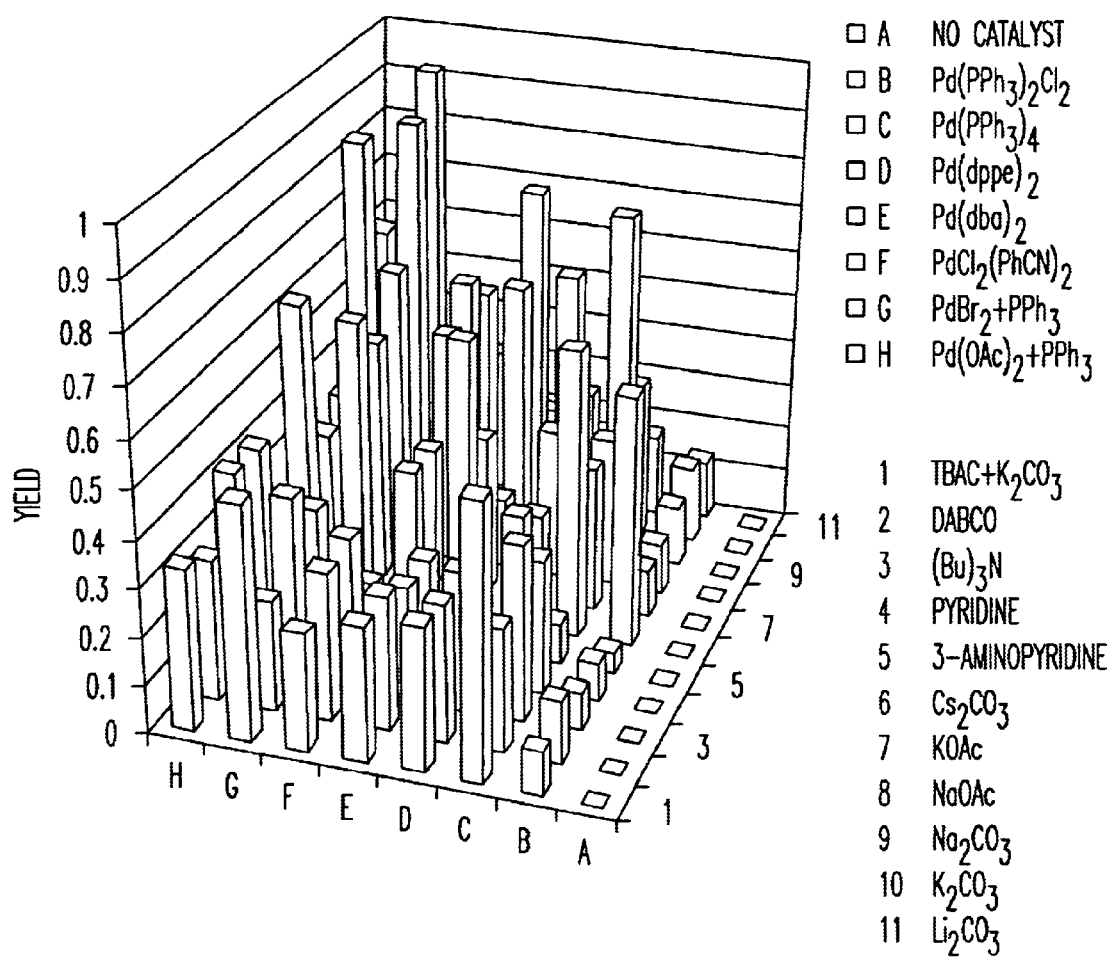
FIG. 27 is a 3-dimensional bar graph of yield vs. catalyst vs. base.
Figure 28:
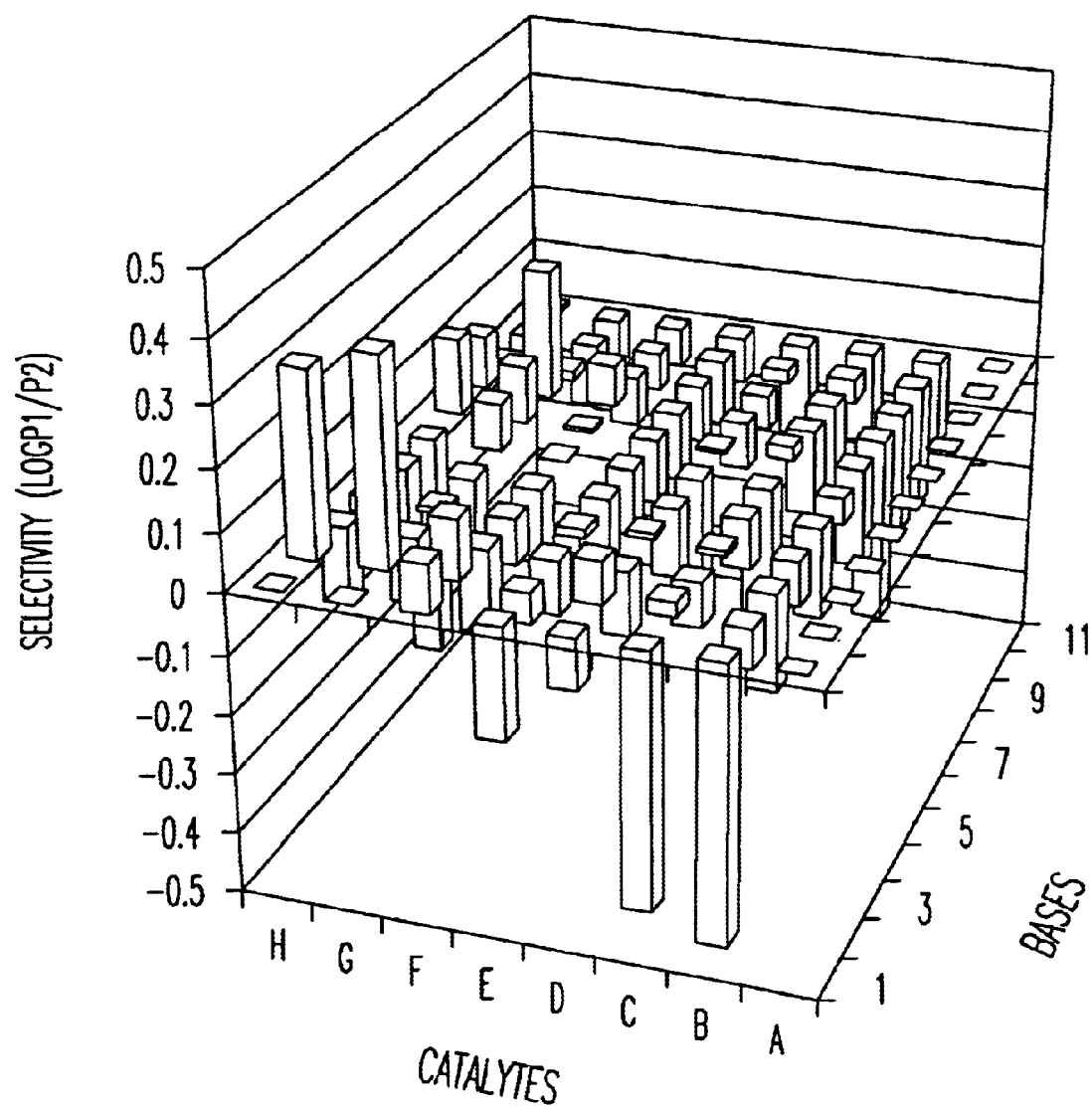
FIG. 28 is a selectivity plot of two isomers produced in the reactions, wherein P1/P2 is the ratio of the two isomers A and B, respectively.
Figure 29:
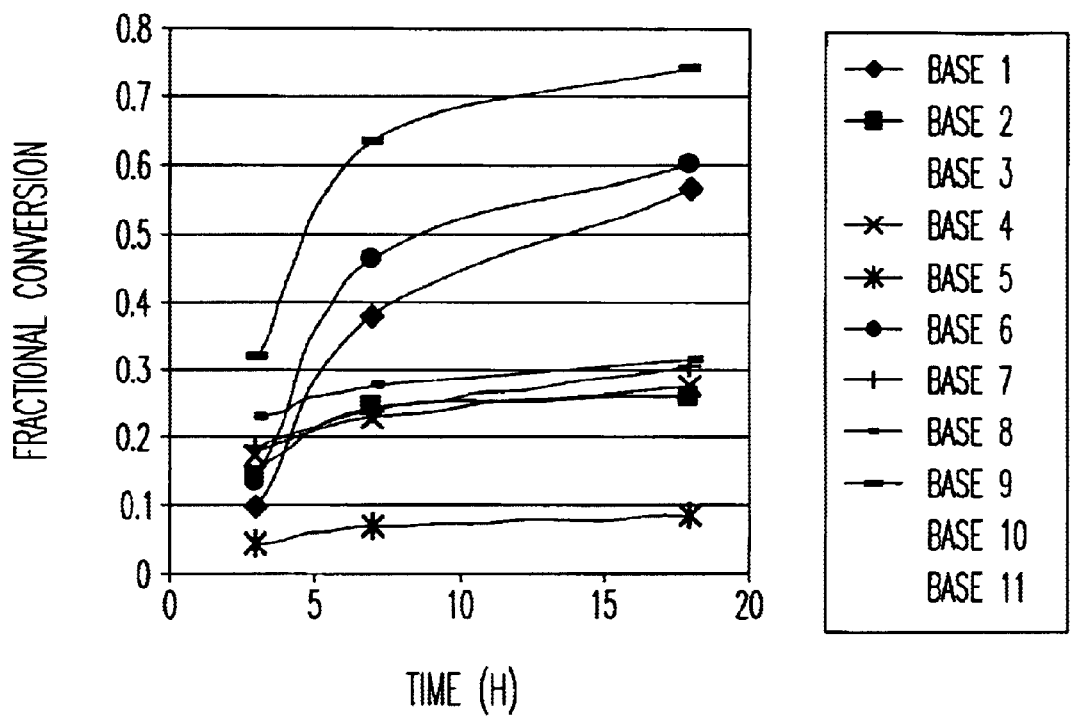
FIG. 29 is a line graph of fractional conversion vs. time (hr) vs. base, for the reaction using $Pd(PPh_3)_4$ as the catalyst and various bases.

By choosing 8 different Pd catalysts and 11 different bases, 88 different combinations were tested. FIG. 26 shows such a 96-capillary sepanttion for the reaction conditions for 1b in FIG. 25 and a hydrodynamic injection of 1 min, in which the horizontal direction spans 88 capillaries (the remaining 8 capillaries contained solvent only and were not plotted) and the vertical direction resents time. Information on the total yield (FIG. 27, which is a 3-dimensional bar graph of yield vs. catalyst vs. base, for reaction after 17 hl at 110° C., in which dppe is bis(diphenylphosphinoethane, TABC is tetra-n-butylammonium chloride, DABCO is 1.4diazabicyclo[2.2.2]octane, and dba is trans, trans-dibenzylidene-acetone), selectivity (FIG. 28, which is the selectivity plot of two isomers produced by the reactions, wherein P1/P2 is the ratio of the two isomers A and B, respectively) and reaction kinetics (FIG. 29, which is a tiun graph of fractional conversion vs. time (hr) vs. base for the rection using $Pd(PPh_3)_4$ as the catalyst and various bases) can be obtained from the electropherogramns. By using $Pd(OAc)_2$ with the ligand $PPh_3$ as catalyst and $Na_2CO_3$ as the base, a total yield of 84% was achieved with virtually no regioselectivity in the microreactor, compared with a quantitative conversion (90% after 17 hours) with no selectivity under the protection of $N_2$ in a 5 mn reaction Among all of the bases, inorganic bases proved to be more effective in promoting the reaction. When pyridine or other organic bases were used, the yield was low and some side products appeared. The ability to detect side products is clearly an advantage of CAE. Preliminary results also reveal several new conditions which are quite effective in this annulation reaction. They are $Pd(PPh_3)_4$ with $Na_2CO_3$ (C9, 74%), $Pd(dba)_2$ with $K_2CO_3$ (E10, 72%), $PdBr_2$ plus $2PPh_3$ with $Na_2CO_3$ (G9, 88%) and $Pdr_2$ plus $2PPh_3$ with $K_2CO_3$ (G10, 96%). The latter two are in fact superior to the previous best catalytic condition (Zhang et al. (1999), supra). Complete regioselectivity is not observed in any of the test conditions (FIG. 28), even though some prove to be better, than other systems. The conditions (2, H2, and B1 have some selectivity, but unfortunately their yields are low. The differences in the rates and the shapes of the plots in FIG. 29 illustraes the need to monitor the reactions at several points in time. No attempt was made to corelate the reaction mechanism with the kinetics in this work.

In summary, a new methodology, nonaqueous capillary array electrophoresis coupled with microreaction, is developed to address the throughput needs of combinatorial approaches to homogeneous catalysis and reaction optimization. Catalytic activity, selectivity and kinetics of the various combinations are determined quickly. This method is potentially useful in the screening for asymmetric catalysts and drugs and combinatorial library synthesis.

Incorporation by Reference

All sources (e.g., inventor's certificates, patent applications, patents, printed publications, repository accessions or records, utility models, World-Wide Web pages, and the like) referred to or cited anywhere in this document or in any drawing, Sequence Listing, or Statement filed concurrently herewith arm hereby incorporated into and made part of this specification by such reference thereto.

Guide to Interpretation

The foregoing is an integrated description of the invention as a whole, not merely of any particular element or facet thereof. The description describes "preferred embodiments" of this invention, including the best mode known to the inventors for carraying it out. Of course, upon reading the foregoing description, variations of those preferred embodiments will become obvious to those of ordinary skill in the art. The inventors expect ordinarily skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law.

As used in the foregoing description and in the following claims, singular indicators (e.g., "a" or "one" include the plural, unless otherwise indicated. Recitation of a range of discontinuous values is intended to serve as a shorthand method of referring individually to each separate value falling within the range, and each separate value is incorporated into the specification as if it were individually listed. As regards the claims in particular, the term "consisting essentially of" indicates that unlisted ingredients or steps that do not materially affect the basic and novel properties of the invention can be employed in addition to the specifically recited ingredients or steps. In contrast, the terms "comprising," "having," or "incorporating" indicate that any ingredients or steps can be present in addition to those recited. The term "consisting of" indicates that only the recited ingredients or steps are present, but does not foreclose the possibility that equivalents of the ingredients or steps can substitute for those specifically recited.

What is claimed is:

1. A method of analyzing multiple samples simultaneously by abosorption detection, in the absence of a mask or slit which method comprises:

(i) providing a planar array of multiple containers, each of which contains a sample comprising at least one absorbing species, (ii) irradating the planar array of multiple containers with a light source comprising at least one wavelength of light that is absorbed by one or more of said at least one absorbing species, the absorption of which is to be detected, and (iii) detecting absorption of light by the one or more of said at least one absorbing species with a detection means that is in line with the light source and is positioned in line with and parallel to the planar array of multiple containers at a distance of at least about 10 times a cross-sectional distance of a container in said planar array of multiple containers measured orthogonally to the plane of the planar array of multiple conatiners wherein the detection of absorption of light by a sample in the planar array of multiple containers indicates the presence of an absorbing species in said sample.

2. The method of claim 1, which further comprises (iv) measuring the amount of absorption of light detectd n (iii) for an absorbing species in a sample, wherein the measurement of the amount of absorption of light detected in (iii) indicates the amount of the absorbing species in the sample.

3. The method of claim 1, wherein the distance is from about 10 cm to about 50 cm.

4. The method of claim 1, wherein said planar array of multiple containers comprises capillary tubes.

5. The method of claim 4, wherein the distance is at least about 10 times the diameter of capillary tube.

6. The method of claim 4, wherein said planar array of multiple containers comprises at least about 10 capillary tubes.

7. The method of claim 6, wherein said planar array of multiple containers comprises at least about 90 capillary tubes.

8. The method of claim 4, wherein the detection limit for rhodamine 6G for each capillary in the planar array of multiple containers is abou $1.8 \times 10^{-8}$ M.

9. The method of claim 8, wherein the cross-talk between adjacent capillaries is less than about 0.2%.

10. The method of claim 8, wherein the cross-talk between adjacent capillaries is less than about 0.2%.

11. The system of claim 4, which further comprises a means to introduce said sample into said capillary tube.

12. The method of claim 11, wherein said sample is introduced into said capillary tube by pressure, gravity, vacumm, capillary or electrophoretic action.

13. The method of claim 1, wherein saidl planar array further comprises at least one control container.

14. The method of claim 1, wherein said detection means comprises a plurality of photosensitive elements in a photodiode array.

15. The method of claim 9, wherein said photodiode array comprises linearly aligned pixels.

16. The method of claim 15, wherein each container in said planar array of multiple containers is a capillary tube and each capillary tube is optically coupled to less than about 10 pixels.

17. The method of claim 16, wherein an optional filter is positioned between said planar array of multiple containers and said detection means, wherein said flat-field lens couples light that is not absorbed by the one of more of said at least one absorbing species in each sample in the planar array of multiple containers with the detection means.

18. The method of claim 17, wherein a flat-field lens is positioned between said planar array of multiple containers and said detection means, wherein said flat-field lens couples light that is not absorbed by the one or more of said at least one absorbing species in each sample in the planar array of multiple containers with the detection means.

19. The method of claim 1, wherein the light source comprises or consists essentially of a wavelength in the range from about 180 nm to about 1500 nm.

20. The method of claim 19, wherein the light source has a power output of about 0.5 mW to about 50 mW.

21. The method of claim 1, wherein an optical filter is positioned between said planar array of multiple containers and said detection means, wherein said optical filter selects at least one wavelength of light from said light source.

22. The method of claim 21, wherein a flat-field lens is positioned between said planar array of multiple containers and said detection means, wherein said flat-field lens couples light that is not absorbed by the one or more of said at least one absorbing species in each sample in the planar array of multiple containers with the detection means.

23. The method of claim 1, wherein a beam expander positioned between said light source and said planary array of multiple containers.

24. The method of claim 1, wherein a collimating focusing lens is positioned between said light source and said planar array of multiple containers.

25. A system for use in analyzing multiple samples simultaneously by absorption detection, which system comprises in the absence of a mask or slit:

(i) a light source comprising or consisting essentially of at least one wavelength of light that is absorbed by one or more absorbing species, the absorption of which is to be detected, (ii) a planar array of multiple containers, into each of which can be pleased a sample comprising at least one absorbing species, and (iii) a detection means that is in line with the light source and is positioned in line with and parallel to the planar array of multiple containers at a distance of at least about 10 times a cross-sectional distance of a container in said planar array of multiple containers mearsured orthogonally to the plane of the planar array of multiple containers.

26. The system of claim 25, wherein the distance is from about 10 cm to about 50 cm.

27. The system of claim 25, wherein said planar array of multiple containers comprises caplillary tubes.

28. The system of claim 27, wherein the distance is at least about 10 times the diameter of a capillary tube.

29. The system of claim 27, wherein said planar array of multiple containers comprises at least about 10 capillary tubes.

30. The system of claim 29, wherein said planar array of multiple containers comprises at least about 90 capillary tubes.

31. The system of claim 27, wherein the detection limit for rhodamine 6G for each capillary in the planar array of multiple containers is about $18 \times 10^{-8}$ M.

32. The system of claim 31, wherein the cross-talk between adjacent capillaries is less than about 0.2%.

33. The system of claim 27, wherein the cross-talk between adjacent capillaries is less than about 0.2%.

34. The system of claim 27, which further comprises a means to introduce said sample into said capillary tube.

35. The system of claim 34, wherein said sample is introduced into said capillary tube by pressure, gravity, vacuum, capillary or electrophorectic action.

36. The system of claim 25, wherein said planar array further comprises at least one control container.

37. The system of claim 25, wherein said detection means comprises a plurality of photosensitive elements in photo-diode array.

38. The system of claim 37, wherein said photodiode array comprises linearly aligned pixels.

39. The system of claim 38, wherein each container in said planar array of multiple containers is a capillary tube and each capillary tube is optically coupled to less than about ten pixels.

40. The system of claim 39, which further comprises an optical filter between said planar array of multiple containers and said detection means, wherein said optical filters selects at least one wavelength of light from said light source.

41. The system of claim 40, which further comprises a flat-field lens between said planar array of multiple containers and said detection means, wherein said flat-field lens couples light that i not absorbed by the one or more of said at least one absorbing species in each sample in the planar array of multiple containers with the detection means.

42. The system of claim 25, wherein the light source comprises or consists essentially of a wavelength in the range from about 180 nm to about 1500 nm.

43. The system of claim 42, wherein the light source has a power output of about 0.5 mW to about 50 mW.

44. The system of claim 25, which further comprises an optical filter between said planar array of multiple containers and said detection means, wherein said optical filter selects at least one wavelength of light from said light source.

45. The system of claim 44, which further comprises a flat-field lens between said planar array of multiple containers and said detection means, wherein said flat-field lens couples light that is not absorbed by the one or more of said least one absorbing species in each sample in the planar array of multiple containers with the detection means.

46. The system of claim 25, which furter comprises a beam expander between said light source and said planar array of the multiple containers.

47. The system of claim 25, which further comprises a collimating focusing lens between said light source and said planar array of multiple containers.

48. A method of analyzing multiple samples simultaneously by absorption detection in the absence of a mask, or slit, which method comprises:
   (i) providing a planar array of multiple containers, each of which contains a sample comprising at least one absorbing species,
   (ii) irradiating the planar array of multiple containers with a light source comprising at least one wavelength of light that is absorbed by one or more of said at least one absorbing species, the absorption of which is to be detected, and
   (iii) detecting absorption of light by one or more of said at least one absorbing species with a detection means that is line with the light source and is positioned in line with the parallel to the planar array of multiple containers at a distance of at least about 10 time a cross-sectional distance of a container in said planar array of multiple containers measured orthogonally to the to the plane of the planar array of multiple containers,
   wherein the detection of absorption of light by a sample in the planar array of multiple containers indicates the presence of an absorbing species in said sample.

49. A method of analyzing multiple samples simultaneously by absorption detection in the absence of a mask, or slit, which method comprises:
   (i) providing a planar array of multiple containers, each of which contains a sample comprising at least one absorbing species,
   (ii) irradating the planar array of multiple containers with a light source comprising at least one wavelength of light that is absorbed by one or more of said at least one absorbing species, the absorption of which is to be detected, and
   (iii) detecting absorption of light by one or more of said at least one absorbing species with a detection means that is line with the light source and is positioned in line with and parallel to the planar, array of multiple containers at a distance of at least about 100 times a cross-sectional distance of a container in said planar array of multiple containers measured orthogonally to the to the plane of the planar array of multiple containers,
   wherein the detection of absorption of light by a sample in the planar array of multiple containers indicates the presence of an absorbing species in said sample.

* * * * *

UNITED STATES PATENT AND TRADEMARK OFFICE
CERTIFICATE OF CORRECTION

PATENT NO. : 6,788,414 B1
DATED : September 7, 2004
INVENTOR(S) : Yeung et al.

It is certified that error appears in the above-identified patent and that said Letters Patent is hereby corrected as shown below:

Title page,
Item [54], Title, should read -- METHOD OF ANALYZING MULTIPLE SAMPLES SIMULTANEOUSLY BY DETECTING ABSORPTION ANS SYSTEMS FOR USE IN SUCH A METHOD --
Item [57], ABSTRACT,
Beginning line 15, should read -- amount of the absorbing species in the sample. Also provided by the present invention is a system for use in the above method. The system comprises: (i) a light source comprising or consisting essentially of at least one wavelength of light, the absorption of which is to be detected, (ii) a planar array of multiple containers, and (iii) a detection means that is in line with the light source and is positioned in line with and parallel to the planar array of multiple containers at a distance of at least about 10 times a cross-sectional distance of a container.

Column 41,
Line 42, should read -- containers, --
Line 47, should read -- measuring the amount of absorption of light detected in (iii) --
Line 56, should read -- about 10 times the diameter of a capillary tube. --

Column 42,
Line 8, should read -- 13. The method of claim 1, wherein said planar array --
Line 17, should read -- about ten pixels. --
Line 45, should read -- 23. The method of claim 1, wherein a beam expander is --
Line 59, should read -- which can be placed a sample comprising at least one --
Line 65, should read -- in said planar array of multiple containers measured --

Column 43,
Line 16, should read -- 32. The system of claim 27, wherein the cross-talk --
Line 43, should read -- couples light that is not absorbed by the one or more of said --

UNITED STATES PATENT AND TRADEMARK OFFICE
CERTIFICATE OF CORRECTION

PATENT NO. : 6,788,414 B1
DATED : September 7, 2004
INVENTOR(S) : Yeung et al.

It is certified that error appears in the above-identified patent and that said Letters Patent is hereby corrected as shown below:

Column 44,
Line 24, should read -- with and parallel to the planar array of multiple containers --
Line 47, should read -- with and parallel to the planar array of multiple containers --

Signed and Sealed this

Nineteenth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,788,414 B1
DATED : September 7, 2004
INVENTOR(S) : Yeung et al.

It is certified that error appears in the above-identified patent and that said Letters Patent is hereby corrected as shown below:

Title page,
Item [54], Title, should read -- METHOD OF ANALYZING MULTIPLE SAMPLES SIMULTANEOUSLY BY DETECTING ABSORPTION AND SYSTEMS FOR USE IN SUCH A METHOD --
Item [57], ABSTRACT,
Beginning line 15, should read -- amount of the absorbing species in the sample. Also provided by the present invention is a system for use in the above method. The system comprises: (i) a light source comprising or consisting essentially of at least one wavelength of light, the absorption of which is to be detected, (ii) a planar array of multiple containers, and (iii) a detection means that is in line with the light source and is positioned in line with and parallel to the planar array of multiple containers at a distance of at least about 10 times a cross-sectional distance of a container.

Column 41,
Line 42, should read -- containers, --
Line 47, should read -- measuring the amount of absorption of light detected in (iii) --
Line 56, should read -- about 10 times the diameter of a capillary tube. --

Column 42,
Line 8, should read -- 13. The method of claim 1, wherein said planar array --
Line 17, should read -- about ten pixels. --
Line 45, should read -- 23. The method of claim 1, wherein a beam expander is --
Line 59, should read -- which can be placed a sample comprising at least one --
Line 65, should read -- in said planar array of multiple containers measured --

Column 43,
Line 15, should read -- $1.8 \times 10^{-8}$ M --
Line 16, should read -- 32. The system of claim 27, wherein the cross-talk --
Line 43, should read -- couples light that is not absorbed by the one or more of said --

UNITED STATES PATENT AND TRADEMARK OFFICE
CERTIFICATE OF CORRECTION

PATENT NO. : 6,788,414 B1
DATED : September 7, 2004
INVENTOR(S) : Yeung et al.

It is certified that error appears in the above-identified patent and that said Letters Patent is hereby corrected as shown below:

Column 44,
Line 24, should read -- with and parallel to the planar array of multiple containers --
Line 47, should read -- with and parallel to the planar array of multiple containers --

This certificate supersedes Certificate of Correction issued April 19, 2005.

Signed and Sealed this

Twenty-eighth Day of June, 2005

JON W. DUDAS
*Director of the United States Patent and Trademark Office*